US012358965B2

(12) United States Patent
Verdino et al.

(10) Patent No.: US 12,358,965 B2
(45) Date of Patent: Jul. 15, 2025

(54) RELAXIN ANALOGS AND METHODS OF USING THE SAME

(71) Applicant: Eli Lilly and Company, Indianapolis, IN (US)

(72) Inventors: Petra Verdino, San Diego, CA (US); Stacey Lynn Lee, San Diego, CA (US); Xiaojun Wang, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 429 days.

(21) Appl. No.: 17/632,107

(22) PCT Filed: Jul. 31, 2020

(86) PCT No.: PCT/US2020/044462
§ 371 (c)(1),
(2) Date: Feb. 1, 2022

(87) PCT Pub. No.: WO2021/022139
PCT Pub. Date: Feb. 4, 2021

(65) Prior Publication Data
US 2022/0275042 A1 Sep. 1, 2022

Related U.S. Application Data

(60) Provisional application No. 62/970,005, filed on Feb. 4, 2020, provisional application No. 62/880,968, filed on Jul. 31, 2019.

(51) Int. Cl.
| | | |
|---|---|---|
| A61K 47/68 | (2017.01) | |
| A61K 31/155 | (2006.01) | |
| A61K 31/426 | (2006.01) | |
| A61K 31/64 | (2006.01) | |
| A61K 38/22 | (2006.01) | |
| A61K 38/30 | (2006.01) | |
| A61K 39/00 | (2006.01) | |
| A61K 45/06 | (2006.01) | |
| A61K 47/65 | (2017.01) | |
| A61P 3/10 | (2006.01) | |
| A61P 9/00 | (2006.01) | |
| C07K 14/64 | (2006.01) | |
| C07K 16/18 | (2006.01) | |
| C07K 16/28 | (2006.01) | |

(52) U.S. Cl.
CPC ............ *C07K 14/64* (2013.01); *A61K 31/155* (2013.01); *A61K 31/426* (2013.01); *A61K 31/64* (2013.01); *A61K 38/22* (2013.01); *A61K 38/30* (2013.01); *A61K 45/06* (2013.01); *A61K 47/6811* (2017.08); *A61P 3/10* (2018.01); *C07K 16/18* (2013.01); *C07K 16/2863* (2013.01); *A61K 2039/505* (2013.01); *C07K 2317/92* (2013.01); *C07K 2319/02* (2013.01); *C07K 2319/31* (2013.01); *C07K 2319/40* (2013.01)

(58) Field of Classification Search
None
See application file for complete search history.

(56) References Cited

U.S. PATENT DOCUMENTS

| | | |
|---|---|---|
| 2010/0113339 A1 | 5/2010 | Beirnaert et al. |
| 2010/0216187 A1 | 8/2010 | Lasters et al. |
| 2012/0148571 A1 | 6/2012 | Lasters et al. |
| 2014/0228546 A1 | 8/2014 | Dombrecht et al. |
| 2018/0312578 A1 | 11/2018 | Buyse |
| 2019/0367596 A1 | 12/2019 | Staelens et al. |

FOREIGN PATENT DOCUMENTS

| | | |
|---|---|---|
| WO | 2006122787 A1 | 11/2006 |
| WO | 2011140086 A2 | 11/2011 |
| WO | 2013004607 A1 | 1/2013 |
| WO | 2017100540 A2 | 6/2017 |
| WO | 2018138170 A1 | 8/2018 |
| WO | 2019014360 A1 | 1/2019 |
| WO | 2019016237 A1 | 1/2019 |
| WO | 2019106193 A1 | 6/2019 |
| WO | 2019204925 A1 | 10/2019 |

OTHER PUBLICATIONS

Patent Cooperation Treaty International Search Report pertaining to International Application No. PCT/US2020/044462; International Filing Date: Jul. 31, 2020; Date of Mailing: Oct. 28, 2020.
Patent Cooperation Treaty Written Opinion of the International Searching Authority pertaining to International Application No. PCT/US2020/044462; International Filing Date: Jul. 31, 2020; Date of Mailing: Oct. 28, 2020.
Japanese Office Action dated May 23, 2023; JP Application No. 2022-506024.
Japanese Office Action dated Jan. 4, 2023; JP Application No. 2022-506024.
Van Faassen, H., Ryan, S., Henry, K. A., Raphael, S., Yang, Q., Rossotti, M. A., . . . & Hussack, G. 2020. Serum albumin-binding VHHs with variable pH sensitivities enable tailored half-life extension of biologics. The FASEB Journal, 34(6), 8155-8171.
L. J. Holt et al (2008); Anti-serum albumin domain antibodies for extending the half-lives of short lived drugs; Protein Engineering, Design & Selection vol. 21 No. 5 pp. 283-288, 2008.

(Continued)

*Primary Examiner* — Ruixiang Li
(74) *Attorney, Agent, or Firm* — Matthew T. Lord

(57) ABSTRACT

Relaxin (RLN) analogs are disclosed including modifications that increase half-life when compared to native, human RLN, that maintain selectivity to the RXFP1 receptor and that provide in vitro and in vivo stability for improved druggability properties and less immunogenicity. Pharmaceutical compositions also are disclosed that include one or more of the RLN analogs described herein in a pharmaceutically acceptable carrier. Methods of making and using the RLN analogs also are disclosed, especially for treating cardiovascular, pulmonary and/or renal conditions, diseases or disorders.

18 Claims, No Drawings
Specification includes a Sequence Listing.

(56) References Cited

OTHER PUBLICATIONS

A. Walker et al (2010); Anti-serum albumin domain antibodies in the development of highly potent, efficacious and long-acting interferon. Protein Engineering, Design & Selection vol. 23 No. 4 pp. 271-278, 2010.

Dschietzig, T.B., "Relaxin-2 for heart failure with preserved ejection fraction (HFpEF): Rationale for future clinical trials," Molecular and Cellular Endocrinology 487, 2019, 54-58.

Verdino, P. et al., "Development of a long-acting relaxin analogue, LY3540378, for treatment of chronic heart failure," Br J Pharmacol. 2023; 180: 1965-1980.

RELAXIN ANALOGS AND METHODS OF USING THE SAME

The disclosure relates generally to biology and medicine, and more particularly it relates to relaxin (RLN) analogs, especially long-acting, single-chain RLN analogs that can bind to a RLN/insulin-like family peptide (RXFP) receptor, such as the RXFP1 receptor, thereby functioning as RXFP receptor agonists. The disclosure further relates to compositions including the same and their use in treating cardiovascular, pulmonary and/or renal conditions, diseases or disorders.

Relaxins (RLNs) are part of the insulin superfamily and, in humans, include seven peptides of high structural, but low sequence, similarity—RLN1 (H1RLX, RLXH1 or H1), RLN2 (H2RLX, RLXH2 or H2), RLN3 (RXN3, ZINS4 or H3), insulin-like (INSL) peptide 3 (INSL3), INSL4, INSL5 and INSL6. Of particular interest herein is RLN2, which is a heterodimer of two peptide chains of twenty-four and twenty-nine amino acids (A chain and B chain), respectively, linked by two disulfide bonds with the A chain further having one intramolecular disulfide bond (see, Schwabe & McDonald (1977) *Science* 197:914-915). RLN2 is produced from its prohormone, prorelaxin, by cleaving a C peptide therefrom.

Physiologically, RLN2 exhibits a diverse array of functions that modulate cardiovascular, hepatic, neural, pancreatic, pulmonary and renal adaptations such as vasodilatory, anti-fibrotic and angiogenic effects, even though it initially was described as a pregnancy hormone. RLN2 signaling occurs through two different classes of G-protein-coupled receptors (GPCRs), namely, leucine-rich repeat-containing GPCRs LGR7 and LGR8, now referred to as the RXFP1 and RXFP2 receptors, respectively. Two other receptors in this family include the RXFP3 and RXFP4 receptors. RLN2 has a short half-life (t½), which presents challenges when using it as a therapeutic agent. In fact, native RLN2 has a t½ of minutes in vivo. Consequently, clinicians administer RLN2 by continuous intravenous infusion, which often results in inconvenience for individuals receiving the RLN compound and in short-term efficacy.

A number of RLN2 analogs exist having an improved t½. For example, Intl. Patent Application Publication No. WO 2018/148419 describes analogs that include a non-native amino acid residue such as para-acetyl-phenylalanine to which linkers, polymers and/or pharmacokinetic enhancers can be attached to improve t½. Intl. Patent Application Publication No. WO 2018/138170 describes analogs that are fusions of the A chain and B chain having a linker of at least fifteen amino acids and a half-life extending moiety to improve t½. Intl. Patent Application Publication No. WO 2017/201340 describes analogs that are fusions of the A chain and B chain having a variable light chain fragment to improve t½. Intl. Patent Application Publication No. WO 2015/067791 describes analogs that are carrier-linked prodrugs, especially PEG-based carriers, to improve t½ (see also, WO 2012/024452 for additional PEG-linked analogs). Intl. Patent Application Publication No. WO 2014/102179 describes analogs that are fusions of the A chain and B chain having a Fc moiety of IgG2 or IgG4 to improve t½. Intl. Patent Application Publication No. WO 2013/004607 describes analogs that are fusions of the A chain and B chain having a linker of at least five amino acids but less than fifteen amino acids to improve t½ or that are fusions of the A chain and B chain having a Fc domain of antibodies to improve t½.

In view of the increases in understanding the various physiological roles of RLNs, there remains a need for long-acting RLN analogs having an improved t½.

To address this need, the disclosure first describes single-chain RLN analogs having principal activity at the RXFP1 receptor (i.e., act as RXFP1 receptor agonists). Such RXFP1 receptor agonists include a basic structure from an amino-terminus (N-terminus) to a carboxy-terminus (C-terminus) of:

VHH-$L_1$-A-$L_2$-B,

VHH-$L_1$-B-$L_2$-A,

A-$L_2$-B-$L_1$-VHH, or

B-$L_2$-A-$L_1$-VHH, where VHH is a moiety that can act as a pharmacokinetic enhancer, A is a RLN A chain, B is a RLN B chain, $L_1$ is a first linker, and $L_2$ is a second linker.

In some instances, the VHH moiety can have an amino acid sequence of SEQ ID NO:10, 11, 12 or 13, especially SEQ ID NO:10 or 12. In other instances, the VHH moiety can have one or more additions, deletions, insertions or substitutions such that the VHH moiety has an amino acid sequence having at least about 90% to about 99% sequence similarity to any one of SEQ ID NOS:10, 11, 12 or 13 (see, e.g., SEQ ID NOS:45-66).

In some instances, the A chain can have an amino acid sequence of SEQ ID NO:2, 5 or 8, especially SEQ ID NO:5. In other instances, the A chain can have one or more additions, deletions, insertions or substitutions such that the A chain has an amino acid sequence having at least about 90% to about 99% sequence similarity to any one of SEQ ID NOS:2, 5 or 8. For example, the A chain can be des1-4 of SEQ ID NO:5.

In some instances, the B chain can have an amino acid sequence of SEQ ID NO:3, 6 or 9, especially SEQ ID NO:6. In other instances, the B chain can have one or more additions, deletions, insertions or substitutions such that the B chain has an amino acid sequence having at least about 90% to about 99% sequence similarity to any one of SEQ ID NOS:3, 6 or 9. For example, the B chain can be des1 of SEQ ID NO:6.

In some instances, $L_1$ can have an amino acid sequence of $(GGGGQ)_n$ (SEQ ID NO:14), $(GGGQ)_n$ (SEQ ID NO:15), $(GGGGS)_n$ (SEQ ID NO:16), $(PGPQ)_n$ (SEQ ID NO:17) or $(PGPA)_n$ (SEQ ID NO:18), where n can be from 1 to 10, especially from about 5 to about 8. In other instances, $L_1$ can have an amino acid sequence of SEQ ID NO:19, 20 or 21. In still other instances, $L_1$ can have one or more additions, deletions, insertions or substitutions such that $L_1$ has an amino acid sequence having at least about 90% to about 99% sequence similarity to any one of SEQ ID NOS:14 to 21.

In some instances, $L_2$ can have an amino acid sequence of SEQ ID NO:22, 23 or 67. In other instances, $L_2$ can have one or more additions, deletions, insertions or substitutions.

In certain instances, the RLN analogs can have an amino acid sequence that includes a VHH of SEQ ID NO:10, 11, 12 or 13; an A chain of SEQ ID NO:2, 5 or 8; a B chain of SEQ ID NO:3, 6 or 9; a $L_1$ of SEQ ID NO:19, 20 or 21; and a $L_2$ of SEQ ID NO:22, 23 or 67. Alternatively, the RLN analogs can have an amino acid sequence having at least about 90% to about 99% sequence similarity to an amino acid sequence that includes an amino acid sequence that includes a VHH of SEQ ID NO:10, 11, 12 or 13; an A chain of SEQ ID NO:2, 5 or 8; a B chain of SEQ ID NO:3, 6 or 9; a L$_1$ of SEQ ID NO:19, 20 or 21; and a L$_2$ of SEQ ID NO:22, 23 or 67.

In particular instances, the RLN analogs can have an amino acid sequence of SEQ ID NO:24, 25, 26, 27, 28, 29, 30, 31, 32, 33, 34, 35, 36, 37, 38 or 39, especially SEQ ID NO:26, 27, 30, 31, 34 or 35. Alternatively, the RLN analogs can have an amino acid sequence having at least about 90% to about 99% sequence similarity to an amino acid sequence of SEQ ID NO:24, 25, 26, 27, 28, 29, 30, 31, 32, 33, 34, 35, 36, 37, 38 or 39, especially SEQ ID NO:26, 27, 30, 31, 34 or 35.

In some instances, the RLN analogs have a binding affinity at a RXFP1 receptor that is comparable to the binding affinity of native, human RLN2 (SEQ ID NOS:5 and 6). In other instances, the RLN analogs have a binding affinity at a RXFP1 receptor that is greater than that of native, human RLN2 (SEQ ID NOS:5 and 6). In still other instances, the RLN analogs have a binding affinity at a RXFP1 receptor that is less than that of native, human RLN2 (SEQ ID NOS:5 and 6).

In some instances, the RLN analogs have a t½ that is longer than that of native, human RLN2 (SEQ ID NOS:5 and 6), including up to about 20 days to about 30 days longer when administered to a human.

The compositions above alternatively can be nucleic acid sequences encoding the amino acid sequences described herein, as well as vectors and host cells including the same for expressing the RLN analogs herein.

Second, pharmaceutical compositions are described that include at least one RLN analog herein or a pharmaceutically acceptable salt thereof (e.g., trifluroacetate salts, acetate salts or hydrochloride salts) and a pharmaceutically acceptable carrier. In some instances, the pharmaceutically acceptable carrier is a buffer such as, for example, physiological saline, phosphate-buffered saline, citrate-buffered saline or histidine-buffered saline. In certain instances, the buffer is histidine, a histidine buffer or a histidine-buffered saline. In other instances, the pharmaceutical compositions further can include carriers, diluents and/or excipients.

Moreover, the pharmaceutical compositions can include at least one additional therapeutic agent such as, for example, an agent used as a standard of care in a cardiovascular, pulmonary and/or renal condition, disease or disorder. In some instances, the at least one additional therapeutic agent can be an anticoagulant, an angiotensin-converting enzyme (ACE) inhibitor, an angiotensin II receptor blocker (ARB), an ARB neprilysin inhibitor (ARNI), a β-blocker, a diuretic, digitalis, digoxin, hydralazine/isorbide dinitrate, a mineralocorticoid receptor antagonist (MRA; or aldosterone antagonist), a sodium-glucose cotransporter-2 (SGLT2) inhibitor, a statin and/or an anti-glycemic agent.

Third, methods are described for using the RLN analogs herein, especially for using the RLN analogs to treat cardiovascular, pulmonary and/or renal conditions, diseases or disorders. The methods include at least a step of administering to an individual in need thereof an effective amount of at least one RLN analog herein or a pharmaceutically acceptable salt thereof.

In some instances, the RLN analog can be administered via any standard route of administration such as, for example, intramuscularly, intravenously, parenterally, subcutaneously or transdermally. In certain instances, the RLN analog is administered subcutaneously (SQ), intramuscularly (IM) or intravenously (IV). In particular instances, the RLN analog can be administered SQ or IV to the individual.

Likewise, and in some instances, the RLN analog can be administered daily, every other day, three times a week, two times a week, one time a week (i.e., weekly), biweekly (i.e., every other week), one time a month (i.e., monthly), bimonthly (i.e., every other month), or even every three months. In certain instances, the RLN analog can be administered SQ every other day, SQ three times a week, SQ two times a week, SQ one time a week, SQ every other week, or SQ once a month. In particular instances, the RLN analog is administered SQ one time a week (QW).

Alternatively, the RLN analog can be IV administered to the individual. As above, the RLN analog can be administered daily, every other day, three times a week, two times a week, one time a week (i.e., weekly), biweekly (i.e., every other week), or monthly. In certain instances, the RLN analog can be administered IV every other day, IV three times a week, IV two times a week, IV one time a week, IV every other week, or IV once a month. In particular instances, the RLN analog is administered IV one time a week.

The methods also can include a step of administering the RLN analog in combination with an effective amount of at least one additional therapeutic agent. Briefly, the standard of care for many of the conditions/diseases/disorders herein includes an anticoagulant, an ACE inhibitor, an ARB, an ARNI, a β-blocker, a diuretic, digitalis, digoxin, hydralazine/isorbide dinitrate, a MRA or other aldosterone antagonist, a SGLT2 inhibitor, a statin and/or an anti-glycemic agent, as well as other therapeutic agents to control comorbidities, including, but not limited to, high cholesterol, high blood pressure, atrial fibrillation and diabetes. In some instances, the additional therapeutic agent can be administered simultaneously, separately or sequentially with the RLN analog.

For example, the additional therapeutic agent can be administered with a frequency the same as the RLN analog (i.e., every other day, twice a week, weekly or even monthly). In other instances, the additional therapeutic agent can be administered with a frequency distinct from the RLN analog. In other instances, the additional therapeutic agent can be administered SQ or IV. In still other instances, the RLN analog is administered SQ, and the additional therapeutic agent can be administered orally or IV. Alternatively, the RLN analog is administered IV, and the additional therapeutic agent is administered SQ.

In some instances, the individual in need is a diabetic, hypertensive with kidney function impairment and/or obese.

The methods also may include steps such as measuring or obtaining blood pressure and comparing such obtained values to one or more baseline values or previously obtained values to assess the effectiveness of treatment/therapy.

The methods also may be combined with diet and exercise and/or may be combined with additional therapeutic agents other than those discussed above.

Fourth, uses are described that include at least one of the RLN analogs herein. For example, the RLN analogs herein can be provided for use in therapy, especially in treating cardiovascular, pulmonary and/or renal conditions, diseases or disorders. The RLN analogs optionally can be administered simultaneously, separately or sequentially (i.e., in combination) with at least one additional therapeutic agent. Likewise, use of the RLN analogs herein is provided in manufacturing a medicament for treating cardiovascular, pulmonary and/or renal conditions, diseases or disorders, where the medicament optionally may further include one or more additional therapeutic agents as noted above.

Fifth, a compound is provided that includes an amino acid sequence of: EVQLLESGGGLVQPGGSLRLSCAAS-GRYIDETAVAWFRQAPGKEREFVAGIGGG VDITYY-ADSVKGRFTISRDNSKNTLYLQMNSLRPEDTAVYY-CAARPGRPLITSKV ADLYPYWGQGTLVTVSS (SEQ ID NO:10). In some instances, the compound can have an amino acid sequence having at least about 90% to about 99% sequence similarity to SEQ ID NO:10.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRPLITSKV ADLYPYWGQGTLVTVSSPP (SEQ ID NO:11). In some instances, the compound can have an amino acid sequence having at least about 90% to about 99% sequence similarity to SEQ ID NO:11.

Alternatively, a compound is provided that includes an amino acid sequence of: EVQLLESGGGLVQPGGSLRLS-CAASGRYIDETAVAWFRQAPGKGREFVAGIGGG VDI-TYYADSVKGRFTISRDNSKNTLYLQMNSLRPED-TAVYYCAARPGRPLITSKV ADLYPYWGQGTLVTVSS (SEQ ID NO:12). In some instances, the compound can have an amino acid sequence having at least about 90% to about 99% sequence similarity to SEQ ID NO:12.

Alternatively, a compound is provided that includes an amino acid sequence of: EVQLLESGGGLVQPGGSLRLS-CAASGRYIDETAVAWFRQAPGKGREFVAGIGGG VDI-TYYADSVKGRFTISRDNSKNTLYLQMNSLRPED-TAVYYCAARPGRPLITSKV ADLYPYWGQGTLVTVSSPP (SEQ ID NO:13). In some instances, the compound can have an amino acid sequence having at least about 90% to about 99% sequence similarity to SEQ ID NO:13.

Alternatively, a compound is provided that includes an amino acid sequence of: EVQLLESGGGLVQPGGSLRLS-CAASGRTVSSTAVAWFRQAPGKEREFVAGIGGS VDI-TYYADSVKGRFTISRDNSKNTLYLQMNSLRPED-TAVYYCAVRPGRPLITSRD ANLYDYWGQGTLVTVSS (SEQ ID NO:45). In some instances, the compound can have an amino acid sequence having at least about 90% to about 99% sequence similarity to SEQ ID NO:45.

Alternatively, a compound is provided that includes an amino acid sequence of: EVQLLESGGGLVQPGGSLRLS-CAASGRYIDSTAVAWFRQAPGKEREFVAGIGGG VDI-TYYADSVKGRFTISRDNSKNTLYLQMNSLRPED-TAVYYCAARPGRPLITSRV ANLYPYWGQGTLVTVSS (SEQ ID NO:46). In some instances, the compound can have an amino acid sequence having at least about 90% to about 99% sequence similarity to SEQ ID NO:46.

Alternatively, a compound is provided that includes an amino acid sequence of: EVQLLESGGGLVQPGGSLRLS-CAASYRYIDETAVAWFRQAPGKEREFVAGIGGG VDI-TYYADSVKGRFTISRDNSKNTLYLQMNSLRPED-TAVYYCAARPGRPLITSKV ADLYPYWGQGTLVTVSS (SEQ ID NO:47). In some instances, the compound can have an amino acid sequence having at least about 90% to about 99% sequence similarity to SEQ ID NO:47.

Alternatively, a compound is provided that includes an amino acid sequence of: EVQLLESGGGLVQPGGSLRLS-CAASGAYIDETAVAWFRQAPGKEREFVAGIGGG VDI-TYYADSVKGRFTISRDNSKNTLYLQMNSLRPED-TAVYYCAARPGRPLITSKV ADLYPYWGQGTLVTVSS (SEQ ID NO:48). In some instances, the compound can have an amino acid sequence having at least about 90% to about 99% sequence similarity to SEQ ID NO:48.

Alternatively, a compound is provided that includes an amino acid sequence of: EVQLLESGGGLVQPGGSLRLS-CAASGRYIDETAVAWFRQAPGKEREFVAGIGGG VDE-TYYADSVKGRFTISRDNSKNTLYLQMNSLRPED-TAVYYCAARPGRPLITSKV ADLYPYWGQGTLVTVSS (SEQ ID NO:49). In some instances, the compound can have an amino acid sequence having at least about 90% to about 99% sequence similarity to SEQ ID NO:49.

Alternatively, a compound is provided that includes an amino acid sequence of: EVQLLESGGGLVQPGGSLRLS-CAASGRYIDETAVAWFRQAPGKEREFVAGIGGG VDQTYYADSVKGRFTISRDNSKNTLYLQMNSLRPED-TAVYYCAARPGRPLITSK VADLYPYWGQGTLVTVSS (SEQ ID NO:50). In some instances, the compound can have an amino acid sequence having at least about 90% to about 99% sequence similarity to SEQ ID NO:50.

Alternatively, a compound is provided that includes an amino acid sequence of: EVQLLESGGGLVQPGGSLRLS-CAASGRYIDETAVAWFRQAPGKEREFVAGIGGG VDI-TAYADSVKGRFTISRDNSKNTLYLQMNSLRPED-TAVYYCAARPGRPLITSKV ADLYPYWGQGTLVTVSS (SEQ ID NO:51). In some instances, the compound can have an amino acid sequence having at least about 90% to about 99% sequence similarity to SEQ ID NO:51.

Alternatively, a compound is provided that includes an amino acid sequence of: EVQLLESGGGLVQPGGSLRLS-CAASGRYIDETAVAWFRQAPGKEREFVAGIGGG VDITEYADSVKGRFTISRDNSKNTLYLQMNSLRPED-TAVYYCAARPGRPLITSKV ADLYPYWGQGTLVTVSS (SEQ ID NO:52). In some instances, the compound can have an amino acid sequence having at least about 90% to about 99% sequence similarity to SEQ ID NO:52.

Alternatively, a compound is provided that includes an amino acid sequence of: EVQLLESGGGLVQPGGSLRLS-CAASGRYIDETAVAWFRQAPGKEREFVAGIGGG VDITQYADSVKGRFTISRDNSKNTLYLQMNSLRPED-TAVYYCAARPGRPLITSKV ADLYPYWGQGTLVTVSS (SEQ ID NO:53). In some instances, the compound can have an amino acid sequence having at least about 90% to about 99% sequence similarity to SEQ ID NO:53.

Alternatively, a compound is provided that includes an amino acid sequence of: EVQLLESGGGLVQPGGSLRLS-CAASGRYIDETAVAWFRQAPGKEREFVAGIGGG VDITSYADSVKGRFTISRDNSKNTLYLQMNSLRPED-TAVYYCAARPGRPLITSKV ADLYPYWGQGTLVTVSS (SEQ ID NO:54). In some instances, the compound can have an amino acid sequence having at least about 90% to about 99% sequence similarity to SEQ ID NO:54.

Alternatively, a compound is provided that includes an amino acid sequence of: EVQLLESGGGLVQPGGSLRLS-CAASGRYIDETAVAWFRQAPGKEREFVAGIGGG VDITTYADSVKGRFTISRDNSKNTLYLQMNSLRPED-TAVYYCAARPGRPLITSKV ADLYPYWGQGTLVTVSS (SEQ ID NO:55). In some instances, the compound can have an amino acid sequence having at least about 90% to about 99% sequence similarity to SEQ ID NO:55.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGKPLITSKV ADLYPYWGQGTLVTVSS (SEQ ID NO:56). In some instances, the compound can have an amino acid sequence having at least about 90% to about 99% sequence similarity to SEQ ID NO:56.

Alternatively, a compound is provided that includes an amino acid sequence of: EVQLLESGGGLVQPGGSLRLS-CAASGRYIDETAVAWFRQAPGKEREFVAGIGGG VDI- TYYADSVKGRFTISRDNSKNTLYLQMNSLRPED-TAVYYCAARPGQPLITSKV ADLYPYWGQGTLVTVSS (SEQ ID NO:57). In some instances, the compound can have an amino acid sequence having at least about 90% to about 99% sequence similarity to SEQ ID NO:57.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGSPLITSKV ADLYPYWGQGTLVTVSS (SEQ ID NO:58). In some instances, the compound can have an amino acid sequence having at least about 90% to about 99% sequence similarity to SEQ ID NO:58.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRELITSKV ADLYPYWGQGTLVTVSS (SEQ ID NO:59). In some instances, the compound can have an amino acid sequence having at least about 90% to about 99% sequence similarity to SEQ ID NO:59.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRQLITSKV ADLYPYWGQGTLVTVSS (SEQ ID NO:60). In some instances, the compound can have an amino acid sequence having at least about 90% to about 99% sequence similarity to SEQ ID NO:60.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRSLITSKV ADLYPYWGQGTLVTVSS (SEQ ID NO:61). In some instances, the compound can have an amino acid sequence having at least about 90% to about 99% sequence similarity to SEQ ID NO:61.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRPEITSKV ADLYPYWGQGTLVTVSS (SEQ ID NO:62). In some instances, the compound can have an amino acid sequence having at least about 90% to about 99% sequence similarity to SEQ ID NO:62.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRPGITSKV ADLYPYWGQGTLVTVSS (SEQ ID NO:63). In some instances, the compound can have an amino acid sequence having at least about 90% to about 99% sequence similarity to SEQ ID NO:63.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRPQITSKV ADLYPYWGQGTLVTVSS (SEQ ID NO:64). In some instances, the compound can have an amino acid sequence having at least about 90% to about 99% sequence similarity to SEQ ID NO:64.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRPTITSKV ADLYPYWGQGTLVTVSS (SEQ ID NO:65). In some instances, the compound can have an amino acid sequence having at least about 90% to about 99% sequence similarity to SEQ ID NO:65.

Alternatively, a compound is provided that includes an amino acid sequence of: EVQLLESGGGLVQPGGSLRLS-CAASGRYIDETAVAWFRQAPGKEREFVAGIGGG VDI-TYYADSVKGRFTISRDNSKNTLYLQMNSLRPED-TAVYYCAARPGRPLITEKV ADLYPYWGQGTLVTVSS (SEQ ID NO:66). In some instances, the compound can have an amino acid sequence having at least about 90% to about 99% sequence similarity to SEQ ID NO:66.

An advantage of the RLN analogs herein is that they can be chemically or recombinantly synthesized as a single-chain polypeptide (i.e., monomeric) and thus do not require endoproteolytic processing for biological activity. It is contemplated, however, that in some instances, the VHH moiety can be conjugated not only to single-chain RLNs but also to two-chain RLNs (e.g., native). On the VHH moiety, one could conjugate not only to the N- and C-terminus but also to any surface-exposed amino acid of the VHH (with the proviso that such conjugation does not entirely abrogate albumin binding).

An advantage of the RLN analogs herein is that the VHH moieties can be used not only with native A chain and B chain sequences but also with modified sequences thereof. Moreover, the VHH moieties may be further modified to have enhanced or additional functionality via other peptide/protein fusions or small molecules being attached to the VHH moieties.

An advantage of the RLN analogs herein is that the VHH moieties provide an extended duration of action in mammals such as humans and can have a t½ of about 20 days to about 30 days, thereby allowing for at least weekly or biweekly administration when compared to native, human RLN, especially native, human RLN2 (SEQ ID NOS:5 and 6), which can improve compliance.

An advantage of the RLN analogs herein is that they have similar or better selectivity, affinity and/or potency for RXFP1 than RXFP2 receptors when compared to native, human RLN2 (SEQ ID NOS:5 and 6). Alternatively stated, the RLN analogs herein result in sufficient activity at RXFP1 receptor and reduced or insufficient activity at one or more of the RXFP2, RXFP3 and RXFP4 receptors.

An advantage of the RLN analogs herein is that they have tunable pharmacokinetics achieved by changing albumin affinity of the VHH moieties.

An advantage of the RLN analogs herein is that they have improved stability in a preserved formulation when compared to native, human RLN2 (SEQ ID NOS:5 and 6) or RLN analogs having an Fc fusion.

Moreover, an advantage of the VHH moieties is that they have equal binding not only to human serum albumin but also to dog, monkey, mouse, pig and rat serum albumin, which allows for pharmacodynamic, pharmacokinetic and toxicology studies to more readily translate from these species to humans.

An advantage of the VHH moieties is that they not only can be used to improve the t½ of the RLN analogs herein when compared to native, human RLN2 (SEQ ID NOS:5 and 6) but also can be used to improve the t½ of other biologically active peptides and proteins such as, for example, insulin, growth differentiation factor 15 (GDF-15) or glucose-dependent insulinotropic peptide 1 (GLP-1).

Unless defined otherwise, all technical and scientific terms used herein have the same meaning as commonly understood by one of skill in the art to which the disclosure pertains. Although any methods and materials similar to or equivalent to those described herein can be used in the practice or testing of the RLN analogs, pharmaceutical compositions and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Definitions

As used herein, "about" means within a statistically meaningful range of a value or values such as, for example, a stated concentration, length, molecular weight, pH, sequence similarity, time frame, temperature, volume, etc. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, and in reference to one or more of the RXFP receptors, "activity," "activate," "activating" and the like means a capacity of a compound, such as a RLN analog herein, to bind to and induce a response at its receptor(s), as measured using assays known in the art, such as the in vitro assays described below.

As used herein, "amino acid" means a molecule that, from a chemical standpoint, is characterized by a presence of one or more amine groups and one or more carboxylic acid groups, and may contain other functional groups. As is known in the art, there is a set of twenty amino acids that are designated as standard amino acids and that can be used as building blocks for most of the peptides/proteins produced by any living being. The amino acid sequences in the disclosure contain the standard single letter or three letter codes for the twenty standard amino acids.

As used herein, "analog" means a compound, such as a synthetic peptide or polypeptide, that activates a target receptor and that elicits at least one in vivo or in vitro effect elicited by a native agonist for that receptor.

As used herein, "conservative substitution" means a variant of a reference peptide or polypeptide that is identical to the reference molecule, except for having one or more conservative amino acid substitutions in its amino acid sequence. In general, a conservatively modified variant includes an amino acid sequence that is at least about 70%, 75%, 80%, 85%, 90%, 91%, 92%, 93%, 94%, 95%, 96%, 97%, 98% or 99% identical to a reference amino acid sequence. More specifically, a conservative substitution refers to substitution of an amino acid with an amino acid having similar characteristics (e.g., charge, side-chain size, hydrophobicity/hydrophilicity, backbone conformation and rigidity, etc.) and having minimal impact on the biological activity of the resulting substituted peptide or polypeptide. Conservative substitutions of functionally similar amino acids are well known in the art and thus need not be exhaustively described herein.

As used herein, "effective amount" means an amount or dose of one or more RLN analogs herein, or a pharmaceutically acceptable salt thereof that, upon single or multiple dose administration to an individual in need thereof, provides a desired effect in such an individual under diagnosis or treatment (i.e., may produce a clinically measurable difference in a condition of the individual such as, for example, increased angiogenesis, increased vascular compliance, increased cardiac blood flow, increased hepatic blood flow, increased pulmonary blood flow, increased renal blood flow, increased glomerular filtration rate, decreased blood pressure, decreased (or prevented) inflammation and/or reduced (or prevented) fibrosis in the heart, kidney, liver or lung). An effective amount can be readily determined by one of skill in the art by using known techniques and by observing results obtained under analogous circumstances. In determining the effective amount for an individual, a number of factors are considered, including, but not limited to, the species of mammal, its size, age and general health, the specific disease or disorder involved, the degree of or involvement or the severity of the disease or disorder, the response of the individual, the particular RLN analog administered, the mode of administration, the bioavailability characteristics of the preparation administered, the dose regimen selected, the use of concomitant medication, and other relevant circumstances.

As used herein, "extended duration of action" means that binding affinity and activity for a RLN analog herein continues for a period of time greater than a native RLN, especially native, human RLN2 (SEQ ID NOS:5 and 6), allowing for dosing at least as infrequently as once daily or even thrice-weekly, twice-weekly or once-weekly. The time action profile of the RLN analog may be measured using known pharmacokinetic test methods such as those utilized in the Examples below.

As used herein, "half-life" or "t½" means a time it takes for one-half of a quantity of a compound, such as native RLN or a RLN analog herein, to be removed from a fluid or other physiological space such as serum or plasma of an individual by biological processes. Alternatively, t½ also can mean a time it takes for a quantity of such a compound to lose one-half of its pharmacological, physiological or radiological activity.

As used herein, "half-maximal effective concentration" or "$EC_{50}$" means a concentration of compound that results in 50% activation/stimulation of an assay endpoint, such as a dose-response curve (e.g., cAMP, PI3K-Akt, NFκβ, VEGF and/or nitric oxide (NO) signaling pathways).

As used herein, "in combination with" means administering at least one of the RLN analogs herein either simultaneously, sequentially or in a single combined formulation with one or more additional therapeutic agents.

As used herein, "individual in need thereof" means a mammal, such as a human, with a condition, disease, disorder or symptom requiring treatment or therapy, including for example, those listed herein. In particular, the individual to be treated is a human.

As used herein, "long-acting" means that binding affinity and activity of a RLN analog herein continues for a period of time greater than native, human RLN2 (SEQ ID NOS:5 and 6), allowing for dosing at least as infrequently as once daily or even thrice-weekly, twice-weekly, once-weekly or monthly. The time action profile of the RLN analogs may be measured using known pharmacokinetic test methods such as those described in the Examples below.

As used herein, "non-standard amino acid" means an amino acid that may occur naturally in cells but does not participate in peptide synthesis. Non-standard amino acids can be constituents of a peptide and often are generated by modifying standard amino acids in the peptide (i.e., via post-translational modification). Non-standard amino acids can include D-amino acids, which have an opposite absolute chirality of the standard amino acids above.

As used herein, "pharmaceutically acceptable buffer" means any of the standard pharmaceutical buffers known to one of skill in the art.

As used herein, "RLN" means a relaxin obtained or derived from any species, such as a mammalian species, especially a human, where the native form is a heterodimeric peptide having two peptide chains (e.g., an A chain and a B chain) connected via two disulfide bonds, and with the A chain further having a single intramolecular disulfide bond. RLN includes both native RLN (i.e., full-length) and variations thereof (i.e., additions, deletions, insertions and/or substitutions of native RLN). In humans, there are three native RLN isoforms—RLN1, RLN2 and RLN3. RLN processing begins with preprorelaxin, which is processed to prorelaxin (includes A chain, B chain and C peptide; native RLN has a structure of B-C-A), where the sequence of native, human proRLN1 is set forth in SEQ ID NO:1 (see also, UniProt/SwissProt Database Accession No. P04808), the sequence of native, human proRLN2 is set forth in SEQ ID NO:4 (see also, UniProt/SwissProt Database Accession No. P04090), and the sequence of native, human proRLN3 is set forth in SEQ ID NO:7 (see also, UniProt/SwissProt Database Accession No. Q8WXF3). Prorelaxin undergoes further processing in which the C peptide is cleaved to arrive at RLN. The sequences for the A chain of native, human RLN1, RLN2 and RLN3 are set forth in SEQ ID NOS:2, 5 and 8, respectively. Likewise, the sequences for the B chain of native, human RLN1, RLN2 and RLN3 are set forth in SEQ ID NOS:3, 6 and 9, respectively.

In humans, there are four RLN receptors—RXFP1 (SEQ ID NO:40; see also, UniProt/SwissProt Database Accession No. Q9HBX9), RXFP2 (SEQ ID NO:41; see also, UniProt/SwissProt Database Accession No. Q8WXD0), RXFP3 (SEQ ID NO:42; see also, UniProt/SwissProt Database Accession No. Q9NSD7) and RXFP4 (SEQ ID NO:43; see also, UniProt/SwissProt Database Accession No. Q8TDU9)—that act as GPCRs (see, Halls et al. (2007) Br. J. Pharmacol. 150:677-691). Of interest herein are the RXFP1 and RXFP2 receptors, both of which can bind RLN1 and RLN2. The RXFP1 receptor has been found in the brain, blood cells, bone, heart, kidney, lung, liver and vasculature, whereas the RXFP2 receptor is much more restricted and has been found in the bone and gubernaculum. Stimulation of the RXFP1 and RXFP2 receptors activates signal transduction networks involving adenylate cyclase, protein kinase A, protein kinase C, phosphatidylinositol 3-kinase and/or extracellular signal-regulated kinases (Erk1/2).

As used herein, "RLN analog" and the like means a compound, such as a peptide or polypeptide, that elicits one or more effects of native RLN at one or more RXFP receptors but varies in some manner with respect to the amino acid sequence when compared native RLN. RLN analog also can include variants of these compounds, which are functionally equivalent to RLN but have sequences that are fragments or are the complete sequence but having additions, deletions, insertions and/or substitutions. All references to amino acid positions in unmodified or modified RLNs described herein are based on the corresponding position in the A chain of SEQ ID NO:5 or the B chain of SEQ ID NO:6 of native, human RLN2, unless otherwise specified. In some instances, the RLN analogs herein can bind to a RXFP with higher or lower affinity but demonstrate a longer t½ in vivo or in vitro when compared to native RLN, especially a native, human RLN2 (SEQ ID NOS:5 and 6). In this manner, the RLN analogs herein are synthetic compounds that act as RXFP receptor agonists.

As used herein, "sequence similarity" means a quantitative property of two or more nucleic acid sequences or amino acid sequences of biological compounds such as, for example, a correspondence over an entire length or a comparison window of the two or more sequences. Sequence similarity can be measured by (1) percent identity or (2) percent similarity. Percent identity measures a percentage of residues identical between two biological compounds divided by the length of the shortest sequence; whereas percent similarity measures identities and, in addition, includes sequence gaps and residue similarity in the evaluation. Methods of and algorithms for determining sequence similarity are well known in the art and thus need not be exhaustively described herein. A specified percentage of identical nucleotide or amino acid positions is at least about 75%, 80%, 85%, 86%, 87%, 88%, 89%, 90%, 91%, 92%, 93%, 94%, 95%, 96%, 97%, 98%, 99% or higher.

As used herein, "single-chain relaxin," "scRLN" and the like means a RLN polypeptide where the A and B chains are connected to one another by a linker (i.e., $L_2$) as in A-$L_2$-B or B-$L_2$-A. Moreover, scRLN can include at least one of the native interchain and/or intrachain disulfide bonds to maintain correct structural folding.

As used herein, "two-chain relaxin," "tcRLN" and the like means a RLN polypeptide where the A and B chains are connected to one another by one or more interchain and/or intrachain disulfide bonds, but not by any linkers, to maintain correct structural folding, such as a native RLN.

As used herein, "treating" or "to treat" means managing and caring for an individual having a condition, disease, disorder or symptom for which RLN analog administration is indicated for the purpose of attenuating, restraining, reversing, slowing or stopping progression or severity of the condition, disease, disorder and/or symptom. Treating includes administering a RLN analog herein or composition containing a RLN analog herein to the individual to prevent the onset of symptoms or complications, alleviating the symptoms or complications, or eliminating the condition, disease, disorder or symptom. Treating includes administering a RLN analog or composition containing a RLN analog herein to the individual to result in such as, for example, increased angiogenesis, increased vascular compliance, increased cardiac blood flow, increased hepatic blood flow, increased pulmonary blood flow, increased renal blood flow, increased glomerular filtration rate, decreased blood pressure, decreased (or prevented) inflammation and/or reduced (or prevented) fibrosis in the heart, kidney, liver or lung). The individual to be treated is a mammal, especially a human.

As used herein, "individual," "patient" and "subject" are used interchangeably and mean a mammal, especially a human. In certain instances, the individual is further characterized with a condition, disease, disorder and/or symptom that would benefit from administering a RLN analog herein.

As used herein, "VHH" or "VHH moiety" means a form of single-domain antibody, especially an antibody fragment of a single, monomeric variable region of a heavy chain only antibody (HcAb), which has a very small size of about 15 kDa. It has been found herein that VHH moieties can be used as a pharmacokinetic enhancer to extend the duration of action of and/or to improve the t½ of the RLN analogs herein. The VHH moieties herein bind serum albumin; however, the VHH moieties can be used to bind IgG (including Fc domain), neonatal Fc receptor (FcRn) or other long-lasting serum proteins. Although the VHH moieties herein are used to improve the t½ of RLN, they likewise can be used to improve the t½ of other biologically active peptides/proteins such as, for example, insulin, GDF-15 or GLP-1.

Certain abbreviations are defined as follows: "ACR" refers to urine albumin/urine creatinine ratio; "amu" refers to atomic mass unit; "AUC" refers to area under the curve; "Boc" refers to tert-butoxycarbonyl; "cAMP" refers to cyclic adenosine monophosphate; "CMV" refers to cytomegalovirus; "CV" refers to column volume; "DNA" refers to deoxyribonucleic acid; "DMF" refers to dimethylformamide; "DMSO" refers to dimethyl sulfoxide; "EDC" refers to 1-ethyl-3-(3-dimethylaminopropyl) carbodiimide hydrochloride; "EDTA" refers to ethylenediaminetetraacetic acid; "EIA/RIA" refers to enzyme immunoassay/radioimmunoassay; "ETA" refers to ethanolamine; "GS" refers to glutamine synthetase; "HIC" refers to hydrophobic interaction chromatography; "hr" refers to hour or hours; "HTRF" refers to homogenous time-resolved fluorescent; "IV" refers to intravenous; "IP" refers to intraperitoneal; "kDa" refers to kilodaltons; "LC/MS" refers to liquid chromatography-mass spectrometry; "min" refers to minute or minutes; "MS" refers to mass spectrometry; "MSX" refers to methionine sulfoximine; "NaOAc" refers to sodium acetate; "NHS" refers to N-hydroxysuccinimide; "OtBu" refers to O-tert-butyl; "Pbf" refers to NG-2,2,4,6,7-pentamethyldihydrobenzofuran-5-sulfonyl; "PEI" refers to polyethylenimine; "RP-HPLC" refers to reversed-phase high performance liquid chromatography; "RU" means resonance units; "sec" refers to second or seconds; "SPR" refers to surface plasmon resonance; "SQ" refers to subcutaneous; "SEC" refers to size-exclusion chromatography; "SEM" refers to standard error of the mean; "TFA" refers to trifluoroacetic acid; and "Trt" refers to trityl.

RLN Analogs

The RLN analogs herein have structural similarities to, but many structural differences, from native, human RLN. For example, when compared to native, human RLN2 (SEQ ID NOS:5 and 6), the RLN analogs lack one or more of the amino acids present in native, human RLN2, include a peptide linker between the A chain and the B chain, and include an albumin-binding VHH moiety. The RLN analogs result in sufficient activity at the RXFP1 receptor and reduced or insufficient activity at one or more of the RXFP2, RXFP3 and RXFP4 receptors. Likewise, the RLN analogs have beneficial attributes relevant to their developability as therapeutic treatments, including improved solubility in aqueous solutions, improved chemical and physical formulation stability, extended pharmacokinetic profile (which can be tuned based upon VHH affinity to serum albumin), and/or minimized potential for immunogenicity.

Briefly, the RLN analogs herein include an amino acid sequence from the N-terminus to the C-terminus having one of the following structures:

VHH-$L_1$-A-$L_2$-B,

VHH-$L_1$-B-$L_2$-A,

A-$L_2$-B-$L_1$-VHH, or

B-$L_2$-A-$L_1$-VHH, where VHH is a moiety acting as a pharmacokinetic enhancer, A is a RLN A chain, B is a RLN B chain, $L_1$ is a first peptide linker and $L_2$ is a second peptide linker, where $L_1$ and $L_2$ are distinct from one another (i.e., each have an amino acid sequence that is not the same).

With regard to the A chain, it can be a native RLN A chain, such as a native, human RLN1 A chain (SEQ ID NO:2); native, human RLN2 A chain (SEQ ID NO:5); or native, human RLN3 A chain (SEQ ID NO:8). Alternatively, the A chain can be a variant thereof. For example, one A chain variant can have an amino acid sequence that lacks residues 1 to 4 of SEQ ID NO:5 (i.e., des1-4 human RLN2 A chain or desA1-4).

Likewise, and with regard to the B chain, it can be a native RLN B chain, such as a native, human RLN1 B chain (SEQ ID NO:3); native, human RLN2 B chain (SEQ ID NO:6); or native, human RLN3 B chain (SEQ ID NO:9). Alternatively, the B chain can be a variant thereof. For example, one B chain variant can have an amino acid sequence that lacks residue 1 of SEQ ID NO:6 (i.e., des1 human RLN2 B chain or desB1).

In some instances, the A chain can be a native, human RLN1 A chain (SEQ ID NO:2) and the B chain can be a native, human RLN1 B chain (SEQ ID NO:3); the A chain can be a native, human RLN2 A chain (SEQ ID NO:5) and the B chain can be a native, human RLN2 B chain (SEQ ID NO:6); the A chain can be a native, human RLN3 A chain (SEQ ID NO:8) and the B chain can be a native, human RLN3 B chain (SEQ ID NO:9); the A chain can be a native, human RLN1 A chain (SEQ ID NO:2) and the B chain can be a native, human RLN2 B chain (SEQ ID NO:6); the A chain can be a native, human RLN1 A chain (SEQ ID NO:2) and the B chain can be a native, human RLN3 B chain (SEQ ID NO:9); the A chain can be a native, human RLN2 A chain (SEQ ID NO:5) and the B chain can be a native, human RLN1 B chain (SEQ ID NO:3); the A chain can be a native, human RLN2 A chain (SEQ ID NO:5) and the B chain can be a native, human RLN3 B chain (SEQ ID NO:9); the A chain can be a native, human RLN3 A chain (SEQ ID NO:8) and the B chain can be a native, human RLN1 B chain (SEQ ID NO:3); or the A chain can be a native, human RLN3 A chain (SEQ ID NO:8) and the B chain can be a native, human RLN2 B chain (SEQ ID NO:6).

In some instances, the A chain may be a RLN2 A chain variant that lacks residues 1 to 4 (desA1-4) and the B chain may be any native B chain. In other instances, the A chain may be any native A chain and the B chain may be a RLN2 B chain variant that lacks residue 1 (desB1). In yet other instances, the A chain may be a RLN2 A chain variant that lacks residues 1 to 4 (desA1-4) and the B chain may be a RLN2 B chain variant that lacks residue 1 (desB1). In certain instances, the A chain is the desA1-4 variant. In certain instances, the B chain is the desB1 variant.

Other A and B chains that can be used in the RLN analogs herein are described in, for example, Intl. Patent Application Publication Nos. WO 2018/148419, WO 2018/138170, WO 2017/201340, WO 2016/149501, WO 2015/157829, WO 2015/067791, WO 2015/067113, WO 2014/102179, WO 2013/177529, WO 2013/007563, WO 2013/004607, WO 2012/031326 and WO 2012/024452; and US Patent Application Publication No. US 2011/0243942. See also, Chan et al. (2012) *J. Biol. Chem.* 287:41152-41164; Claasz et al. (2002) *Eur. J. Biochem.* 269:6287-6293; Hossain et al. (2015) *Org. Biomol. Chem.* 13:10895-10890; Hossain et al. (2016) *Chem. Sci.* 7:3805-3819; Park et al. (2008) *J. Biol. Chem.* 283:32099-32109 and Wilkinson et al. (2005) *BMC Evol. Biol.* 5:14.

With regard to $L_1$, it can be a peptide of about 1 amino acid to about 50 amino acids. Alternatively, $L_1$ can be from about 1, about 5, about 10, about 15, about 20, about 25, about 30, about 35, about 40, about 45 or about 50 amino acids. Alternatively still, $L_1$ can be from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids. In some instances, $L_1$ may be omitted such that the A chain or B chain is directly conjugated to the VHH moiety. In some instances, $L_1$ can include a repeating sequence of (GGGGQ)$_n$ (SEQ ID NO:14), where n can be from about 1 to about 10, especially 5 (i.e., (GGGGQ)$_5$; SEQ ID NO:19). In other instances, $L_1$ can include a repeating sequence of (PGPQ)$_n$ (SEQ ID NO:17), where n can be from about 1 to about 10, especially 8 (i.e., (PGPQ)$_8$; SEQ ID NO:20). In still other instances, $L_1$ can include a repeating sequence of (PGPA)$_n$ (SEQ ID NO:18), where n can be from about 1 to about 10, especially 8 (i.e., (PGPA)$_8$; SEQ ID NO:21).

Other linkers that can be used in the RLN analogs as $L_1$ include, but are not limited to, (GGGQ)$_n$ (SEQ ID NO:15) or (GGGGS)$_n$ (SEQ ID NO:16).

With regard to $L_2$, it can be a peptide of about 1 amino acid to about 15 amino acids. Alternatively, $L_2$ can be about 1, about 2, about 3, about 4, about 5, about 6, about 7, about 8, about 9, about 10, about 11, about 12, about 13, about 14, or about 15 amino acids. Alternatively still, $L_2$ can be about 1 amino acid to about 5 amino acids, about 5 amino acids to about 10 amino acids, about 10 amino acids to about 15 amino acids, especially 10 amino acids to 15 amino acids. In some instances, $L_2$ can include a mix of Ala/A, Gln/Q, Gly/G, Pro/P and Ser/S residues. In other instances, $L_2$ can be SEQ ID NO:22, 23 or 67.

With regard to VHH, it can be a polypeptide of about 50 amino acids to about 200 amino acids, especially about 125 amino acids to about 150 amino acids that can bind serum albumin or another serum protein having a long t½. In some instances, VHH can be any one of SEQ ID NOS:10 to 13. Alternatively, VHH can be any one of SEQ ID NOS:45-66. The structural features of these VHH moieties result in RLN analogs having a longer t½ when compared to a native RLN, especially native, human RLN2 (SEQ ID NOS:5 and 6). Given that the VHH moieties herein target serum albumin, the t½ of the RLN analog therefore can be expected to be similar to that of serum albumin of the species to which the RLN analog is administered (taking into account any target mediated drug disposition).

In addition to the changes described in the disclosure, the RLN analogs herein may include one or more additional amino acid modifications, especially conservative substitutions, provided, however, that the RLN analogs remain capable of binding to and activating the RXFP1 receptor.

Taken together, exemplary RLN analogs are as follows:

RLN Analog 1, which includes a VHH moiety (underlined), a (G4Q)$_5$ $L_1$ (italicized), an A chain of RLN2, a $L_2$ of ten residues (bolded) and a B chain (desB1) of RLN2, has the following amino acid sequence: EVQLLESGGGLVQPGGSLRLSCAASGRYIDETAVAWFRQAPGKEREFVAGIGGG VDITYYADSVKGRFTISRDNSKNTLYLQMNSLRPEDTAVYYCAARPGRPLITSKV ADLYPYWGQGTLVTVSSGGGGQGGGGQGGGGQGGGGQ GGGGQQLYSALANK CCHVGCTKRSLARFCGGGSGGSGGGSWMEEVIKLCGRELVRAQIAICGMSTWS (SEQ ID NO:24), or a pharmaceutically acceptable salt thereof;

RLN Analog 2, which includes a VHH moiety (underlined), a (PGPA)$_8$ $L_1$ (italicized) an A chain of RLN2, a $L_2$ of ten residues (bolded) and a B chain (desB1) of RLN2, has the following amino acid sequence: EVQLLESGGGLVQPGGSLRLSCAASGRYIDETAVAWFRQAPGKEREFVAGIGGG VDITYYADSVKGRFTISRDNSKNTLYLQMNSLRPEDTAVYYCAARPGRPLITSKV ADLYPYWGQGTLVTVSSPGPAPGPAPGPAPGPAPGPAPGPA PGPAPGPAQLYSAL ANKCCHVGCTKRSLARFCGGGSGGSGGGSWMEEVIKLCGRELVRAQIAICGMS TWS (SEQ ID NO:25), or a pharmaceutically acceptable salt thereof;

RLN Analog 3, which includes a VHH moiety (underlined), a (G4Q)$_5$ $L_1$ (italicized), a B chain (desB1) of RLN2, a $L_2$ of ten residues (bolded) and an A chain of RLN2, has the following amino acid sequence: EVQLLESGGGLVQPGGSLRLSCAASGRYIDETAVAWFRQAPGKEREFVAGIGGG VDITYYADSVKGRFTISRDNSKNTLYLQMNSLRPEDTAVYYCAARPGRPLITSKV ADLYPYWGQGTLVTVSSGGGGQGGGGQGGGGQGGGGQG GGGQSWMEEVIKL CGRELVRAQIAICGMSTWSGGGSGGSGGGQLYSALANKCCHVGCTKRSLARFC (SEQ ID NO:26), or a pharmaceutically acceptable salt thereof;

RLN Analog 4, which includes a VHH moiety (underlined), a (PGPQ)$_8$ $L_1$ (italicized), a B chain (desB1) of RLN2, a $L_2$ of ten residues (bolded) and an A chain of RLN2, has the following amino acid sequence: EVQLLESGGGLVQPGGSLRLSCAASGRYIDETAVAWFRQAPGKEREFVAGIGGG VDITYYADSVKGRFTISRDNSKNTLYLQMNSLRPEDTAVYYCAARPGRPLITSKV ADLYPYWGQGTLVTVSSPGPQPGPQPGPQPGPQPGPQPGP QPGPQPGPQSWME EVIKLCGRELVRAQIAICGMSTWSGGGSGGSGGGQLYSALANKCCHVGCTKRS LARFC (SEQ ID NO:27), or a pharmaceutically acceptable salt thereof;

RLN Analog 5, which includes a B chain (desB1) of RLN2, a $L_2$ of ten residues (bolded), an A chain of RLN2, a (G4Q)$_5$ $L_1$ (italicized) and a VHH moiety (underlined), has the following amino acid sequence: SWMEEVIKLCGRELVRAQIAICGMSTWSGGGSGGSGGGQLYSALANKCCHVGC TKRSLARFCGGGGQGGGGQGGGGQGGGGQGGGG QEVQLLESGGGLVQPGGSL RLSCAASGRYIDETAVAWFRQAPGKEREFVAGIGGGVDITYYADSVKGRFTISRD NSKNTLYLQMNSLRPEDTAVYYCAARPGRPLITSKVADLYPYWGQGTLVTVSSP P (SEQ ID NO:28), or a pharmaceutically acceptable salt thereof;

RLN Analog 6, which includes a B chain (desB1) of RLN2, a $L_2$ of ten residues (bolded), an A chain of RLN2, a (PGPQ)$_8$ $L_1$ (italicized) and a VHH moiety (underlined), has the following amino acid sequence: SWMEEVIKLCGRELVRAQIAICGMSTWSGGGSGGSGGGQLYSALANKCCHVGC TKRSLARFCPGPQPGPQPGPQPGPQPGPQPGPQPGPQPGPQ PGPQEVQLLESGGGLVQ PGGSLRLSCAASGRYIDETAVAWFRQAPGKEREFVAGIGGGVDITYYADSVKGR FTISRDNSKNTLYLQMNSLRPEDTAVYYCAARPGRPLITSKVADLYPYWGQGTL VTVSSPP (SEQ ID NO:29), or a pharmaceutically acceptable salt thereof;

RLN Analog 7, which includes a VHH moiety (underlined), a (G4Q)$_5$ $L_1$ (italicized), a B chain (desB1) of RLN2, a $L_2$ of ten residues (bolded) and an A chain of RLN2, has the following amino acids sequence: EVQLLESGGGLVQPGGSLRLSCAASGRYIDETAVAWFRQAPGKREFVAGIGGG VDITYYADSVKGRFTISRDNSKNTLYLQMNSLRPEDTAVYYCAARPGRPLITSKV ADLYPYWGQGTLVTVSSGGGGQGGGGQGGGGQGGGGQ GGGQSWMEEVIKL CGRELVRAQIA-
ICGMSTWSGGGSGGSGGGGQLYSALANKC-
CHVGCTKRSLARFC (SEQ ID NO:30), or a pharmaceutically acceptable salt thereof;

RLN Analog 8, which includes a VHH moiety (underlined), a (PGPQ)$_8$-L$_1$ (italicized), a B chain (desB1) of RLN2, a L$_2$ of ten residues (bolded) and an A chain of RLN2, has the following amino acid sequence: EVQLLESGGGLVQPGGSLRLSCAASGRYIDETA-VAWFRQAPGKGREFVAGIGGG VDITYY-ADSVKGRFTISRDNSKNTLYLQMNSLRPEDTAVYY-CAARPGRPLITSKV ADLY-PYWGQGTLVTVSSPGPQPGPQPGPQPGPQPGPQPGP QPGPQPGPQSWME EVIKLCGRELVRAQIA-ICGMSTWSGGGSGGSGGGQLYSALANKC-CHVGCTKRS LARFC (SEQ ID NO:31), or a pharmaceutically acceptable salt thereof;

RLN Analog 9, which includes a B chain (desB1) of RLN2, a L$_2$ of ten residues (bolded), an A chain of RLN2, a (G4Q)$_5$ L$_1$ (italicized) and a VHH moiety (underlined), has the following amino acid sequence: SWMEEVIKLCGREL-VRAQIAICGMSTWSGGGSGGSGGGQLYSALANKC-CHVGC TKRSLARFCGGGGQGGGGQGGGGQGGGGQGGGG QEVQLLESGGGLVQPGGSL RLSCAASGRYIDETA-VAWFRQAPGKGREFVAGIGGGVDITYY-ADSVKGRFTISRD NSKNTLYLQMNSLRPEDTAVYY-CAARPGRPLITSKVADLYPYWGQGTLVTVSSP P (SEQ ID NO:32), or a pharmaceutically acceptable salt thereof;

RLN Analog 10, which includes a B chain (desB1) of RLN2, a L$_2$ of ten residues (bolded), an A chain of RLN2, a (PGPQ)$_8$ L$_1$ (italicized) and a VHH moiety (underlined), has the following amino acid sequence: SWMEE-VIKLCGRELVRAQIA-ICGMSTWSGGGSGGSGGGQLYSALANKCCHVGC TKRSLARFCPGPQPGPQPGPQPGPQPGPQPGPQPGP QPGPQEVQLLESGGGLVQ PGGSLRLSCAASGRYIDE-TAVAWFRQAPGKGREFVAGIGGGVDITYYADSVKGR FTISRDNSKNTLYLQMNSLRPEDTAVYYCAARPGR-PLITSKVADLYPYWGQGTL VTVSSPP (SEQ ID NO:33), or a pharmaceutically acceptable salt thereof;

RLN Analog 11, which includes a VHH moiety (underlined), a (G4Q)$_5$ L$_1$ (italicized), a B chain (desB1) of RLN2, a L$_2$ of thirteen residues (bolded) and an A chain (desA1-4) of RLN2, has the following amino acid sequence: EVQLLESGGGLVQPGGSLRLSCAASGRYIDETA-VAWFRQAPGKEREFVAGIGGG VDITYY-ADSVKGRFTISRDNSKNTLYLQMNSLRPEDTAVYY-CAARPGRPLITSKV ADLY-PYWGQGTLVTVSSGGGGQGGGGQGGGGQGGGGQ GGGGQSWMEEVI KLCGRELVRAQIA-ICGMSTWSGGGSGGSGGSGGGALANKC-CHVGCTKRSLARF C (SEQ ID NO:34), or a pharmaceutically acceptable salt thereof;

RLN Analog 12, which includes a VHH moiety (underlined), a (G4Q)$_5$ L$_1$ (italicized), a B chain (desB1) of RLN2, a L$_2$ of thirteen residues (bolded) and an A chain (desA1-4) of RLN2, has the following amino acid sequence: EVQLLESGGGLVQPGGSLRLSCAASGRYIDETA-VAWFRQAPGKGREFVAGIGGG VDITYY-ADSVKGRFTISRDNSKNTLYLQMNSLRPEDTAVYY-CAARPGRPLITSKV ADLY-PYWGQGTLVTVSSGGGGQGGGGQGGGGQGGGGQ GGGGQSWMEEVIKL CGRELVRAQIA-ICGMSTWSGGGSGGSGGSGGGALANKC-CHVGCTKRSLARFC (SEQ ID NO:35), or a pharmaceutically acceptable salt thereof;

RLN Analog 13, which includes a VHH moiety (underlined), a (G4Q)$_5$ L$_1$ (italicized), an A chain (desA1-4) of RLN2, a L$_2$ of ten residues (bolded) and a B chain (desB1) of RLN2, has the following amino acid sequence: EVQLLESGGGLVQPGGSLRLSCAASGRYIDETA-VAWFRQAPGKGREFVAGIGGG VDITYY-ADSVKGRFTISRDNSKNTLYLQMNSLRPEDTAVYY-CAARPGRPLITSKV ADLY-PYWGQGTLVTVSSGGGGQGGGGQGGGGQGGGGQ GGGGQALANKCCHV GCTKRSLARFCGGGSGGSGGGSWMEEVIKLCGREL-VRAQIAICGMSTWS (SEQ ID NO:36), or a pharmaceutically acceptable salt thereof;

RLN Analog 14, which includes a VHH moiety (underlined), a (PGPQ)$_8$ L$_1$ (italicized), an A chain (desA1-4) of RLN2, a L$_2$ of ten residues (bolded) and a B chain (desB1) of RLN2, has the following amino acid sequence: EVQLLESGGGLVQPGGSLRLSCAASGRYIDETA-VAWFRQAPGKGREFVAGIGGG VDITYY-ADSVKGRFTISRDNSKNTLYLQMNSLRPEDTAVYY-CAARPGRPLITSKV ADLY-PYWGQGTLVTVSSPGPQPGPQPGPQPGPQPGPQPGP QPGPQPGPQALAN KCCHVGCTKRSLARFCGGGSGGSGGGSWMEE-VIKLCGRELVRAQIAICGMSTW S (SEQ ID NO:37), or a pharmaceutically acceptable salt thereof;

RLN Analog 15, which includes a VHH moiety (underlined), a (G4Q)$_5$ L$_1$ (italicized), a B chain (native) of RLN2, a L$_2$ of ten residues (bolded) and an A chain (native) of RLN2, has the following amino acid sequence: EVQLLESGGGLVQPGGSLRLSCAASGRYIDETA-VAWFRQAPGKEREFVAGIGGG VDITYY-ADSVKGRFTISRDNSKNTLYLQMNSLRPEDTAVYY-CAARPGRPLITSKV ADLY-PYWGQGTLVTVSSGGGGQGGGGQGGGGQGGGGQ GGGGQDSWMEEVIK LCGRELVRAQIA-ICGMSTWSSGGGSGGGGQLYSALANKC-CHVGCTKRSLARF C (SEQ ID NO:38), or a pharmaceutically acceptable salt thereof; and RLN Analog 16, which includes a VHH moiety (underlined), a (PGPA)$_8$ L$_1$ (italicized), a B chain (native) of RLN2, a L$_2$ of ten residues (bolded) and an A chain (native) of RLN2, has the following amino acid sequence: EVQLLESGGGLVQPGGSLRLSCAASGRYIDETA-VAWFRQAPGKEREFVAGIGGG VDITYY-ADSVKGRFTISRDNSKNTLYLQMNSLRPEDTAVYY-CAARPGRPLITSKV ADLY-PYWGQGTLVTVSSPGPAPGPAPGPAPGPAPGPAPGPA PGPAPGPADSWME EVIKLCGRELVRAQIA-ICGMSTWSSGGGGSGGGGQLYSALANKC-CHVGCTKRS LARFC (SEQ ID NO:39), or a pharmaceutically acceptable salt thereof.

Half-life of the RLN analogs herein may be measured using methods known in the art including, for example, those described in the Examples below. Likewise, affinity of the RLN analogs for albumins of different species may be measured using methods known in the art for measuring binding affinities, for example, those described in the Examples below, and is commonly expressed as the equilibrium dissociation constant ($K_D$) value. Moreover, activity of the RLN analogs at each of the RXFP receptors may be measured using methods known in the art, including, for example, the in vitro activity assays described below, and is commonly expressed as an $EC_{50}$ value.

As a result of the modifications described above, the RLN analogs herein have a t½ that is longer than that of a native RLN, especially native, human RLN2 (SEQ ID NOS:5 and 6) when administered to a mammal, especially a human. As noted above, the VHH moieties herein target serum album; therefore, the t½ of the RLN analogs herein can be expected to be similar to that of serum albumin of the species to which the RLN analog is administered. In some instances, the RLN analogs can have a t½ of about 1 day to about 31 days, of about 5 days to about 25 days, of about 10 days to about 20 days, or even of about 15 days. In other instances, the RLN analogs can have a t½ of about 1 day to about 5 days, of about 6 days to about 10 days, of about 11 days to about 15 days, of about 16 days to about 20 days, of about 21 to about 25 days, or even of about 26 to about 31 days. In other instances, the RLN analogs can have a t½ of about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or even about 31 days. In particular instances, the RLN analogs can have a t½ of about 20 days when administered to a human.

Likewise, the RLN analogs herein have a potency at the RXFP1 receptor within about 10-fold to about 100-fold of, for example, native, human RLN2 (SEQ ID NOS:5 and 6) when administered to a human.

Pharmaceutical Compositions and Kits

The RLN analogs herein can be formulated as pharmaceutical compositions, which can be administered by parenteral routes (e.g., intravenous, intraperitoneal, intramuscular, subcutaneous or transdermal). Such pharmaceutical compositions and techniques for preparing the same are well known in the art. See, e.g., Remington, "The Science and Practice of Pharmacy" (D. B. Troy ed., 21$^{st}$ Ed., Lippincott, Williams & Wilkins, 2006). In particular instances, the RLN analogs are administered SQ or IV. Alternatively, however, the RLN analogs can be formulated in forms for other pharmaceutically acceptable routes such as, for example, tablets or other solids for oral administration; time release capsules, and any other form currently used, including creams, lotions, inhalants and the like.

As noted above, and to improve their in vivo compatibility and effectiveness, the RLN analogs herein may be reacted with any number of inorganic and organic acids/bases to form pharmaceutically acceptable acid/base addition salts. Pharmaceutically acceptable salts and common techniques for preparing them are well known in the art (see, e.g., Stahl et al., "Handbook of Pharmaceutical Salts: Properties, Selection and Use" (2$^{nd}$ Revised Ed. Wiley-VCH, 2011)). Pharmaceutically acceptable salts for use herein include sodium, trifluoroacetate, hydrochloride and acetate salts.

The RLN analogs herein may be administered by a physician or self-administered using an injection. It is understood the gauge size and amount of injection volume can be readily determined by one of skill in the art. However, the amount of injection volume can be ≤about 2 mL or even ≤about 1 mL, and the needle gauge can be ≥about 27 G or even ≥about 29 G.

The disclosure also provides and therefore encompasses novel intermediates and methods useful for synthesizing the RLN analogs herein, or a pharmaceutically acceptable salt thereof. The intermediates and RLN analogs can be prepared by a variety of techniques that are well known in the art. For example, a method using recombinant synthesis is illustrated in the Examples below. The specific steps for each of the techniques described may be combined in different ways to prepare the RLN analogs. The reagents and starting materials are readily available to one of skill in the art.

The RLN analogs herein are generally effective over a wide dosage range. Exemplary doses of the RLN analogs or of pharmaceutical compositions including the same can be milligram (mg) or microgram (m), nanogram (ng), or picogram (pg) amounts per kilogram (kg) of an individual. In this manner, a daily dose can be from about 1 μg to about 100 mg.

Here, the effective amount of the RLN analog in a pharmaceutical composition can be a dose of about 0.25 mg to about 5.0 mg. One of skill in the art, however, understands that in some instances the effective amount (i.e., dose/dosage) may be below the lower limit of the aforesaid range and be more than adequate, while in other cases the effective amount may be a larger dose and may be employed with acceptable side effects.

In addition to the RLN analog herein, the pharmaceutical composition also can include at least one additional therapeutic agent, especially a therapeutic agent typically used as the standard of care in cardiovascular, pulmonary and renal conditions, diseases and disorders.

In this manner, a pharmaceutical composition can include an effective amount of at least one RLN analog herein, a pharmaceutically acceptable carrier and optionally at least one additional therapeutic agent. For example, the pharmaceutical composition can include an effective amount of a RLN analog of SEQ ID NO:24 and a pharmaceutically acceptable carrier, an effective amount of a RLN analog of SEQ ID NO:25 and a pharmaceutically acceptable carrier, an effective amount of a RLN analog of SEQ ID NO:26 and a pharmaceutically acceptable carrier, an effective amount of a RLN analog of SEQ ID NO:27 and a pharmaceutically acceptable carrier, an effective amount of a RLN analog of SEQ ID NO:28 and a pharmaceutically acceptable carrier, an effective amount of a RLN analog of SEQ ID NO:29 and a pharmaceutically acceptable carrier, an effective amount of a RLN analog of SEQ ID NO:30 and a pharmaceutically acceptable carrier, an effective amount of a RLN analog of SEQ ID NO:31 and a pharmaceutically acceptable carrier, an effective amount of a RLN analog of SEQ ID NO:32 and a pharmaceutically acceptable carrier, an effective amount of a RLN analog of SEQ ID NO:33 and a pharmaceutically acceptable carrier, an effective amount of a RLN analog of SEQ ID NO:34 and a pharmaceutically acceptable carrier, an effective amount of a RLN analog of SEQ ID NO:35 and a pharmaceutically acceptable carrier, an effective amount of a RLN analog of SEQ ID NO:36 and a pharmaceutically acceptable carrier, an effective amount of a RLN analog of SEQ ID NO:37 and a pharmaceutically acceptable carrier, an effective amount of a RLN analog of SEQ ID NO:38 and a pharmaceutically acceptable carrier, or an effective amount of a RLN analog of SEQ ID NO:39 and a pharmaceutically acceptable carrier.

Alternatively, the RLN analogs herein can be provided as part of a kit. In some instances, the kit includes a device for administering at least one RLN analog (and optionally at least one additional therapeutic agent) to an individual. In certain instances, the kit includes a syringe and needle for administering the at least one RLN analog (and optionally at least one additional therapeutic agent). In particular instances, the RLN analog (and optionally at least one additional therapeutic agent) is pre-formulated in aqueous solution within the syringe.

Methods of Making and Using the RLN Analogs

The RLN analogs herein can be made via any number of standard recombinant DNA methods or standard chemical peptide synthesis methods known in the art. With regard to recombinant DNA methods, one can use standard recombinant techniques to construct a polynucleotide having a nucleic acid sequence that encodes an amino acid sequence for a RLN analog, incorporate that polynucleotide into recombinant expression vectors, and introduce the vectors into host cells, such as bacteria, yeast and mammalian cells, to produce the RLN analog. See, e.g., Green & Sambrook, "Molecular Cloning: A Laboratory Manual" (Cold Spring Harbor Laboratory Press, $4^{th}$ ed. 2012).

With regard to recombinant DNA methods, the compounds herein can be prepared by producing a protein or precursor protein molecule using recombinant DNA techniques. DNA, including cDNA and synthetic DNA, may be double-stranded or single-stranded, and the coding sequences therein encoding a compound herein may vary as a result of the redundancy or degeneracy of the genetic code. Briefly, the DNA sequences encoding the compounds herein are introduced into a host cell to produce the compound or precursor thereof. The host cells can be bacterial cells such as K12 or B strains of *Escherichia coli*, fungal cells such as yeast cells, or mammalian cells such as Chinese hamster ovary (CHO) cells.

An appropriate host cell is transiently or stably transfected or transformed with an expression system, such as expression vectors, for producing a compound herein or a precursor thereof. Expression vectors typically are replicable in the host organisms either as episomes or as an integral part of the host chromosomal DNA. Commonly, expression vectors will contain selection markers such as, for example, tetracycline, neomycin, G418 and dihydrofolate reductase, to permit selection of those cells transformed with the desired DNA sequences.

The specific biosynthetic or synthetic steps for each of the steps described herein may be used, not used or combined in different ways to prepare the compounds herein.

With regard to chemical peptide synthesis methods, one can use standard manual or automated solid-phase synthesis procedures. For example, automated peptide synthesizers are commercially available from, for example, Applied Biosystems (Foster City, Calif.) and Protein Technologies Inc. (Tucson, Ariz.). Reagents for solid-phase synthesis are readily available from commercial sources. Solid-phase synthesizers can be used according to the manufacturer's instructions for blocking interfering groups, protecting amino acids during reaction, coupling, deprotecting and capping of unreacted amino acids. Additional details on making synthetic RLNs can be found in U.S. Pat. Nos. 4,835,251 and 5,166,191.

One use of the RLN analogs herein is for treating cardiovascular conditions, diseases and/or disorders. Exemplary cardiovascular conditions, diseases and disorders include, but are not limited to, acute heart failure, chronic heart failure, atherosclerosis, coronary artery disease, diabetes, stroke, hypercholesterolemia, hypertension, ischemia, vasoconstriction and ventricular hypertrophy.

Another use of the RLN analogs herein is for treating pulmonary conditions, diseases and/or disorders. Exemplary pulmonary conditions, diseases and disorders include, but are not limited to, pulmonary hypertension and chronic obstructive pulmonary disease (COPD).

Another use of the RLN analogs herein is for treating renal conditions, diseases and/or disorders. Exemplary renal conditions, diseases and disorders include, but are not limited to, chronic kidney disease and diabetes nephropathy.

The methods can include the steps described herein, and these may be be, but not necessarily, carried out in the sequence as described. Other sequences, however, also are conceivable. Moreover, individual or multiple steps may be carried out either in parallel and/or overlapping in time and/or individually or in multiply repeated steps. Furthermore, the methods may include additional, unspecified steps.

Such methods therefore can include selecting an individual having a cardiovascular condition, disease or disorder or who is predisposed to the same. Alternatively, the methods can include selecting an individual having a pulmonary condition, disease or disorder or who is predisposed to the same. Alternatively, the methods can include selecting an individual having a renal condition, disease or disorder or who is predisposed to the same. In certain instances, the methods can include selecting an individual who is diabetic, hypertensive with kidney function impairment and/or obese.

The methods also can include administering to the individual an effective amount of at least one RLN analog herein, which may be in the form of a pharmaceutical composition as also described herein. In some instances, the RLN analog/pharmaceutical composition can include an additional therapeutic agents such as an anticoagulant, an ACE inhibitor, an ARB, an ARNI, a β-blocker, a diuretic, digitalis, digoxin, hydralazine/isorbide dinitrate, a MRA or other aldosterone antagonist, a SGLT2 inhibitor, a statin and/or an anti-glycemic agent, as well as other therapeutic agents to control comorbidities, including, but not limited to, high cholesterol, high blood pressure, atrial fibrillation and diabetes.

The concentration/dose/dosage of the RLN analog and optional additional therapeutic agent are discussed elsewhere herein.

With regard to a route of administration, the RLN analog or pharmaceutical composition including the same can be administered in accord with known methods such as, for example, orally; by injection (i.e., intra-arterially, intravenously, intraperitoneally, intracerebrally, intracerebroventricularly, intramuscularly, intraocularly, intraportally or intralesionally); by sustained release systems, or by implantation devices. In certain instances, the RLN analog or pharmaceutical composition including the same can be administered SQ by bolus injection or continuously.

With regard to a dosing frequency, the RLN analog or pharmaceutical composition including the same can be administered daily, every other day, three times a week, two times a week, one time a week (i.e., weekly), biweekly (i.e., every other week), or monthly. In certain instances, the RLN analog or pharmaceutical composition including the same is administered SQ every other day, SQ three times a week, SQ two times a week, SQ one time a week, SQ every other week or SQ monthly. In particular instances, the RLN analog or pharmaceutical composition including the same is administered SQ one time a week (QW).

With regard to those instances in which the RLN analog or pharmaceutical composition including the same is administered in combination with an effective amount of at least one additional therapeutic agent. The additional therapeutic agent can be administered simultaneously, separately or sequentially with the RLN analog or pharmaceutical composition including the same.

Moreover, the additional therapeutic agent can be administered with a frequency same as the RLN analog or pharmaceutical composition including the same (i.e., every other day, twice a week, or even weekly). Alternatively, the additional therapeutic agent can be administered with a frequency distinct from the RLN analog or pharmaceutical composition including the same. In other instances, the additional therapeutic agent can be administered SQ. In other instances, the additional therapeutic agent can be administered IV. In still other instances, the additional therapeutic agent can be administered orally.

It is further contemplated that the methods may be combined with diet and exercise and/or may be combined with additional therapeutic agents other than those discussed above.

EXAMPLES

The following non-limiting examples are offered for purposes of illustration, not limitation.

Polypeptide Expression

Example 1: Recombinant Expression of RLN Analog 1

Example 1 is a RLN analog having an amino acid sequence of:

```
                                          (SEQ ID NO: 24)
EVQLLESGGGLVQPGGSLRLSCAASGRYIDETAVAWFRQAPGKEREFVAG

IGGGVDITYYADSVKGRFTISRDNSKNTLYLQMNSLRPEDTAVYYCAARP

GRPLITSKVADLYPYWGQGTLVTVSSGGGGQGGGGQGGGGQGGGGQGGGG

QQLYSALANKCCHVGCTKRSLARFCGGGSGGSGGGSWMEEVIKLCGRELV

RAQIAICGMSTWS.
```

Here, the RLN analog of SEQ ID NO:24 is generated in a mammalian cell expression system using CHOK1 cell derivatives. A cDNA sequence encoding SEQ ID NO:24 is sub-cloned into GS-containing expression plasmid backbone (pEE12.4-based plasmids). The cDNA sequence is fused in frame with the coding sequence of a signal peptide sequence, METDTLLLWVLLLWVPGSTG (SEQ ID NO:44), to enhance secretion of the RLN analog into the tissue culture medium. The expression is driven by the viral CMV promoter.

For generating the RLN analog via transient transfection, CHOK1 cells are transfected with the recombinant expression plasmid using a PEI-based method. Briefly, the appropriate volume of CHOK1 suspension cells at a density of $4 \times 10^6$ cells/mL is transferred in shake flasks, and both PEI and recombinant plasmid DNA are added to the cells. Cells are incubated in a suspension culture at 32° C. for 6 days. At the end of the incubation period, cells are removed by low speed centrifugation and the RLN analog protein is purified from the conditioned medium.

Alternatively, and for generating the RLN analog via stable transfections, CHOK1 cells are stably transfected using electroporation and the appropriate amount of recombinant expression plasmid, and the transfected cells are maintained in suspension culture at an adequate cell density. Selection of the transfected cells is accomplished by growth in 25 µM MSX-containing serum-free medium and incubated at about 35° C.-37° C. and about 5%-7% $CO_2$.

The RLN analog is secreted into the media from the CHO cells, which is purified by Protein A affinity chromatography followed by ion exchange and hydrophobic interaction chromatography or size-exclusion chromatography. Specifically, the RLN analog from harvested media is captured onto Mab Select Protein A resin (GE). The resin then is briefly washed with a running buffer, such as a phosphate-buffered saline (PBS; pH 7.4) or a buffer containing Tris, to remove non-specifically bound material. The protein is eluted from the resin with a low pH solution, such as 10 mM citric acid pH 3. Fractions containing the RLN analog are pooled and may be held at a low pH to inactivate potential viruses. The pH may be neutralized by adding a base such as 0.1 M Tris pH 8.0. The RLN analog may be further purified by ion exchange chromatography using resins such as Poros 50 HS (ThermoFisher). The RLN analog is eluted from the column using a 0 to 500 mM NaCl gradient in 20 mM NaOAc, pH 5.0 over 15 column volumes.

The RLN analog may be further purified by hydrophobic interaction chromatography by using a Capto Phenyl ImpRes HIC Column (GE Healthcare). The purification is performed by adjusting the column charge solution to around 0.5 M sodium sulfate and eluting using a 10 CV gradient going from 0.5 M to 0 M sodium sulfate in a 20 mM Tris pH 8 solution. After HIC, the RLN analog may be even further purified by SEC by loading the concentrated Capto Phenyl ImpRes pool on a Superdex200 (GE Healthcare) with isocratic elution in PBS pH 7.4 or in 20 mM histidine, 50 mM NaCl pH 6.0.

Purified RLN analog may be passed through a viral retention filter such as Planova 20N (Asahi Kasei Medical) followed by concentration/diafiltration into 20 mM histidine, 20 mM NaCl pH 6 using tangential flow ultrafiltration on a regenerated cellulose membrane (Millipore).

The RLN analog therefore is prepared in this manner or in a similar manner that would be readily determined by one of skill in the art.

Example 2: Recombinant Expression of RLN Analog 2

Example 2 is a RLN analog having an amino acid sequence of:

```
                                          (SEQ ID NO: 25)
EVQLLESGGGLVQPGGSLRLSCAASGRYIDETAVAWFRQAPGKEREFVAG

IGGGVDITYYADSVKGRFTISRDNSKNTLYLQMNSLRPEDTAVYYCAARP

GRPLITSKVADLYPYWGQGTLVTVSSPGPAPGPAPGPAPGPAPGPAPGPA

PGPAPGPAQLYSALANKCCHVGCTKRSLARFCGGGSGGSGGGSWMEEVIK

LCGRELVRAQIAICGMSTWS.
```

Here, the RLN analog of SEQ ID NO:25 is generated essentially as described for Example 1 except that a cDNA sequence encoding SEQ ID NO:25 is used in the expression plasmid.

Example 3: Recombinant Expression of RLN Analog 3

Example 3 is a RLN analog having an amino acid sequence of:

(SEQ ID NO: 26)
EVQLLESGGGLVQPGGSLRLSCAASGRYIDETAVAWFRQAPGKEREF
VAGIGGGVDITYYADSVKGRFTISRDNSKNTLYLQMNSLRPEDTAVY
YCAARPGRPLITSKVADLYPYWGQGTLVTVSSGGGGQGGGGQGGGGQ
GGGGQGGGGQSWMEEVIKLCGRELVRAQIAICGMSTWSGGGSGGSGG
GQLYSALANKCCHVGCTKRSLARFC.

Here, the RLN analog of SEQ ID NO:26 is generated essentially as described for Example 1 except that a cDNA sequence encoding SEQ ID NO:26 is used in the expression plasmid.

Example 4: Recombinant Expression of RLN Analog 4

Example 4 is a RLN analog having an amino acid sequence of:

(SEQ ID NO: 27)
EVQLLESGGGLVQPGGSLRLSCAASGRYIDETAVAWFRQAPGKEREF
VAGIGGGVDITYYADSVKGRFTISRDNSKNTLYLQMNSLRPEDTAVY
YCAARPGRPLITSKVADLYPYWGQGTLVTVSSPGPQPGPQPGPQPGP
QPGPQPGPQPGPQPGPQSWMEEVIKLCGRELVRAQIAICGMSTWSGG
GSGGSGGGQLYSALANKCCHVGCTKRSLARFC.

Here, the RLN analog of SEQ ID NO:27 is generated essentially as described for Example 1 except that a cDNA sequence encoding SEQ ID NO:27 is used in the expression plasmid.

Example 5: Recombinant Expression of RLN Analog 5

Example 5 is a RLN analog having an amino acid sequence of:

(SEQ ID NO: 28)
SWMEEVIKLCGRELVRAQIAICGMSTWSGGGSGGSGGGQLYSALANK
CCHVGCTKRSLARFCGGGGQGGGGQGGGGQGGGGQGGGGQEVQLLES
GGGLVQPGGSLRLSCAASGRYIDETAVAWFRQAPGKEREFVAGIGGG
VDITYYADSVKGRFTISRDNSKNTLYLQMNSLRPEDTAVYYCAARPG
RPLITSKVADLYPYWGQGTLVTVSSPP.

Here, the RLN analog of SEQ ID NO:28 is generated essentially as described for Example 1 except that a cDNA sequence encoding SEQ ID NO:28 is used in the expression plasmid.

Example 6: Recombinant Expression of RLN Analog 6

Example 6 is a RLN analog having an amino acid sequence of:

(SEQ ID NO: 29)
SWMEEVIKLCGRELVRAQIAICGMSTWSGGGSGGSGGGQLYSALANK
CCHVGCTKRSLARFCPGPQPGPQPGPQPGPQPGPQPGPQPGPQPGPQ
EVQLLESGGGLVQPGGSLRLSCAASGRYIDETAVAWFRQAPGKEREF
VAGIGGGVDITYYADSVKGRFTISRDNSKNTLYLQMNSLRPEDTAVY
YCAARPGRPLITSKVADLYPYWGQGTLVTVSSPP.

Here, the RLN analog of SEQ ID NO:29 is generated essentially as described for Example 1 except that a cDNA sequence encoding SEQ ID NO:29 is used in the expression plasmid.

Example 7: Recombinant Expression of RLN Analog 7

Example 7 is a RLN analog having an amino acid sequence of:

(SEQ ID NO: 30)
EVQLLESGGGLVQPGGSLRLSCAASGRYIDETAVAWFRQAPGKGREF
VAGIGGGVDITYYADSVKGRFTISRDNSKNTLYLQMNSLRPEDTAVY
YCAARPGRPLITSKVADLYPYWGQGTLVTVSSGGGGQGGGGQGGGGQ
GGGGQGGGGQSWMEEVIKLCGRELVRAQIAICGMSTWSGGGSGGSGG
GQLYSALANKCCHVGCTKRSLARFC.

Here, the RLN analog of SEQ ID NO:30 is generated essentially as described for Example 1 except that a cDNA sequence encoding SEQ ID NO:30 is used in the expression plasmid.

Example 8: Recombinant Expression of RLN Analog 8

Example 8 is a RLN analog having an amino acid sequence of:

(SEQ ID NO: 31)
EVQLLESGGGLVQPGGSLRLSCAASGRYIDETAVAWFRQAPGKGREF
VAGIGGGVDITYYADSVKGRFTISRDNSKNTLYLQMNSLRPEDTAVY
YCAARPGRPLITSKVADLYPYWGQGTLVTVSSPGPQPGPQPGPQPGP
QPGPQPGPQPGPQPGPQSWMEEVIKLCGRELVRAQIAICGMSTWSGG
GSGGSGGGQLYSALANKCCHVGCTKRSLARFC.

Here, the RLN analog of SEQ ID NO:31 is generated essentially as described for Example 1 except that a cDNA sequence encoding SEQ ID NO:31 is used in the expression plasmid.

Example 9: Recombinant Expression of RLN Analog 9

Example 9 is a RLN analog having an amino acid sequence of:

(SEQ ID NO: 32)
SWMEEVIKLCGRELVRAQIAICGMSTWSGGGSGGSGGGQLYSALANK
CCHVGCTKRSLARFCGGGGQGGGGQGGGGQGGGGQGGGGQEVQLLES
GGGLVQPGGSLRLSCAASGRYIDETAVAWFRQAPGKGREFVAGIGGG

-continued

VDITYYADSVKGRFTISRDNSKNTLYLQMNSLRPEDTAVYYCAARPG

RPLITSKVADLYPYWGQGTLVTVSSPP.

Here, the RLN analog of SEQ ID NO:32 is generated essentially as described for Example 1 except that a cDNA sequence encoding SEQ ID NO:32 is used in the expression plasmid.

Example 10: Recombinant Expression of RLN Analog 10

Example 10 is a RLN analog having an amino acid sequence of:

(SEQ ID NO: 33)
SWMEEVIKLCGRELVRAQIAICGMSTWSGGGSGGSGGGQLYSALANK

CCHVGCTKRSLARFCPGPQPGPQPGPQPGPQPGPQPGPQPGPQPGPQ

EVQLLESGGGLVQPGGSLRLSCAASGRYIDETAVAWFRQAPGKGREF

VAGIGGGVDITYYADSVKGRFTISRDNSKNTLYLQMNSLRPEDTAVY

YCAARPGRPLITSKVADLYPYWGQGTLVTVSSPP.

Here, the RLN analog of SEQ ID NO:33 is generated essentially as described for Example 1 except that a cDNA sequence encoding SEQ ID NO:33 is used in the expression plasmid.

Example 11: Recombinant Expression of RLN Analog 11

Example 11 is a RLN analog having an amino acid sequence of:

(SEQ ID NO: 34)
EVQLLESGGGLVQPGGSLRLSCAASGRYIDETAVAWFRQAPGKEREF

VAGIGGGVDITYYADSVKGRFTISRDNSKNTLYLQMNSLRPEDTAVY

YCAARPGRPLITSKVADLYPYWGQGTLVTVSSGGGGQGGGGQGGGGQ

GGGGQGGGGQSWMEEVIKLCGRELVRAQIAICGMSTWSGGGSGGSGG

SGGGALANKCCHVGCTKRSLARFC.

Here, the RLN analog of SEQ ID NO:34 is generated essentially as described for Example 1 except that a cDNA sequence encoding SEQ ID NO:34 is used in the expression plasmid.

Example 12: Recombinant Expression of RLN Analog 12

Example 12 is a RLN analog having an amino acid sequence of:

(SEQ ID NO: 35)
EVQLLESGGGLVQPGGSLRLSCAASGRYIDETAVAWFRQAPGKGREF

VAGIGGGVDITYYADSVKGRFTISRDNSKNTLYLQMNSLRPEDTAVY

YCAARPGRPLITSKVADLYPYWGQGTLVTVSSGGGGQGGGGQGGGGQ

GGGGQGGGGQSWMEEVIKLCGRELVRAQIAICGMSTWSGGGSGGSGG

SGGGALANKCCHVGCTKRSLARFC.

Here, the RLN analog of SEQ ID NO:35 is generated essentially as described for Example 1 except that a cDNA sequence encoding SEQ ID NO:35 is used in the expression plasmid.

Example 13: Recombinant Expression of RLN Analog 13

Example 13 is a RLN analog having an amino acid sequence of:

(SEQ ID NO: 36)
EVQLLESGGGLVQPGGSLRLSCAASGRYIDETAVAWFRQAPGKGREF

VAGIGGGVDITYYADSVKGRFTISRDNSKNTLYLQMNSLRPEDTAVY

YCAARPGRPLITSKVADLYPYWGQGTLVTVSSGGGGQGGGGQGGGGQ

GGGGQGGGGQALANKCCHVGCTKRSLARFCGGGSGGSGGGSWMEEVI

KLCGRELVRAQIAICGMSTWS.

Here, the RLN analog of SEQ ID NO:36 is generated essentially as described for Example 1 except that a cDNA sequence encoding SEQ ID NO:36 is used in the expression plasmid.

Example 14: Recombinant Expression of RLN Analog 14

Example 14 is a RLN analog having an amino acid sequence of:

(SEQ ID NO: 37)
EVQLLESGGGLVQPGGSLRLSCAASGRYIDETAVAWFRQAPGKGREF

VAGIGGGVDITYYADSVKGRFTISRDNSKNTLYLQMNSLRPEDTAVY

YCAARPGRPLITSKVADLYPYWGQGTLVTVSSPGPQPGPQPGPQPGP

QPGPQPGPQPGPQPGPQALANKCCHVGCTKRSLARFCGGGSGGSGGG

SWMEEVIKLCGRELVRAQIAICGMSTWS.

Here, the RLN analog of SEQ ID NO:37 is generated essentially as described for Example 1 except that a cDNA sequence encoding SEQ ID NO:37 is used in the expression plasmid.

Example 15: Recombinant Expression of RLN Analog 15

Example 15 is a RLN analog having an amino sequence of:

(SEQ ID NO: 38)
EVQLLESGGGLVQPGGSLRLSCAASGRYIDETAVAWFRQAPGKEREF

VAGIGGGVDITYYADSVKGRFTISRDNSKNTLYLQMNSLRPEDTAVY

YCAARPGRPLITSKVADLYPYWGQGTLVTVSSGGGGQGGGGQGGGGQ

GGGGQGGGGQDSWMEEVIKLCGRELVRAQIAICGMSTWSSGGGGSGG

GGQLYSALANKCCHVGCTKRSLARFC.

Here, the RLN analog of SEQ ID NO:38 is generated essentially as described for Example 1 except that a cDNA sequence encoding SEQ ID NO:38 is used in the expression plasmid.

Example 16: Recombinant Expression of RLN Analog 16

Example 16 is a RLN analog having an amino sequence of:

(SEQ ID NO: 39)
EVQLLESGGGLVQPGGSLRLSCAASGRYIDETAVAWFRQAPGKEREF

VAGIGGGVDITYYADSVKGRFTISRDNSKNTLYLQMNSLRPEDTAVY

YCAARPGRPLITSKVADLYPYWGQGTLVTVSSPGPAPGPAPGPAPGP

APGPAPGPAPGPAPGPADSWMEEVIKLCGRELVRAQIAICGMSTWSS

GGGGSGGGGQLYSALANKCCHVGCTKRSLARFC.

Here, the RLN analog of SEQ ID NO:39 is generated essentially as described for Example 1 except that a cDNA sequence encoding SEQ ID NO:39 is used in the expression plasmid.

In Vitro Function

Example 17: RLN Analog Albumin-Binding Via SPR

In vitro binding of a RLN analog to human, cynomolgus monkey, mouse, rat, pig, dog, cow and rabbit serum albumin is determined by SPR. In particular, the affinity of the RLN analogs of Examples 1 to 14 to serum albumin of these species is summarized below in Tables 1 to 14.

Binding of the RLN analogs of Examples 1 to 14 to various serum albumins is carried out on Biacore 8K instrument. The immobilization of the serum albumin to a Series S Sensor Chip CM5 surface is performed according to the manufacturer's instructions (Amine Coupling Kit BR-1000-50). Briefly, carboxyl groups on the sensor chip surfaces (flow cell 1 and 2) are activated by injecting 70 μL of a mixture containing 75 mg/mL EDC and 11.5 mg/mL NHS at 10 μL/min. Human, cynomolgus monkey, mouse, rat, pig, dog, cow and rabbit serum albumin are diluted in 10 mM sodium acetate pH 4.0 (BR-1003-49) at 0.5, 0.5, 2.2, 0.6, 0.6, 0.8, 0.6 and 0.3 μg/mL and then injected over the activated chip surfaces (flow cell 2, channel 1 to 8) at 10 μL/min for 180 sec (human, mouse, rat, pig and cow serum albumin are obtained from Sigma Aldrich (St. Louis, Mo.); cynomolgus monkey serum albumin is obtained from Hölzel Diagnostika (Cologne, Germany); dog serum albumin is obtained from Molecular Innovations (Novi, Mich.); and rabbit serum albumin is obtained from Fitzgerald Industries Intl. (Acton, Mass.). The various serum albumins are covalently immobilized through free amines onto a carboxymethyl dextran-coated sensor chip CM5 targeting a surface density of about 100 (62-145) RU. Excess reactive groups on the surfaces (flow cell 1 and 2) are deactivated by injecting 70 μL of 1 M ETA HCl—NaOH pH 8.5.

The RLN analogs of Examples 1 to 14 are diluted in HBS-EP+ buffer (10 mM HEPES pH 7.6, 150 mM NaCl, 3 mM EDTA, 0.05% Polysorbate 20) at concentrations of 1000, 333.3, 111.1, 37.04, 12.35, 4.12, 1.37, 0.457, 0.152, 0.051 and 0.017 nM. 150 μl of sample is individually injecting sequentially across the immobilized serum albumins on the chip's surface and dissociating for 600 sec at 50 μL/min flow rate at 25° C. The surface is regenerated by injecting 10 mM glycine-HCl pH 1.5 (BR-1003-54) at 50 μL/min for 100 sec. The resulting sensorgrams are analyzed using Biacore 8K Insight Evaluation Software (version 2.0.15.12933) 1:1 binding kinetics model fitting to calculate the binding kinetic parameter association rate (ka), dissociation rate (kd), and equilibrium dissociation constant ($K_D$).

TABLE 1

Binding Kinetics of RLN Analog of Example 1 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 9.8E+05 | 1.1E−04 | 1.1E−10 |
| Cyno SA | 1.1E+06 | 5.3E−04 | 5.0E−10 |
| Mouse SA | 1.3E+06 | 4.2E−03 | 3.3E−09 |
| Rat SA | 1.2E+06 | 2.6E−03 | 2.1E−09 |
| Pig SA | 7.8E+05 | 5.5E−03 | 7.1E−09 |
| Dog SA | 1.3E+06 | 1.5E−03 | 1.2E−09 |
| Cow SA | 1.4E+06 | 5.0E−02 | 3.7E−08 |
| Rabbit SA | | No binding | |

$K_D$ is determined as 0.1, 0.5, 3.3, 2.1, 7.1, 1.2 and 37 nM for human, cynomolgus monkey, mouse, rat, pig, dog and cow serum albumin binding, respectively, with the RLN analog of Example 1.

TABLE 2

Binding Kinetics of RLN Analog of Example 2 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 9.2E+05 | 9.5E−05 | 1.0E−10 |
| Cyno SA | 1.2E+06 | 5.2E−04 | 4.5E−10 |
| Mouse SA | 1.1E+06 | 4.2E−03 | 3.8E−09 |
| Rat SA | 9.8E+05 | 2.9E−03 | 3.0E−09 |
| Pig SA | 6.9E+05 | 5.6E−03 | 8.0E−09 |
| Dog SA | 1.0E+06 | 1.5E−03 | 1.4E−09 |
| Cow SA | 9.8E+05 | 4.9E−02 | 5.0E−08 |
| Rabbit SA | | No binding | |

$K_D$ is determined as 0.1, 0.45, 3.8, 3.0, 8.0, 1.4 and 50 nM for human, cynomolgus monkey, mouse, rat, pig, dog and cow serum albumin binding, respectively, with the RLN analog of Example 2.

TABLE 3

Binding Kinetics of RLN Analog of Example 3 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.4E+06 | 1.1E−04 | 7.6E−11 |
| Cyno SA | 1.5E+06 | 5.4E−04 | 3.6E−10 |
| Mouse SA | 1.7E+06 | 4.0E−03 | 2.4E−09 |
| Rat SA | 1.7E+06 | 2.7E−03 | 1.6E−09 |
| Pig SA | 1.1E+06 | 5.3E−03 | 4.8E−09 |
| Dog SA | 2.0E+06 | 1.4E−03 | 7.0E−10 |
| Cow SA | n/a (steady state) | | 2.6E−08 |
| Rabbit SA | | No binding | |

$K_D$ is determined as 0.08, 0.36, 2.4, 1.6, 4.8, 0.7 and 26 nM for human, cynomolgus monkey, mouse, rat, pig, dog and cow serum albumin binding, respectively, with the RLN analog of Example 3.

TABLE 4

Binding Kinetics of RLN Analog of Example 4 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.2E+06 | 1.1E−04 | 8.9E−11 |
| Cyno SA | 1.3E+06 | 5.3E−04 | 4.2E−10 |
| Mouse SA | 1.3E+06 | 3.9E−03 | 3.0E−09 |
| Rat SA | 1.2E+06 | 2.6E−03 | 2.1E−09 |
| Pig SA | 8.6E+05 | 5.3E−03 | 6.2E−09 |
| Dog SA | 1.4E+06 | 1.4E−03 | 1.0E−09 |
| Cow SA | n/a (steady state) | | 3.7E−08 |
| Rabbit SA | No binding | | |

$K_D$ is determined as 0.09, 0.42, 3.0, 2.1, 6.2, 1.0 and 37 nM for human, cynomolgus monkey, mouse, rat, pig, dog and cow serum albumin binding, respectively, with the RLN analog of Example 4.

TABLE 5

Binding Kinetics of RLN Analog of Example 5 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 5.8E+05 | 2.6E−04 | 4.5E−10 |
| Cyno SA | 8.2E+05 | 1.5E−03 | 1.8E−09 |
| Mouse SA | 5.9E+05 | 8.3E−03 | 1.4E−08 |
| Rat SA | 7.0E+05 | 7.2E−03 | 1.0E−08 |
| Pig SA | 5.8E+05 | 1.3E−02 | 2.3E−08 |
| Dog SA | 7.1E+05 | 3.4E−03 | 4.7E−09 |
| Cow SA | n/a (steady state) | | 1.2E−07 |
| Rabbit SA | No binding | | |

$K_D$ is determined as 0.45, 1.8, 14, 10, 23, 4.7 and 120 nM for human, cynomolgus monkey, mouse, rat, pig, dog and cow serum albumin binding, respectively, with the RLN analog of Example 5.

TABLE 6

Binding Kinetics of RLN Analog of Example 6 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 4.7E+05 | 2.4E−04 | 5.1E−10 |
| Cyno SA | 4.3E+05 | 1.0E−03 | 2.3E−09 |
| Mouse SA | 6.3E+05 | 7.6E−03 | 1.2E−08 |
| Rat SA | 4.9E+05 | 4.8E−03 | 9.7E−09 |
| Pig SA | 4.1E+05 | 9.9E−03 | 2.4E−08 |
| Dog SA | 4.8E+05 | 2.0E−03 | 4.1E−09 |
| Cow SA | n/a (steady state) | | 1.3E−07 |
| Rabbit SA | No binding | | |

$K_D$ is determined as 0.51, 2.3, 12, 9.7, 24, 4.1 and 130 nM for human, cynomolgus monkey, mouse, rat, pig, dog and cow serum albumin binding, respectively, with the RLN analog of Example 6.

TABLE 7

Binding Kinetics of RLN Analog of Example 7 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.9E+06 | 1.2E−04 | 6.3E−11 |
| Cyno SA | 2.1E+06 | 5.9E−04 | 2.9E−10 |
| Mouse SA | 2.0E+06 | 4.1E−03 | 2.1E−09 |
| Rat SA | 2.0E+06 | 2.8E−03 | 1.4E−09 |
| Pig SA | 1.5E+06 | 5.4E−03 | 3.7E−09 |
| Dog SA | 2.2E+06 | 1.5E−03 | 6.9E−10 |
| Cow SA | n/a (steady state) | | 2.5E−08 |
| Rabbit SA | No binding | | |

$K_D$ is determined as 0.06, 0.29, 2.1, 1.4, 3.7, 0.69 and 25 nM for human, cynomolgus monkey, mouse, rat, pig, dog and cow serum albumin binding, respectively, with the RLN analog of Example 7.

TABLE 8

Binding Kinetics of RLN Analog of Example 8 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.5E+06 | 1.1E−04 | 7.8E−11 |
| Cyno SA | 1.9E+06 | 5.9E−04 | 3.2E−10 |
| Mouse SA | 2.2E+06 | 3.9E−03 | 1.8E−09 |
| Rat SA | 1.6E+06 | 2.8E−03 | 1.7E−09 |
| Pig SA | 1.3E+06 | 5.2E−03 | 4.1E−09 |
| Dog SA | 2.3E+06 | 1.5E−03 | 6.6E−10 |
| Cow SA | n/a (steady state) | | 2.1E−08 |
| Rabbit SA | No binding | | |

$K_D$ is determined as 0.08, 0.32, 1.8, 1.7, 4.1, 0.66 and 21 nM for human, cynomolgus monkey, mouse, rat, pig, dog and cow serum albumin binding, respectively, with the RLN analog of Example 8.

TABLE 9

Binding Kinetics of RLN Analog of Example 9 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 9.5E+05 | 1.8E−04 | 1.9E−10 |
| Cyno SA | 1.1E+06 | 9.4E−04 | 8.6E−10 |
| Mouse SA | 1.2E+06 | 1.1E−02 | 9.5E−09 |
| Rat SA | 9.1E+05 | 7.5E−03 | 8.2E−09 |
| Pig SA | 8.7E+05 | 1.2E−02 | 1.4E−08 |
| Dog SA | 9.5E+05 | 3.6E−03 | 3.8E−09 |
| Cow SA | n/a (steady state) | | 8.4E−08 |
| Rabbit SA | No binding | | |

$K_D$ is determined as 0.19, 0.86, 9.5, 8.2, 14, 3.8 and 84 nM for human, cynomolgus monkey, mouse, rat, pig, dog and cow serum albumin binding, respectively, with the RLN analog of Example 9.

TABLE 10

Binding Kinetics of RLN Analog of Example 10 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 5.5E+05 | 2.0E−04 | 3.7E−10 |
| Cyno SA | 5.1E+05 | 7.7E−04 | 1.5E−09 |

TABLE 10-continued

Binding Kinetics of RLN Analog of Example 10 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Mouse SA | 7.4E+05 | 7.2E−03 | 9.7E−09 |
| Rat SA | 6.3E+05 | 4.9E−03 | 7.8E−09 |
| Pig SA | 4.9E+05 | 9.6E−03 | 2.0E−08 |
| Dog SA | 6.3E+05 | 2.1E−03 | 3.4E−09 |
| Cow SA | n/a (steady state) | | 1.0E−07 |
| Rabbit SA | No binding | | |

$K_D$ is determined as 0.37, 1.5, 9.7, 7.8, 20, 3.4 and 100 nM for human, cynomolgus monkey, mouse, rat, pig, dog and cow serum albumin binding, respectively, with the RLN analog of Example 10.

TABLE 11

Binding Kinetics of RLN Analog of Example 11 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.2E+06 | 2.1E−04 | 1.7E−10 |
| Cyno SA | 1.3E+06 | 6.4E−04 | 4.8E−10 |
| Mouse SA | 1.4E+06 | 5.0E−03 | 3.6E−09 |
| Rat SA | 2.1E+06 | 2.8E−03 | 1.3E−09 |
| Pig SA | 8.5E+05 | 6.2E−03 | 7.3E−09 |
| Dog SA | 1.4E+06 | 1.7E−03 | 1.3E−09 |
| Cow SA | n/a (steady state) | | 2.7E−08 |
| Rabbit SA | No binding | | |

$K_D$ is determined as 0.17, 0.48, 3.6, 1.3, 7.3, 1.3 and 27 nM for human, cynomolgus monkey, mouse, rat, pig, dog and cow serum albumin binding, respectively, with the RLN analog of Example 11.

TABLE 12

Binding Kinetics of RLN Analog of Example 12 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.4E+06 | 1.9E−04 | 1.4E−10 |
| Cyno SA | 1.5E+06 | 7.0E−04 | 4.7E−10 |
| Mouse SA | 1.8E+06 | 4.9E−03 | 2.6E−09 |
| Rat SA | 2.0E+06 | 3.3E−03 | 1.7E−09 |
| Pig SA | 1.4E+06 | 5.8E−03 | 4.2E−09 |
| Dog SA | 2.1E+06 | 1.6E−03 | 7.7E−10 |
| Cow SA | n/a (steady state) | | 3.0E−08 |
| Rabbit SA | No binding | | |

$K_D$ is determined as 0.14, 0.47, 2.6, 1.7, 4.2, 0.77 and 30 nM for human, cynomolgus monkey, mouse, rat, pig, dog and cow serum albumin binding, respectively, with the RLN analog of Example 12.

TABLE 13

Binding Kinetics of RLN Analog of Example 13 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.4E+06 | 1.9E−04 | 1.4E−10 |
| Cyno SA | 1.4E+06 | 7.0E−04 | 4.9E−10 |
| Mouse SA | 1.8E+06 | 4.8E−03 | 2.6E−09 |
| Rat SA | 1.7E+06 | 3.3E−03 | 2.0E−09 |
| Pig SA | 1.2E+06 | 6.0E−03 | 5.0E−09 |
| Dog SA | 1.9E+06 | 1.7E−03 | 9.2E−10 |
| Cow SA | n/a (steady state) | | 2.9E−08 |
| Rabbit SA | No binding | | |

$K_D$ is determined as 0.14, 0.49, 2.6, 2.0, 5.0, 0.92 and 29 nM for human, cynomolgus monkey, mouse, rat, pig, dog and cow serum albumin binding, respectively, with the RLN analog of Example 13.

TABLE 14

Binding Kinetics of RLN Analog of Example 14 to Human, Cynomolgus Monkey, Mouse, Rat, Pig, Dog, Cow and Rabbit Serum Albumin at 25° C.

| Binding to Immobilized Serum Albumins (SA) | ka (1/Ms) | kd (1/s) | $K_D$ (M) |
|---|---|---|---|
| Human SA | 1.2E+06 | 1.9E−04 | 1.6E−10 |
| Cyno SA | 1.1E+06 | 6.8E−04 | 6.1E−10 |
| Mouse SA | 1.5E+06 | 4.6E−03 | 3.1E−09 |
| Rat SA | 1.4E+06 | 3.2E−03 | 2.2E−09 |
| Pig SA | 9.7E+05 | 5.8E−03 | 6.0E−09 |
| Dog SA | 1.5E+06 | 1.7E−03 | 1.1E−09 |
| Cow SA | n/a (steady state) | | 3.4E−08 |
| Rabbit SA | No binding | | |

$K_D$ is determined as 0.16, 0.61, 3.1, 2.2, 6.0, 1.1 and 34 nM for human, cynomolgus monkey, mouse, rat, pig, dog and cow serum albumin binding, respectively, with the RLN analog of Example 14.

Example 18: RLN Analog In Vitro Potency at RXFP1 and RXFP2 Receptors

Generating CHO-CRE-Luc cell line: CHO-K1 cells (ATCC) are cultured in DMEM-F12 3:1 with 5% FBS with 20 mM HEPES, 40 µg/mL L-proline, 1× antibiotics and split 1:5 every 2-3 days with TrypLE™ Express (Gibco). Cells are transfected with plasmid DNA of pGL4.29[luc2P/CRE/Hygro] (Promega) and Fugene HD (Promega) according to the manufacturer's instructions. Transfected cells are selected with hygromycin B at 1 mg/mL for 3-4 weeks. Clonal lines are obtained by limited dilution cloning into 96-well plates and are confirmed with a forskolin response by luciferase assay with Bright-Glo Reagent (Promega). Clones are expanded, harvested, resuspended in freezing media, aliquoted into cryovials, and kept in liquid nitrogen for long-term storage. The top responder is selected with the best forskolin response (signal to background ratio), clonal line #2B6, for subsequent transfection with human RXFP1 and RXFP2 receptors.

Generating CHO human RXFP1- and human RXFP2-expressing cell lines: CHO-CRE-Luc line #2B6 cells are cultured in DMEM-F12 3:1 with 5% FBS with 20 mM HEPES, 40 µg/mL L-proline, 1× antibiotics, 1 mg/mL hygromycin B and split 1:5 every 2-3 days with TrypLE Express (Gibco). Cells are transfected with plasmid DNA of human RXFP1 receptor or human RXFP2 receptor and Fugene HD (Promega) according to the manufacturer's instructions. Transfected cells are selected with hygromycin B (1 mg/mL) and puromycin (6 µg/mL) for 3-4 weeks.

Clonal lines are obtained by limited dilution cloning into 96-well plates. Clonal lines are confirmed by a human RLN2 response. Clones are expanded, harvested, resuspended in freezing media, aliquoted into cryovials, and kept frozen under liquid nitrogen for long-term storage. Clonal lines are selected with the best response to human RLN2 (signal to background ratio) for assay validation.

Human RXFP1 and RXFP2 receptor luciferase assay: CHO cell lines expressing the human RXFP1 or the human RXFP2 are cultured with selection medium (DMEM-F12 3:1 with 5% FBS with 20 mM HEPES, 40 μg/mL L-proline, 1× antibiotics, 6 μg/mL puromycin, 1 mg/mL hygromycin B). On Day −1 (the day before cAMP CRE luciferase reporter assay), cells are washed once with PBS, lifted from flasks with cell dissociation solution (enzyme free cell dissociation solution, GIBCO cat #13151-014:TrypLE™ Express=30:1), and resuspended in plating medium (DMEM-F12 3:1 with 20 mM HEPES, 1× antibiotics, 0.5% FBS). Cells are plated in a 96-well plate (Falcon Cat #353219) at 20,000 cells/0.1 mL/well. Cells are cultured at 37° C. 5% $CO_2$ overnight. On Day 1 (the day of cAMP CRE luciferase reporter assay), medium is removed and replaced with 90 serum-free medium (DMEM-F12 3:1 with 20 mM HEPES, 1× antibiotics). Plates are incubated at 37° C. for 2 hr, then 10 μL of 10× ligand is added (RLN2, final 1×). Plates are incubated for an additional 4 hr at 37° C. After the incubation period is complete, plates are brought to room temperature for 15 min. Then, 50 μL of Bright-Glo™ is added to each well, and plates are read on a Biotek Neo2 reader with Gen5 software.

Statistical analysis of data: Data is imported from the Biotek Neo2 reader into GraphPad Prism® software (GraphPad Software, LLC; La Jolla, Calif.; version 7). $EC_{50}$ values are generated by a variable slope-four parameter dose response curve analysis.

TABLE 15

In Vitro Potency of RLN Analogs to RXPF1 and RXPF2 Receptors.

| Compound | SEQ ID NO: | hRXFP1 $EC_{50}$ nM GeoMean | SEM | N | hRXFP2 $EC_{50}$ nM GeoMean | SEM | N | R2/R1 ratio |
|---|---|---|---|---|---|---|---|---|
| hRLN2 | 5 & 6 | 0.15 | 0.012 | 4 | 1.7 | 0.45 | 8 | 11 |
| Example 1 | 24 | 3.0 | 2.8 | 6 | 65 | 17 | 2 | 22 |
| Example 2 | 25 | 1.1 | 0.64 | 6 | 79 | 6.2 | 2 | 74 |
| Example 3 | 26 | 4.0 | 1.0 | 2 | 19 | 2.4 | 4 | 5 |
| Example 4 | 27 | 2.9 | 0.2 | 2 | 24 | 6.0 | 4 | 8 |
| Example 5 | 28 | 8.1 | 2.9 | 2 | 98 | 16 | 4 | 12 |
| Example 6 | 29 | 15 | 3.0 | 2 | 39 | 4.9 | 4 | 3 |
| Example 7 | 30 | 0.91 | 0.04 | 2 | 26 | 2.5 | 4 | 28 |
| Example 8 | 31 | 2.0 | 1.2 | 2 | 32 | 14 | 4 | 16 |
| Example 9 | 32 | 5.2 | 0.01 | 2 | 97 | 14 | 4 | 19 |
| Example 10 | 33 | 14 | 0.33 | 2 | 32 | 3.9 | 4 | 2 |
| Example 11 | 34 | 3.2 | 0.69 | 2 | 207 | 31 | 4 | 65 |
| Example 12 | 35 | 2.9 | 0.51 | 2 | 193 | 29 | 4 | 66 |
| Example 13 | 36 | 10 | 0.8 | 2 | 407 | 17 | 3 | 42 |
| Example 14 | 37 | 17 | 2.3 | 2 | 628 | 51 | 3 | 37 |
| Example 15 | 38 | 1.7 | 0.13 | 5 | 23 | 3.6 | 4 | 14 |
| Example 16 | 39 | 2.0 | 0.22 | 4 | 70 | 23 | 2 | 35 |

In Vivo Function

Example 19: Pharmacokinetics of RLN Analogs in Male Sprague Dawley Rats

Male Sprague Dawley rats are administered a single SQ dose of 200 nmol/kg of a RLN analog in His-NaCl buffer (pH 6.0) at a volume of 1.0 mL/kg. Blood is collected 3, 6, 12, 24, 48, 72, 96, 120, 144, 168 and 240 hr post-dose for pharmacokinetic characterization.

Plasma concentrations of the RLN analogs are determined by a qualified LC/MS method at Eli Lilly and Company. The Example compounds and an analog internal standard are extracted from 100% rat plasma using a human RLN antibody followed by detecting an N-terminal tryptic peptide using a Q-Exactive™ Orbitrap® mass spectrometer.

Data for the RLN analogs of Examples 4 and 7 are provided below in Table 16.

TABLE 16

Mean Plasma Pharmacokinetic Parameters for RLN Analogs Following a Single 200 nmol/kg SQ Dose to Male Sprague Dawley Rats.

| Compound | Animal ID | $t^{1/2}$ (hr) | $T_{max}$ (hr) | $C_{max}$ (nmol/L) | $AUC_{0-inf}$ (hr*nmol/L) | CL/F (mL/hr/kg) |
|---|---|---|---|---|---|---|
| Example 4 | 1 | 28.0 | 72 | 297 | 35510 | 5.63 |
|  | 2 | 28.8 | 48 | 368 | 37529 | 5.33 |
|  | 3 | 32.8 | 48 | 356 | 39220 | 5.10 |
|  | Mean | 29.9 | 56 | 340 | 37419 | 5.35 |
|  | SD | 2.6 | 14 | 38 | 1857 | 0.27 |
| Example 7 | 1 | 40.1 | 48 | 387 | 51939 | 3.85 |
|  | 2 | 37.9 | 72 | 487 | 57843 | 3.46 |
|  | 3 | 31.3 | 48 | 344 | 44409 | 4.50 |
|  | Mean | 36.4 | 56 | 406 | 51397 | 3.94 |
|  | SD | 4.6 | 14 | 74 | 6734 | 0.53 |

NOTE:
Abbreviations: $t^{1/2}$ = half-life, $T_{max}$ = time to maximum concentration, $C_{max}$ = maximum observed plasma concentration, $AUC_{0-inf}$ = area under the curve from time 0 hours to infinity, CL/F = clearance/bioavailability, N = 3 animals/group/time point.
As shown in Table 16, the RLN analogs of Examples 4 and 7 demonstrate an extended pharmacokinetic profile in Sprague Dawley rats.

Example 20: In Vivo Effect of RLN Analogs on Renal Blood Flow Following IV Administration in Male Sprague Dawley Rats Male, five-week old Sprague Dawley rats (Charles River Laboratories, Inc.) are housed in a vivarium on a normal light/dark cycle for one week prior to start of the experiment. The rats then are randomized into the following treatment groups: vehicle (20 mM His/20 mM NaCl, pH 6.0 buffer) and the RLN analog of Example 7 based on body weight. The RLN analog is dosed at 2.44 µg/kg IV bolus followed by 0.36 µg/kg/hr IV infusion, 8.13 µg/kg IV bolus followed by 1.2 µg/kg/hr IV infusion, 24.4 µg/kg IV bolus followed by 3.6 µg/kg/hr IV infusion, and 81.3 µg/kg IV bolus followed by 11.9 µg/kg/hr IV infusion.

To measure the effect of the RLN analog on renal blood flow, rats are anesthetized with urethane (1.2 g/kg, IP) and are prepared for abdominal/renal ultrasound imaging and renal artery pulsed-wave Doppler blood flow measurements (VisualSonics, Model Vevo 3100 ultrasound system; Fujifilm). A chronic tail vein catheter is placed for the IV bolus and infusion administration. After a 30-min acclimation period, a baseline and 3-hr post-start of dose renal blood flow measurements are acquired.

TABLE 17

Effect of IV Administered RLN Analog on Renal Blood Flow in Healthy Rats.

| Compound and Dose | Time | Renal Blood Flow (mL/min) | Percent Change from Vehicle (%) |
|---|---|---|---|
| Vehicle at 1.6 mL/kg IV bolus then 0.475 mL/kg/hr IV infusion | baseline 3-hr | 8.58 ± 0.16 8.56 ± 0.18 | — |
| Example 7 at 2.44 µg/kg IV bolus then 0.36 µg/kg/hr IV infusion | baseline 3-hr | 8.49 ± 0.31 8.59 ± 0.33 | 0.4 |
| Example 7 at 8.13 µg/kg IV bolus then 1.2 µg/kg/hr IV infusion | baseline 3-hr | 8.63 ± 0.44 10.84 ± 0.53†* | 26.3 |
| Example 7 at 24.4 µg/kg IV bolus then 3.6 µg/kg/hr IV infusion | baseline 3-hr | 8.54 ± 0.23 12.74 ± 0.37†* | 48.8 |
| Example 7 at 81.3 µg/kg IV bolus then 11.9 µg/kg/hr IV infusion | baseline 3-hr | 8.34 ± 0.15 13.73 ± 0.47†* | 60.4 |

NOTE:
results expressed as Mean ± SD, †significantly different from baseline p < 0.001 ANOVA, *significantly different from vehicle p < 0.001 ANOVA, N = 5 per treatment group.

As seen in Table 17, the RLN analog of Example 7 significantly increases renal blood flow in the 8.13 µg/kg IV bolus followed by 1.2 µg/kg/hr IV infusion, 24.4 µg/kg IV bolus followed by 3.6 µg/kg/hr IV infusion, and 81.3 µg/kg IV bolus followed by 11.9 µg/kg/hr IV infusion treated groups by 26.6, 48.8 and 60.4% after 3 hr of exposure.

Example 21: In Vivo Effect of RLN Analogs on Renal Blood Flow Following SQ Administration in Male Sprague Dawley Rats Male, five-week old Sprague Dawley rats (Charles River Laboratories, Inc.) are housed in a vivarium on a normal light/dark cycle for one week prior to start of the experiment. The rats then are randomized into the following treatment groups: vehicle (20 mM His/20 mM NaCl, pH 6.0 Buffer) and the RLN Analog of Example 7 based on body weight. The RLN analog is dosed SQ at 180 µg/kg.

To measure the effect of the RLN analog on renal blood flow, 48 hr after dosing the rats are anesthetized with urethane (1.2 g/kg, IP) and are prepared for abdominal/renal ultrasound imaging and renal artery pulsed-wave Doppler blood flow measurements (VisualSonics, Model Vevo 3100 ultrasound system; Fujifilm). After a 30-min acclimation period, the renal blood flow measurements are acquired.

TABLE 18

Effect of SQ Administered RLN Analog on Renal Blood Flow in Healthy Rats.

| Compound and Dose | Renal Blood Flow (mL/min) | Percent Change from Vehicle (%) |
|---|---|---|
| Vehicle at 5 mL/kg | 8.51 ± 0.33 | — |
| Example 7 at 180 µg/kg | 11.27 ± 0.81* | 32.4 |

NOTE:
results expressed as Mean ± SD, *significantly different from vehicle p < 0.001 ANOVA, N = 10 per treatment group.

As seen in Table 18, the RLN analog of Example 7 significantly increases renal blood flow after 48 hr of exposure to a SQ dose of 180 µg/kg.

SEQUENCES

The following nucleic and/or amino acid sequences are referred to in the disclosure and are provided below for reference.

human pro-RLN1
                                                        SEQ ID NO: 1
MPRLFLFHLLEFCLLLNQFSRAVAAKWKDDVIKLCGRELVRAQIAICGMSTWSKRSLSQE

DAPQTPRPVAEIVPSFINKDTETIIIMLEFIANLPPELKAALSERQPSLPELQQYVPALK

DSNLSFEEFKKLIRNRQSEAADSNPSELKYLGLDTHSQKKRRPYVALFEKCCLIGCTKRS

LAKYC human RLN1 A chain
                                                        SEQ ID NO: 2
PYVALFEKCCLIGCTKRSLAKYC human RLN1 B chain
                                                        SEQ ID NO: 3
VAAKWKDDVIKLCGRELVRAQIAICGMSTWS human pro-RLN2
                                                        SEQ ID NO: 4
MPRLFFFHLLGVCLLLNQFSRAVADSWMEEVIKLCGRELVRAQIAICGMSTWSK

RSLSQEDAPQTPRPVAEIVPSFINKDTETINMNISEFVANLPQELKLTLSEMQPALP

QLQQHVPVLKDSSLLFEEFKKLIRNRQSEAADSSPSELKYLGLDTHSRKKRQLYS

ALANKCCHVGCTKRSLARFC human RLN2 A chain
                                                        SEQ ID NO: 5
QLYSALANKCCHVGCTKRSLARFC human RLN2 B chain
                                                        SEQ ID NO: 6
DSWMEEVIKLCGRELVRAQIAICGMSTWS human pro-RLN3
                                                        SEQ ID NO: 7
MARYMLLLLLAVWVLTGELWPGAEARAAPYGVRLCGREFIRAVIFTCGGSRWR

RSDILAHEAMGDTFPDADADEDSLAGELDEAMGSSEWLALTKSPQAFYRGRPSW

QGTPGVLRGSRDVLAGLSSSCCKWGCSKSEISSLC human RLN3 A chain
                                                        SEQ ID NO: 8
DVLAGLSSSCCKWGCSKSEISSLC human RLN3 B chain
                                                        SEQ ID NO: 9
RAAPYGVRLCGREFIRAVIFTCGGSRW VHH moiety #1 (C22)
                                                        SEQ ID NO: 10
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSS

VHH moiety #2 (C22.43)
                                                        SEQ ID NO: 11
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSSPP

VHH moiety #3 (C80)
                                                        SEQ ID NO: 12
EVQLLESGGGLVQPGGSLRLSCAASGRYIDETAVAWFRQAPGKGREFVAGIGGG

VDITYYADSVKGRFTISRDNSKNTLYLQMNSLRPEDTAVYYCAARPGRPLITSKV

ADLYPYWGQGTLVTVSS

VHH moiety #4 (C80.43)
                                                        SEQ ID NO: 13
EVQLLESGGGLVQPGGSLRLSCAASGRYIDETAVAWFRQAPGKGREFVAGIGGG

```
VDITYYADSVKGRFTISRDNSKNTLYLQMNSLRPEDTAVYYCAARPGRPLITSKV

ADLYPYWGQGTLVTVSSPP

L₁ (basic sequence of (GGGGQ)ₙ)
                                                    SEQ ID NO: 14
GGGGQ L₁ (basic sequence of (GGGQ)ₙ)
                                                    SEQ ID NO: 15
GGGQ L₁ (basic sequence of (GGGGS)ₙ)
                                                    SEQ ID NO: 16
GGGGS L₁ (basic sequence of (PGPQ)ₙ)
                                                    SEQ ID NO: 17
PGPQ L₁ (basic sequence of (PGPA)ₙ)
                                                    SEQ ID NO: 18
PGPA L₁ #1 ((GGGGQ)₅)
                                                    SEQ ID NO: 19
GGGGQGGGGQGGGGQGGGGQGGGGQ L₁ #2 ((PGPQ)₈)
                                                    SEQ ID NO: 20
PGPQPGPQPGPQPGPQPGPQPGPQPGPQPGPQ L₁ #3 (PGPA)₈
                                                    SEQ ID NO: 21
PGPAPGPAPGPAPGPAPGPAPGPAPGPAPGPA L₂ #1
                                                    SEQ ID NO: 22
GGGSGGSGGG L₂ #2
                                                    SEQ ID NO: 23
GGGSGGSGGSGGG RLN2 Analog #1 (C22-(G4Q)₅-A10B(desB1)RLN)
                                                    SEQ ID NO: 24
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSSGGGGQGGGGQGGGGQGGGGQGGGGQQLYSALANK

CCHVGCTKRSLARFCGGGSGGSGGGSWMEEVIKLCGRELVRAQIAICGMSTWS

RLN2 Analog #2 (C22-(PGPA)₈-A10B(desB1)RLN)
                                                    SEQ ID NO: 25
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSSPGPAPGPAPGPAPGPAPGPAPGPAPGPAPGPAQLYSAL

ANKCCHVGCTKRSLARFCGGGSGGSGGGSWMEEVIKLCGRELVRAQIAICGMST

WS

RLN2 Analog #3 (C22-(G4Q)₅-B10A(desB1)RLN)
                                                    SEQ ID NO: 26
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSSGGGGQGGGGQGGGGQGGGGQGGGGQSWMEEVIKL

CGRELVRAQIAICGMSTWSGGGSGGSGGGQLYSALANKCCHVGCTKRSLARFC

RLN2 Analog #4 (C22-(PGPQ)₈-B10A(desB1)RLN)
                                                    SEQ ID NO: 27
EVQLLESGGGLVQPGGSLRLSCAASGRYIDETAVAWFRQAPGKEREFVAGIGGG
```

-continued

VDITYYADSVKGRFTISRDNSKNTLYLQMNSLRPEDTAVYYCAARPGRPLITSKV

ADLYPYWGQGTLVTVSSPGPQPGPQPGPQPGPQPGPQPGPQPGPQPGPQSWMEE

VIKLCGRELVRAQIAICGMSTWSGGGSGGSGGGQLYSALANKCCHVGCTKRSLA

RFC

RLN2 Analog #5 (B10A(desB1)RLN-$(G4Q)_5$-C22.43)

SEQ ID NO: 28
SWMEEVIKLCGRELVRAQIAICGMSTWSGGGSGGSGGGQLYSALANKCCHVGC

TKRSLARFCGGGGQGGGGQGGGGQGGGGQGGGGQEVQLLESGGGLVQPGGSL

RLSCAASGRYIDETAVAWFRQAPGKEREFVAGIGGGVDITYYADSVKGRFTISRD

NSKNTLYLQMNSLRPEDTAVYYCAARPGRPLITSKVADLYPYWGQGTLVTVSSP

P

RLN2 Analog #6 (B10A(desB1)RLN-$(PGPQ)_8$-C22.43)

SEQ ID NO: 29

SWMEEVIKLCGRELVRAQIAICGMSTWSGGGSGGSGGGQLYSALANKCCHVGC

TKRSLARFCPGPQPGPQPGPQPGPQPGPQPGPQPGPQPGPQEVQLLESGGGLVQP

GGSLRLSCAASGRYIDETAVAWFRQAPGKEREFVAGIGGGVDITYYADSVKGRF

TISRDNSKNTLYLQMNSLRPEDTAVYYCAARPGRPLITSKVADLYPYWGQGTLV

TVSSPP

RLN2 Analog #7 (C80-$(G4Q)_5$-B10A(desB1)RLN)

SEQ ID NO: 30

EVQLLESGGGLVQPGGSLRLSCAASGRYIDETAVAWFRQAPGKGREFVAGIGGG

VDITYYADSVKGRFTISRDNSKNTLYLQMNSLRPEDTAVYYCAARPGRPLITSKV

ADLYPYWGQGTLVTVSSGGGGQGGGGQGGGGQGGGGQGGGGQSWMEEVIKL

CGRELVRAQIAICGMSTWSGGGSGGSGGGQLYSALANKCCHVGCTKRSLARFC

RLN2 Analog #8 (C80-$(PGPQ)_8$-B10A(desB1)RLN)

SEQ ID NO: 31

EVQLLESGGGLVQPGGSLRLSCAASGRYIDETAVAWFRQAPGKGREFVAGIGGG

VDITYYADSVKGRFTISRDNSKNTLYLQMNSLRPEDTAVYYCAARPGRPLITSKV

ADLYPYWGQGTLVTVSSPGPQPGPQPGPQPGPQPGPQPGPQPGPQPGPQSWMEE

VIKLCGRELVRAQIAICGMSTWSGGGSGGSGGGQLYSALANKCCHVGCTKRSLA

RFC

RLN2 Analog #9 (B10A(desB1)RLN-$(G4Q)_5$-C80.43)

SEQ ID NO: 32

SWMEEVIKLCGRELVRAQIAICGMSTWSGGGSGGSGGGQLYSALANKCCHVGC

TKRSLARFCGGGGQGGGGQGGGGQGGGGQGGGGQEVQLLESGGGLVQPGGSL

RLSCAASGRYIDETAVAWFRQAPGKGREFVAGIGGGVDITYYADSVKGRFTISRD

NSKNTLYLQMNSLRPEDTAVYYCAARPGRPLITSKVADLYPYWGQGTLVTVSSP

P

RLN2 Analog #10 (B10A(desB1)RLN-$(PGPQ)_8$-C80.43)

SEQ ID NO: 33

SWMEEVIKLCGRELVRAQIAICGMSTWSGGGSGGSGGGQLYSALANKCCHVGC

TKRSLARFCPGPQPGPQPGPQPGPQPGPQPGPQPGPQPGPQEVQLLESGGGLVQP

GGSLRLSCAASGRYIDETAVAWFRQAPGKGREFVAGIGGGVDITYYADSVKGRF

TISRDNSKNTLYLQMNSLRPEDTAVYYCAARPGRPLITSKVADLYPYWGQGTLV

TVSSPP

RLN2 Analog #11 (C22-$(G4Q)_5$-B13A(desB1, desA1-4)RLN)

SEQ ID NO: 34

EVQLLESGGGLVQPGGSLRLSCAASGRYIDETAVAWFRQAPGKEREFVAGIGGG

-continued

VDITYYADSVKGRFTISRDNSKNTLYLQMNSLRPEDTAVYYCAARPGRPLITSKV

ADLYPYWGQGTLVTVSSGGGGQGGGGQGGGGQGGGGQGGGGQSWMEEVIKL

CGRELVRAQIAICGMSTWSGGGSGGSGGSGGGALANKCCHVGCTKRSLARFC

RLN2 Analog #12 (C80-$(G4Q)_5$-B13A(desB1, desA1-4)RLN)

SEQ ID NO: 35

EVQLLESGGGLVQPGGSLRLSCAASGRYIDETAVAWFRQAPGKGREFVAGIGGG

VDITYYADSVKGRFTISRDNSKNTLYLQMNSLRPEDTAVYYCAARPGRPLITSKV

ADLYPYWGQGTLVTVSSGGGGQGGGGQGGGGQGGGGQGGGGQSWMEEVIKL

CGRELVRAQIAICGMSTWSGGGSGGSGGSGGGALANKCCHVGCTKRSLARFC

RLN2 Analog #13 (C80-$(G4Q)_5$-A10B(desB1, desA1-4)RLN)

SEQ ID NO: 36

EVQLLESGGGLVQPGGSLRLSCAASGRYIDETAVAWFRQAPGKGREFVAGIGGG

VDITYYADSVKGRFTISRDNSKNTLYLQMNSLRPEDTAVYYCAARPGRPLITSKV

ADLYPYWGQGTLVTVSSGGGGQGGGGQGGGGQGGGGQGGGGQALANKCCHV

GCTKRSLARFCGGGSGGSGGGSWMEEVIKLCGRELVRAQIAICGMSTWS

RLN2 Analog #14 (C80-$(PGPQ)_8$-A10B(desB1, desA1-4)RLN)

SEQ ID NO: 37

EVQLLESGGGLVQPGGSLRLSCAASGRYIDETAVAWFRQAPGKGREFVAGIGGG

VDITYYADSVKGRFTISRDNSKNTLYLQMNSLRPEDTAVYYCAARPGRPLITSKV

ADLYPYWGQGTLVTVSSPGPQPGPQPGPQPGPQPGPQPGPQPGPQPGPQALANK

CCHVGCTKRSLARFCGGGSGGSGGGSWMEEVIKLCGRELVRAQIAICGMSTWS

RLN2 Analog #15 (C22-$(G4Q)_5$-B10ARLN)

SEQ ID NO: 38

EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSSGGGGQGGGGQGGGGQGGGGQGGGGQDSWMEEVIK

LCGRELVRAQIAICGMSTWSSGGGGSGGGGQLYSALANKCCHVGCTKRSLARFC

RLN2 Analog #16 (C22-(PGPA)8-B10ARLN)

SEQ ID NO: 39

EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSSPGPAPGPAPGPAPGPAPGPAPGPAPGPAPGPADSWME

EVIKLCGRELVRAQIAICGMSTWSSGGGGSGGGGQLYSALANKCCHVGCTKRSL

ARFC human RXFP1 receptor

SEQ ID NO: 40

MTSGSVFFYILIFGKYFSHGGGQDVKCSLGYFPCGNITKCLPQLLHCNGVDDCGN

QADEDNCGDNNGWSLQFDKYFASYYKMTSQYPFEAETPECLVGSVPVQCLCQG

LELDCDETNLRAVPSVSSNVTAMSLQWNLIRKLPPDCFKNYHDLQKLYLQNNKI

TSISIYAFRGLNSLTKLYLSHNRITFLKPGVFEDLHRLEWLIIEDNHLSRISPPTFYG

LNSLILLVLMNNVLTRLPDKPLCQHMPRLHWLDLEGNHIHNLRNLTFISCSNLTV

LVMRKNKINHLNENTFAPLQKLDELDLGSNKIENLPPLIFKDLKELSQLNLSYNPI

QKIQANQFDYLVKLKSLSLEGIEISNIQQRMFRPLMNLSHIYFKKFQYCGYAPHVR

SCKPNTDGISSLENLLASIIQRVFVWVVSAVTCFGNIFVICMRPYIRSENKLYAMSII

SLCCADCLMGIYLFVIGGFDLKFRGEYNKHAQLWMESTHCQLVGSLAILSTEVSV

LLLTFLTLEKYICIVYPFRCVRPGKCRTITVLILIWITGFIVAFIPLSNKEFFKNYYGT

-continued

NGVCFPLHSEDTESIGAQIYSVAIFLGINLAAFIIIVFSYGSMFYSVHQSAITATEIRN

QVKKEMILAKRFFFIVFTDALCWIPIFVVKFLSLLQVEIPGTITSWVVIFILPINSALN

PILYTLTTRPFKEMIHRFWYNYRQRKSMDSKGQKTYAPSFIWVEMWPLQEMPPE

LMKPDLFTYPCEMSLISQSTRLNSYS human RXFP2 receptor
SEQ ID NO: 41
MIVFLVFKHLFSLRLITMFFLLHFIVLINVKDFALTQGSMITPSCQKGYFPCGNLTK

CLPRAFHCDGKDDCGNGADEENCGDTSGWATIFGTVHGNANSVALTQECFLKQ

YPQCCDCKETELECVNGDLKSVPMISNNVTLLSLKKNKIHSLPDKVFIKYTLKKI

FLQHNCIRHISRKAFFGLCNLQILYLNHNCITTLRPGIFKDLHQLTWLILDDNPITRI

SQRLFTGLNSLFFLSMVNNYLEALPKQMCAQMPQLNWVDLEGNRIKYLTNSTFL

SCDSLTVLFLPRNQIGFVPEKTFSSLKNLGELDLSSNTITELSPHLFKDLKLLQKLN

LSSNPLMYLHKNQFESLKQLQSLDLERIEIPNINTRMFQPMKNLSHIYFKNFRYCS

YAPHVRICMPLTDGISSFEDLLANNILRIFVWVIAFITCFGNLFVIGMRSFIKAENTT

HAMSIKILCCADCLMGVYLFFVGIFDIKYRGQYQKYALLWMESVQCRLMGFLA

MLSTEVSVLLLTYLTLEKFLVIVFPFSNIRPGKRQTSVILICIWMAGFLIAVIPFWNK

DYFGNFYGKNGVCFPLYYDQTEDIGSKGYSLGIFLGVNLLAFLIIVFSYITMFCSIQ

KTALQTTEVRNCFGREVAVANRFFFIVFSDAICWIPVFVVKILSLFRVEIPDTMTS

WIVIFFLPVNSALNPILYTLTTNFFKDKLKQLLHKHQRKSIFKIKKKSLSTSIVWIED

SSSLKLGVLNKITLGDSIMKPVS human RXFP3 receptor
SEQ ID NO: 42
MQMADAATIATMNKAAGGDKLAELFSLVPDLLEAANTSGNASLQLPDLWWEL

GLELPDGAPPGHPPGSGGAESADTEARVRILISVVYWVVCALGLAGNLLVLYLM

KSMQGWRKSSINLFVTNLALTDFQFVLTLPFWAVENALDFKWPFGKAMCKIVS

MVTSMNMYASVFFLTAMSVTRYHSVASALKSHRTRGHGRGDCCGRSLGDSCCF

SAKALCVWIWALAALASLPSAIFSTTVKVMGEELCLVRFPDKLLGRDRQFWLGL

YHSQKVLLGFVLPLGIIILCYLLLVRFIADRRAAGTKGGAAVAGGRPTGASARRLS

KVTKSVTIVVLSFFLCWLPNQALTTWSILIKFNAVPFSQEYFLCQVYAFPVSVCLA

HSNSCLNPVLYCLVRREFRKALKSLLWRIASPSITSMRPFTATTKPEHEDQGLQAP

APPHAAAEPDLLYYPPGVVVYSGGRYDLLPSSSAY human RXFP4 receptor
SEQ ID NO: 43
MPTLNTSASPPTFFWANASGGSVLSADDAPMPVKFLALRLMVALAYGLVGAIGL

LGNLAVLWVLSNCARRAPGPPSDTFVFNLALADLGLALTLPFWAAESALDFHWP

FGGALCKMVLTATVLNVYASIFLITALSVARYWVVAMAAGPGTHLSLFWARIAT

LAVWAAAALVTVPTAVFGVEGEVCGVRLCLLRFPSRYWLGAYQLQRVVLAFM

VPLGVITTSYLLLLAFLQRRQRRRQDSRVVARSVRILVASFFLCWFPNHVVTLWG

VLVKFDLVPWNSTFYTIQTYVFPVTTCLAHSNSCLNPVLYCLLRREPRQALAGTF

RDLRLRLWPQGGGWVQQVALKQVGRRWVASNPRESRPSTLLTNLDRGTPG signal peptide
SEQ ID NO: 44
METDTLLLWVLLLWVPGSTG VHH moiety #5 (MC6.1)
SEQ ID NO: 45
EVQLLESGGGLVQPGGSLRLSCAASGRTVSSTAVAWFRQAPGKEREFVAGIGGS

```
VDITYYADSVKGRFTISRDNSKNTLYLQMNSLRPEDTAVYYCAVRPGRPLITSRD

ANLYDYWGQGTLVTVSS

VHH moiety #6 (MC6.1C6)
                                                SEQ ID NO: 46
EVQLLESGGGLVQPGGSLRLSCAASGRYIDSTAVAWFRQAPGKEREFVAGIGGG

VDITYYADSVKGRFTISRDNSKNTLYLQMNSLRPEDTAVYYCAARPGRPLITSRV

ANLYPYWGQGTLVTVSS

VHH moiety #7 (C22-G26Y)
                                                SEQ ID NO: 47
EVQLLESGGGLVQPGGSLRLSCAASYRYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSS

VHH moiety #8 (C22-R27A)
                                                SEQ ID NO: 48
EVQLLESGGGLVQPGGSLRLSCAASGAYIDETAVAWFRQAPGKEREFVAGIGGG

VDITYYADSVKGRFTISRDNSKNTLYLQMNSLRPEDTAVYYCAARPGRPLITSKV

ADLYPYWGQGTLVTVSS

VHH moiety #9 (C22-I57E)
                                                SEQ ID NO: 49
EVQLLESGGGLVQPGGSLRLSCAASGRYIDETAVAWFRQAPGKEREFVAGIGGG

VDETYYADSVKGRFTISRDNSKNTLYLQMNSLRPEDTAVYYCAARPGRPLITSKV

ADLYPYWGQGTLVTVSS

VHH moiety #10 (C22-I57Q)
                                                SEQ ID NO: 50
EVQLLESGGGLVQPGGSLRLSCAASGRYIDETAVAWFRQAPGKEREFVAGIGGG

VDQTYYADSVKGRFTISRDNSKNTLYLQMNSLRPEDTAVYYCAARPGRPLITSK

VADLYPYWGQGTLVTVSS

VHH moiety #11 (C22-Y59A)
                                                SEQ ID NO: 51
EVQLLESGGGLVQPGGSLRLSCAASGRYIDETAVAWFRQAPGKEREFVAGIGGG

VDITAYADSVKGRFTISRDNSKNTLYLQMNSLRPEDTAVYYCAARPGRPLITSKV

ADLYPYWGQGTLVTVSS

VHH moiety #12 (C22-Y59E)
                                                SEQ ID NO: 52
EVQLLESGGGLVQPGGSLRLSCAASGRYIDETAVAWFRQAPGKEREFVAGIGGG

VDITEYADSVKGRFTISRDNSKNTLYLQMNSLRPEDTAVYYCAARPGRPLITSKV

ADLYPYWGQGTLVTVSS

VHH moiety #13 (C22-Y59Q)
                                                SEQ ID NO: 53
EVQLLESGGGLVQPGGSLRLSCAASGRYIDETAVAWFRQAPGKEREFVAGIGGG

VDITQYADSVKGRFTISRDNSKNTLYLQMNSLRPEDTAVYYCAARPGRPLITSKV

ADLYPYWGQGTLVTVSS

VHH moiety #14 (C22-Y59S)
                                                SEQ ID NO: 54
EVQLLESGGGLVQPGGSLRLSCAASGRYIDETAVAWFRQAPGKEREFVAGIGGG

VDITSYADSVKGRFTISRDNSKNTLYLQMNSLRPEDTAVYYCAARPGRPLITSKV

ADLYPYWGQGTLVTVSS

VHH moiety #15 (C22-Y59T)
                                                SEQ ID NO: 55
EVQLLESGGGLVQPGGSLRLSCAASGRYIDETAVAWFRQAPGKEREFVAGIGGG
```

-continued

VDITTYADSVKGRFTISRDNSKNTLYLQMNSLRPEDTAVYYCAARPGRPLITSKV

ADLYPYWGQGTLVTVSS

VHH moiety #16 (C22-R102K)
SEQ ID NO: 56
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGKPLITSKV

ADLYPYWGQGTLVTVSS

VHH moiety #17 (C22-R102Q)
SEQ ID NO: 57
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGQPLITSKV

ADLYPYWGQGTLVTVSS

VHH moiety #18 (C22-R102S)
SEQ ID NO: 58
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGSPLITSKV

ADLYPYWGQGTLVTVSS

VHH moiety #19 (C22-P103E)
SEQ ID NO: 59
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRELITSKV

ADLYPYWGQGTLVTVSS

VHH moiety #20 (C22-P103Q)
SEQ ID NO: 60
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRQLITSKV

ADLYPYWGQGTLVTVSS

VHH moiety #21 (C22-P103S)
SEQ ID NO: 61
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRSLITSKV

ADLYPYWGQGTLVTVSS

VHH moiety #22 (C22-L104E)
SEQ ID NO: 62
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPEITSKV

ADLYPYWGQGTLVTVSS

VHH moiety #23 (C22-L104G)
SEQ ID NO: 63
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPGITSKV

ADLYPYWGQGTLVTVSS

VHH moiety #24 (C22-L104Q)
SEQ ID NO: 64
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPQITSKV

ADLYPYWGQGTLVTVSS

VHH moiety #25 (C22-L104T)
SEQ ID NO: 65
EVQLLESGGGLVQPGGSLRLSCAASGRYIDETAVAWFRQAPGKEREFVAGIGGG -continued

```
VDITYYADSVKGRFTISRDNSKNTLYLQMNSLRPEDTAVYYCAARPGRPTITSKV

ADLYPYWGQGTLVTVSS

VHH moiety #26 (C22-S107E)                                    SEQ ID NO: 66
EVQLLESGGGLVQPGGSLRLSCAASGRYIDETAVAWFRQAPGKEREFVAGIGGG

VDITYYADSVKGRFTISRDNSKNTLYLQMNSLRPEDTAVYYCAARPGRPLITEKV

ADLYPYWGQGTLVTVSS

L₂ #3                                                         SEQ ID NO: 67
SGGGGSGGGG
```

---

The invention claimed is:

1. A compound comprising a structure of:

VHH-L$_1$-A-L$_2$-B,

VHH-L$_1$-B-L$_2$-A,

A-L$_2$-B-L$_1$-VHH, or

B-L$_2$-A-L$_1$-VHH, wherein VHH comprises an amino acid sequence selected from the group consisting of SEQ ID NOS:10, 11, 12 and 13, wherein A is a relaxin A chain comprising an amino acid sequence selected from the group consisting of SEQ ID NOS:2, 5 and 8 or a sequence having at least 90% sequence similarity thereto, wherein B is a relaxin B chain comprising an amino acid sequence selected from the group consisting of SEQ ID NOS:3, 6 and 9 or a sequence having at least 90% sequence similarity thereto, wherein L$_1$ is a first linker comprising an amino acid sequence selected from the group consisting of (GGGGQ)$_n$ (SEQ ID NO:14), (PGPQ)$_n$ (SEQ ID NO:17) and (PGPA)$_n$ (SEQ ID NO:18), and wherein n can be from 1 to 10, and wherein L₂ is a second linker comprising an amino acid sequence selected from the group consisting of SEQ ID NOS:22, 23 and 67; or a pharmaceutically acceptable salt thereof.

2. The compound of claim 1, wherein A is SEQ ID NO:2.

3. The compound of claim 1, wherein B is SEQ ID NO:3.

4. The compound of claim 1, wherein A is SEQ ID NO:5.

5. The compound of claim 1, wherein B is SEQ ID NO:6.

6. The compound of claim 1, wherein A is SEQ ID NO:5 and lacks the first four amino acids (desA1-4).

7. The compound of claim 1, wherein B is SEQ ID NO:6 and lacks the first amino acid (desB1).

8. The compound of claim 1, wherein A is SEQ ID NO:5 and lacks the first four amino acids (desA1-4), and wherein B is SEQ ID NO:6 and lacks the first amino acid (desB1).

9. The compound of claim 1, wherein A is SEQ ID NO:8.

10. The compound of claim 1, wherein B is SEQ ID NO:9.

11. The compound of claim 1, wherein L₁ is SEQ ID NO:19.

12. The compound of claim 1, wherein L₁ is SEQ ID NO:20.

13. The compound of claim 1, wherein L₁ is SEQ ID NO:21.

14. The compound of claim 1 comprising an amino acid sequence selected from the group consisting of SEQ ID NOS:24 to 39 or a sequence having at least 90% sequence similarity thereto or a pharmaceutically acceptable salt thereof.

15. The compound of claim 1 consisting essentially of an amino acid sequence selected from the group consisting of SEQ ID NOS:24 to 39 or a sequence having at least 90% sequence similarity thereto or a pharmaceutically acceptable salt thereof.

16. The compound of claim 1 consisting of an amino acid sequence selected from the group consisting of SEQ ID NOS:24 to 39 or a sequence having at least 90% sequence similarity thereto or a pharmaceutically acceptable salt thereof.

17. A pharmaceutical composition comprising:
a compound of claim 1 or a pharmaceutically acceptable salt thereof; and
a pharmaceutically acceptable buffer.

18. A method of treating acute or chronic heart failure in an individual, the method comprising the step of:
administering to the individual an effective amount of a compound of claim 1.

\* \* \* \* \*

SEQUENCE LISTING

```
<160> NUMBER OF SEQ ID NOS: 67

<210> SEQ ID NO 1
<211> LENGTH: 185
<212> TYPE: PRT
<213> ORGANISM: Homo sapiens

<400> SEQUENCE: 1

Met Pro Arg Leu Phe Leu Phe His Leu Leu Glu Phe Cys Leu Leu
1               5                   10                  15

Asn Gln Phe Ser Arg Ala Val Ala Ala Lys Trp Lys Asp Asp Val Ile
                20                  25                  30

Lys Leu Cys Gly Arg Glu Leu Val Arg Ala Gln Ile Ala Ile Cys Gly
                35                  40                  45

Met Ser Thr Trp Ser Lys Arg Ser Leu Ser Gln Glu Asp Ala Pro Gln
        50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
                100                 105                 110

Gln Gln Tyr Val Pro Ala Leu Lys Asp Ser Asn Leu Ser Phe Glu Glu
            115                 120                 125

Phe Lys Lys Leu Ile Arg Asn Arg Gln Ser Glu Ala Ala Asp Ser Asn
    130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185

<210> SEQ ID NO 2
<211> LENGTH: 23
<212> TYPE: PRT
<213> ORGANISM: Homo sapiens

<400> SEQUENCE: 2

Pro Tyr Val Ala Leu Phe Glu Lys Cys Cys Leu Ile Gly Cys Thr Lys
1               5                   10                  15

Arg Ser Leu Ala Lys Tyr Cys
            20
```

<210> SEQ ID NO 3
<211> LENGTH: 31
<212> TYPE: PRT
<213> ORGANISM: Homo sapiens

<400> SEQUENCE: 3

Val Ala Ala Lys Trp Lys Asp Asp Val Ile Lys Leu Cys Gly Arg Glu
1               5                   10                  15

Leu Val Arg Ala Gln Ile Ala Ile Cys Gly Met Ser Thr Trp Ser
            20                  25                  30

<210> SEQ ID NO 4
<211> LENGTH: 185
<212> TYPE: PRT
<213> ORGANISM: Homo sapiens

<400> SEQUENCE: 4

Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
    130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185

<210> SEQ ID NO 5
<211> LENGTH: 24
<212> TYPE: PRT
<213> ORGANISM: Homo sapiens

<400> SEQUENCE: 5

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 6
<211> LENGTH: 29
<212> TYPE: PRT
<213> ORGANISM: Homo sapiens

```
<400> SEQUENCE: 6

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 7
<211> LENGTH: 142
<212> TYPE: PRT
<213> ORGANISM: Homo sapiens

<400> SEQUENCE: 7

Met Ala Arg Tyr Met Leu Leu Leu Leu Ala Val Trp Val Leu Thr
1               5                   10                  15

Gly Glu Leu Trp Pro Gly Ala Glu Ala Arg Ala Ala Pro Tyr Gly Val
            20                  25                  30

Arg Leu Cys Gly Arg Glu Phe Ile Arg Ala Val Ile Phe Thr Cys Gly
        35                  40                  45

Gly Ser Arg Trp Arg Arg Ser Asp Ile Leu Ala His Glu Ala Met Gly
    50                  55                  60

Asp Thr Phe Pro Asp Ala Asp Ala Asp Glu Asp Ser Leu Ala Gly Glu
65                  70                  75                  80

Leu Asp Glu Ala Met Gly Ser Ser Glu Trp Leu Ala Leu Thr Lys Ser
                85                  90                  95

Pro Gln Ala Phe Tyr Arg Gly Arg Pro Ser Trp Gln Gly Thr Pro Gly
            100                 105                 110

Val Leu Arg Gly Ser Arg Asp Val Leu Ala Gly Leu Ser Ser Ser Cys
        115                 120                 125

Cys Lys Trp Gly Cys Ser Lys Ser Glu Ile Ser Ser Leu Cys
    130                 135                 140

<210> SEQ ID NO 8
<211> LENGTH: 24
<212> TYPE: PRT
<213> ORGANISM: Homo sapiens

<400> SEQUENCE: 8

Asp Val Leu Ala Gly Leu Ser Ser Ser Cys Cys Lys Trp Gly Cys Ser
1               5                   10                  15

Lys Ser Glu Ile Ser Ser Leu Cys
            20

<210> SEQ ID NO 9
<211> LENGTH: 27
<212> TYPE: PRT
<213> ORGANISM: Homo sapiens

<400> SEQUENCE: 9

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
            20                  25

<210> SEQ ID NO 10
<211> LENGTH: 126
<212> TYPE: PRT
<213> ORGANISM: Artificial Sequence
<220> FEATURE:
<223> OTHER INFORMATION: Synthetic Construct
```

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125

<210> SEQ ID NO 11
<211> LENGTH: 128
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Pro
        115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Gly Arg Glu Phe Val
        35                  40                  45

Ala Gly Ile Gly Gly Gly Val Asp Ile Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
            115                 120                 125

<210> SEQ ID NO 13
<211> LENGTH: 128
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Gly Arg Glu Phe Val
            35                  40                  45

Ala Gly Ile Gly Gly Gly Val Asp Ile Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Pro
            115                 120                 125

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Gly Gly Gly Gly Gln
 1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic Construct

<400> SEQUENCE: 15

Gly Gly Gly Gln
 1

<210> SEQ ID NO 16
<211> LENGTH: 5
<212> TYPE: PRT

<213> ORGANISM: Artificial Sequence
<220> FEATURE:
<223> OTHER INFORMATION: Synthetic Construct

<400> SEQUENCE: 16

Gly Gly Gly Gly Ser
1               5

<210> SEQ ID NO 17
<211> LENGTH: 4
<212> TYPE: PRT
<213> ORGANISM: Artificial Sequence
<220> FEATURE:
<223> OTHER INFORMATION: Synthetic Construct

<400> SEQUENCE: 17

Pro Gly Pro Gln
1

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

Pro Gly Pro Ala
1

<210> SEQ ID NO 19
<211> LENGTH: 25
<212> TYPE: PRT
<213> ORGANISM: Artificial Sequence
<220> FEATURE:
<223> OTHER INFORMATION: Synthetic Construct

<400> SEQUENCE: 19

Gly Gly Gly Gly Gln Gly Gly Gly Gly Gln Gly Gly Gly Gly Gln Gly
1               5                   10                  15

Gly Gly Gly Gln Gly Gly Gly Gly Gln
            20                  25

<210> SEQ ID NO 20
<211> LENGTH: 32
<212> TYPE: PRT
<213> ORGANISM: Artificial Sequence
<220> FEATURE:
<223> OTHER INFORMATION: Synthetic Construct

<400> SEQUENCE: 20

Pro Gly Pro Gln Pro Gly Pro Gln Pro Gly Pro Gln Pro Gly Pro Gln
1               5                   10                  15

Pro Gly Pro Gln Pro Gly Pro Gln Pro Gly Pro Gln Pro Gly Pro Gln
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Synthetic Construct

<400> SEQUENCE: 21

Pro Gly Pro Ala Pro Gly Pro Ala Pro Gly Pro Ala Pro Gly Pro Ala
1               5                   10                  15

```
Pro Gly Pro Ala Pro Gly Pro Ala Pro Gly Pro Ala
            20                  25                  30
```

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

```
Gly Gly Gly Ser Gly Gly Ser Gly Gly Gly
1               5                   10
```

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct

<400> SEQUENCE: 23

```
Gly Gly Gly Ser Gly Gly Ser Gly Gly Ser Gly Gly Gly
1               5                   10
```

<210> SEQ ID NO 24
<211> LENGTH: 213
<212> TYPE: PRT
<213> ORGANISM: Artificial Sequence
<220> FEATURE:
<223> OTHER INFORMATION: Synthetic Construct

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Gly Gly
        115                 120                 125

Gly Gly Gln Gly Gly Gly Gln Gly Gly Gly Gln Gly Gly Gly
    130                 135                 140

Gly Gln Gly Gly Gly Gln Gln Leu Tyr Ser Ala Leu Ala Asn Lys
145                 150                 155                 160

Cys Cys His Val Gly Cys Thr Lys Arg Ser Leu Ala Arg Phe Cys Gly
                165                 170                 175

Gly Gly Ser Gly Gly Ser Gly Gly Ser Trp Met Glu Glu Val Ile
            180                 185                 190

Lys Leu Cys Gly Arg Glu Leu Val Arg Ala Gln Ile Ala Ile Cys Gly
        195                 200                 205
```

Met Ser Thr Trp Ser
    210

<210> SEQ ID NO 25
<211> LENGTH: 220
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Gly
        115                 120                 125

Pro Ala Pro Gly Pro Ala Pro Gly Pro Ala Pro Gly Pro Ala Pro Gly
    130                 135                 140

Pro Ala Pro Gly Pro Ala Pro Gly Pro Ala Pro Gly Pro Ala Gln Leu
145                 150                 155                 160

Tyr Ser Ala Leu Ala Asn Lys Cys Cys His Val Gly Cys Thr Lys Arg
                165                 170                 175

Ser Leu Ala Arg Phe Cys Gly Gly Ser Gly Gly Ser Gly Gly
            180                 185                 190

Ser Trp Met Glu Val Ile Lys Leu Cys Gly Arg Glu Leu Val Arg
        195                 200                 205

Ala Gln Ile Ala Ile Cys Gly Met Ser Thr Trp Ser
    210                 215                 220

<210> SEQ ID NO 26
<211> LENGTH: 213
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Gly Gly
        115                 120                 125

Gly Gly Gln Gly Gly Gly Gln Gly Gly Gly Gln Gly Gly Gly
130                 135                 140

Gly Gln Gly Gly Gly Gln Ser Trp Met Glu Val Ile Lys Leu
145                 150             155                 160

Cys Gly Arg Glu Leu Val Arg Ala Gln Ile Ala Ile Cys Gly Met Ser
            165                 170                 175

Thr Trp Ser Gly Gly Gly Ser Gly Gly Ser Gly Gly Gly Gln Leu Tyr
            180                 185                 190

Ser Ala Leu Ala Asn Lys Cys Cys His Val Gly Cys Thr Lys Arg Ser
            195                 200                 205

Leu Ala Arg Phe Cys
    210

<210> SEQ ID NO 27
<211> LENGTH: 220
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Gly
        115                 120                 125

Pro Gln Pro Gly Pro Gln Pro Gly Pro Gln Pro Gly Pro Gln Pro Gly
130                 135                 140

Pro Gln Pro Gly Pro Gln Pro Gly Pro Gln Pro Gly Pro Gln Ser Trp
145                 150                 155                 160

Met Glu Glu Val Ile Lys Leu Cys Gly Arg Glu Leu Val Arg Ala Gln
                165                 170                 175

Ile Ala Ile Cys Gly Met Ser Thr Trp Ser Gly Gly Gly Ser Gly Gly
            180                 185                 190

Ser Gly Gly Gly Gln Leu Tyr Ser Ala Leu Ala Asn Lys Cys Cys His
            195                 200                 205

Val Gly Cys Thr Lys Arg Ser Leu Ala Arg Phe Cys
    210                 215                 220

<210> SEQ ID NO 28
<211> LENGTH: 215
<212> TYPE: PRT
<213> ORGANISM: Artificial Sequence
<220> FEATURE:
<223> OTHER INFORMATION: Synthetic Construct

<400> SEQUENCE: 28

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser Gly Gly Gly Ser
            20                  25                  30

Gly Gly Ser Gly Gly Gly Gln Leu Tyr Ser Ala Leu Ala Asn Lys Cys
        35                  40                  45

Cys His Val Gly Cys Thr Lys Arg Ser Leu Ala Arg Phe Cys Gly Gly
    50                  55                  60

Gly Gly Gln Gly Gly Gly Gln Gly Gly Gly Gln Gly Gly Gly
65                  70                  75                  80

Gly Gln Gly Gly Gly Gln Glu Val Gln Leu Leu Glu Ser Gly Gly
                85                  90                  95

Gly Leu Val Gln Pro Gly Gly Ser Leu Arg Leu Ser Cys Ala Ala Ser
                100                 105                 110

Gly Arg Tyr Ile Asp Glu Thr Ala Val Ala Trp Phe Arg Gln Ala Pro
            115                 120                 125

Gly Lys Glu Arg Glu Phe Val Ala Gly Ile Gly Gly Gly Val Asp Ile
        130                 135                 140

Thr Tyr Tyr Ala Asp Ser Val Lys Gly Arg Phe Thr Ile Ser Arg Asp
145                 150                 155                 160

Asn Ser Lys Asn Thr Leu Tyr Leu Gln Met Asn Ser Leu Arg Pro Glu
                165                 170                 175

Asp Thr Ala Val Tyr Tyr Cys Ala Ala Arg Pro Gly Arg Pro Leu Ile
            180                 185                 190

Thr Ser Lys Val Ala Asp Leu Tyr Pro Tyr Trp Gly Gln Gly Thr Leu
        195                 200                 205

Val Thr Val Ser Ser Pro Pro
    210                 215

<210> SEQ ID NO 29
<211> LENGTH: 222
<212> TYPE: PRT
<213> ORGANISM: Artificial Sequence
<220> FEATURE:
<223> OTHER INFORMATION: Synthetic Construct

<400> SEQUENCE: 29

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser Gly Gly Gly Ser
            20                  25                  30

Gly Gly Ser Gly Gly Gly Gln Leu Tyr Ser Ala Leu Ala Asn Lys Cys
        35                  40                  45

Cys His Val Gly Cys Thr Lys Arg Ser Leu Ala Arg Phe Cys Pro Gly
    50                  55                  60

Pro Gln Pro Gly Pro Gln Pro Gly Pro Gln Pro Gly Pro Gln Pro Gly
65                  70                  75                  80

Pro Gln Pro Gly Pro Gln Pro Gly Pro Gln Pro Gly Pro Gln Glu Val 85                  90                  95
Gln Leu Leu Glu Ser Gly Gly Gly Leu Val Gln Pro Gly Gly Ser Leu
            100                 105                 110

Arg Leu Ser Cys Ala Ala Ser Gly Arg Tyr Ile Asp Glu Thr Ala Val
            115                 120                 125

Ala Trp Phe Arg Gln Ala Pro Gly Lys Glu Arg Glu Phe Val Ala Gly
            130                 135                 140

Ile Gly Gly Val Asp Ile Thr Tyr Ala Asp Ser Val Lys Gly
145                 150                 155                 160

Arg Phe Thr Ile Ser Arg Asp Asn Ser Lys Asn Thr Leu Tyr Leu Gln
                165                 170                 175

Met Asn Ser Leu Arg Pro Glu Asp Thr Ala Val Tyr Tyr Cys Ala Ala
            180                 185                 190

Arg Pro Gly Arg Pro Leu Ile Thr Ser Lys Val Ala Asp Leu Tyr Pro
            195                 200                 205

Tyr Trp Gly Gln Gly Thr Leu Val Thr Val Ser Ser Pro Pro
            210                 215                 220

<210> SEQ ID NO 30
<211> LENGTH: 213
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Gly Arg Glu Phe Val
        35                  40                  45

Ala Gly Ile Gly Gly Val Asp Ile Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Gly Gly
            115                 120                 125

Gly Gly Gln Gly Gly Gly Gln Gly Gly Gly Gln Gly Gly
            130                 135                 140

Gly Gly Gly Gly Gln Ser Trp Met Glu Val Ile Lys Leu
145                 150                 155                 160

Cys Gly Arg Glu Leu Val Arg Ala Gln Ile Ala Ile Cys Gly Met Ser
                165                 170                 175

Thr Trp Ser Gly Gly Gly Ser Gly Gly Ser Gly Gly Gly Gln Leu Tyr
            180                 185                 190

Ser Ala Leu Ala Asn Lys Cys Cys His Val Gly Cys Thr Lys Arg Ser
            195                 200                 205

Leu Ala Arg Phe Cys
    210

```
<210> SEQ ID NO 31
<211> LENGTH: 220
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Gly Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Gly
        115                 120                 125

Pro Gln Pro Gly Pro Gln Pro Gly Pro Gln Pro Gly Pro Gln Pro Gly
    130                 135                 140

Pro Gln Pro Gly Pro Gln Pro Gly Pro Gln Pro Gly Pro Gln Ser Trp
145                 150                 155                 160

Met Glu Glu Val Ile Lys Leu Cys Gly Arg Glu Leu Val Arg Ala Gln
                165                 170                 175

Ile Ala Ile Cys Gly Met Ser Thr Trp Ser Gly Gly Ser Gly Gly
            180                 185                 190

Ser Gly Gly Gly Gln Leu Tyr Ser Ala Leu Ala Asn Lys Cys Cys His
        195                 200                 205

Val Gly Cys Thr Lys Arg Ser Leu Ala Arg Phe Cys
    210                 215                 220

<210> SEQ ID NO 32
<211> LENGTH: 215
<212> TYPE: PRT
<213> ORGANISM: Artificial Sequence
<220> FEATURE:
<223> OTHER INFORMATION: Synthetic Construct

<400> SEQUENCE: 32

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser Gly Gly Gly Ser
            20                  25                  30

Gly Gly Ser Gly Gly Gly Gln Leu Tyr Ser Ala Leu Ala Asn Lys Cys
        35                  40                  45

Cys His Val Gly Cys Thr Lys Arg Ser Leu Ala Arg Phe Cys Gly Gly
    50                  55                  60

Gly Gly Gln Gly Gly Gly Gly Gln Gly Gly Gly Gly Gln Gly Gly
65                  70                  75                  80

Gly Gln Gly Gly Gly Gly Gln Glu Val Gln Leu Leu Glu Ser Gly Gly
                85                  90                  95
```

```
Gly Leu Val Gln Pro Gly Gly Ser Leu Arg Leu Ser Cys Ala Ala Ser
            100                 105                 110

Gly Arg Tyr Ile Asp Glu Thr Ala Val Ala Trp Phe Arg Gln Ala Pro
        115                 120                 125

Gly Lys Gly Arg Glu Phe Val Ala Gly Ile Gly Gly Val Asp Ile
    130                 135                 140

Thr Tyr Tyr Ala Asp Ser Val Lys Gly Arg Phe Thr Ile Ser Arg Asp
145                 150                 155                 160

Asn Ser Lys Asn Thr Leu Tyr Leu Gln Met Asn Ser Leu Arg Pro Glu
                165                 170                 175

Asp Thr Ala Val Tyr Tyr Cys Ala Ala Arg Pro Gly Arg Pro Leu Ile
            180                 185                 190

Thr Ser Lys Val Ala Asp Leu Tyr Pro Tyr Trp Gly Gln Gly Thr Leu
        195                 200                 205

Val Thr Val Ser Ser Pro Pro
        210                 215

<210> SEQ ID NO 33
<211> LENGTH: 222
<212> TYPE: PRT
<213> ORGANISM: Artificial Sequence
<220> FEATURE:
<223> OTHER INFORMATION: Synthetic Construct

<400> SEQUENCE: 33

Ser Trp Met Glu Glu Val Ile Lys Leu Cys Gly Arg Glu Leu Val Arg
1               5                   10                  15

Ala Gln Ile Ala Ile Cys Gly Met Ser Thr Trp Ser Gly Gly Gly Ser
            20                  25                  30

Gly Gly Ser Gly Gly Gly Gln Leu Tyr Ser Ala Leu Ala Asn Lys Cys
        35                  40                  45

Cys His Val Gly Cys Thr Lys Arg Ser Leu Ala Arg Phe Cys Pro Gly
    50                  55                  60

Pro Gln Pro Gly Pro Gln Pro Gly Pro Gln Pro Gly Pro Gln Pro Gly
65                  70                  75                  80

Pro Gln Pro Gly Pro Gln Pro Gly Pro Gln Pro Gly Pro Gln Glu Val
                85                  90                  95

Gln Leu Leu Glu Ser Gly Gly Gly Leu Val Gln Pro Gly Gly Ser Leu
            100                 105                 110

Arg Leu Ser Cys Ala Ala Ser Gly Arg Tyr Ile Asp Glu Thr Ala Val
        115                 120                 125

Ala Trp Phe Arg Gln Ala Pro Gly Lys Gly Arg Glu Phe Val Ala Gly
    130                 135                 140

Ile Gly Gly Val Asp Ile Thr Tyr Tyr Ala Asp Ser Val Lys Gly
145                 150                 155                 160

Arg Phe Thr Ile Ser Arg Asp Asn Ser Lys Asn Thr Leu Tyr Leu Gln
                165                 170                 175

Met Asn Ser Leu Arg Pro Glu Asp Thr Ala Val Tyr Tyr Cys Ala Ala
            180                 185                 190

Arg Pro Gly Arg Pro Leu Ile Thr Ser Lys Val Ala Asp Leu Tyr Pro
        195                 200                 205

Tyr Trp Gly Gln Gly Thr Leu Val Thr Val Ser Ser Pro Pro
    210                 215                 220

<210> SEQ ID NO 34
<211> LENGTH: 212
```

```
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Gly Gly
        115                 120                 125

Gly Gly Gln Gly Gly Gly Gln Gly Gly Gly Gln Gly Gly
    130                 135                 140

Gly Gln Gly Gly Gly Gln Ser Trp Met Glu Val Ile Lys Leu
145                 150                 155                 160

Cys Gly Arg Glu Leu Val Arg Ala Gln Ile Ala Ile Cys Gly Met Ser
                165                 170                 175

Thr Trp Ser Gly Gly Gly Ser Gly Gly Ser Gly Gly Ser Gly Gly Gly
            180                 185                 190

Ala Leu Ala Asn Lys Cys Cys His Val Gly Cys Thr Lys Arg Ser Leu
            195                 200                 205

Ala Arg Phe Cys
    210

<210> SEQ ID NO 35
<211> LENGTH: 212
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Gly Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110
```

```
Tyr Pro Tyr Trp Gly Gln Gly Thr Leu Val Thr Val Ser Ser Gly Gly
            115                 120                 125

Gly Gly Gln Gly Gly Gly Gln Gly Gly Gly Gln Gly Gly Gly
        130                 135                 140

Gly Gln Gly Gly Gly Gln Ser Trp Met Glu Glu Val Ile Lys Leu
145                 150                 155                 160

Cys Gly Arg Glu Leu Val Arg Ala Gln Ile Ala Ile Cys Gly Met Ser
            165                 170                 175

Thr Trp Ser Gly Gly Ser Gly Gly Ser Gly Gly Ser Gly Gly
            180                 185                 190

Ala Leu Ala Asn Lys Cys Cys His Val Gly Cys Thr Lys Arg Ser Leu
            195                 200                 205

Ala Arg Phe Cys
        210

<210> SEQ ID NO 36
<211> LENGTH: 209
<212> TYPE: PRT
<213> ORGANISM: Artificial Sequence
<220> FEATURE:
<223> OTHER INFORMATION: Synthetic Construct

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Gly Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Gly Gly
        115                 120                 125

Gly Gly Gln Gly Gly Gly Gln Gly Gly Gly Gln Gly Gly Gly
        130                 135                 140

Gly Gln Gly Gly Gly Gln Ala Leu Ala Asn Lys Cys Cys His Val
145                 150                 155                 160

Gly Cys Thr Lys Arg Ser Leu Ala Arg Phe Cys Gly Gly Gly Ser Gly
            165                 170                 175

Gly Ser Gly Gly Gly Ser Trp Met Glu Glu Val Ile Lys Leu Cys Gly
            180                 185                 190

Arg Glu Leu Val Arg Ala Gln Ile Ala Ile Cys Gly Met Ser Thr Trp
        195                 200                 205

Ser

<210> SEQ ID NO 37
<211> LENGTH: 216
<212> TYPE: PRT
<213> ORGANISM: Artificial Sequence
<220> FEATURE:
```

<223> OTHER INFORMATION: Synthetic Construct

<400> SEQUENCE: 37

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Gly Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Gly
        115                 120                 125

Pro Gln Pro Gly Pro Gln Pro Gly Pro Gln Pro Gly Pro Gln Pro Gly
    130                 135                 140

Pro Gln Pro Gly Pro Gln Pro Gly Pro Gln Pro Gly Pro Gln Ala Leu
145                 150                 155                 160

Ala Asn Lys Cys Cys His Val Gly Cys Thr Lys Arg Ser Leu Ala Arg
                165                 170                 175

Phe Cys Gly Gly Gly Ser Gly Gly Ser Gly Gly Gly Ser Trp Met Glu
            180                 185                 190

Glu Val Ile Lys Leu Cys Gly Arg Glu Leu Val Arg Ala Gln Ile Ala
        195                 200                 205

Ile Cys Gly Met Ser Thr Trp Ser
    210                 215
```

<210> SEQ ID NO 38
<211> LENGTH: 214
<212> TYPE: PRT
<213> ORGANISM: Artificial Sequence
<220> FEATURE:
<223> OTHER INFORMATION: Synthetic Construct

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Gly Gly
        115                 120                 125
```

Gly Gly Gln Gly Gly Gly Gln Gly Gly Gly Gln Gly Gly Gly
        130                 135                 140

Gly Gln Gly Gly Gly Gln Asp Ser Trp Met Glu Val Ile Lys
145                 150                 155                 160

Leu Cys Gly Arg Glu Leu Val Arg Ala Gln Ile Ala Ile Cys Gly Met
                165                 170                 175

Ser Thr Trp Ser Ser Gly Gly Gly Ser Gly Gly Gly Gly Gln Leu
            180                 185                 190

Tyr Ser Ala Leu Ala Asn Lys Cys Cys His Val Gly Cys Thr Lys Arg
        195                 200                 205

Ser Leu Ala Arg Phe Cys
    210

<210> SEQ ID NO 39
<211> LENGTH: 221
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser Pro Gly
        115                 120                 125

Pro Ala Pro Gly Pro Ala Pro Gly Pro Ala Pro Gly Pro Ala Pro Gly
    130                 135                 140

Pro Ala Pro Gly Pro Ala Pro Gly Pro Ala Pro Gly Pro Ala Asp Ser
145                 150                 155                 160

Trp Met Glu Val Ile Lys Leu Cys Gly Arg Glu Leu Val Arg Ala
                165                 170                 175

Gln Ile Ala Ile Cys Gly Met Ser Thr Trp Ser Ser Gly Gly Gly
            180                 185                 190

Ser Gly Gly Gly Gly Gln Leu Tyr Ser Ala Leu Ala Asn Lys Cys Cys
        195                 200                 205

His Val Gly Cys Thr Lys Arg Ser Leu Ala Arg Phe Cys
    210                 215                 220

<210> SEQ ID NO 40
<211> LENGTH: 757
<212> TYPE: PRT
<213> ORGANISM: Homo sapiens

<400> SEQUENCE: 40

-continued

```
Met Thr Ser Gly Ser Val Phe Phe Tyr Ile Leu Ile Phe Gly Lys Tyr
1               5                   10                  15

Phe Ser His Gly Gly Gln Asp Val Lys Cys Ser Leu Gly Tyr Phe
            20                  25                  30

Pro Cys Gly Asn Ile Thr Lys Cys Leu Pro Gln Leu Leu His Cys Asn
        35                  40                  45

Gly Val Asp Asp Cys Gly Asn Gln Ala Asp Glu Asp Asn Cys Gly Asp
    50                  55                  60

Asn Asn Gly Trp Ser Leu Gln Phe Asp Lys Tyr Phe Ala Ser Tyr Tyr
65                  70                  75                  80

Lys Met Thr Ser Gln Tyr Pro Phe Glu Ala Glu Thr Pro Glu Cys Leu
                85                  90                  95

Val Gly Ser Val Pro Val Gln Cys Leu Cys Gln Gly Leu Glu Leu Asp
            100                 105                 110

Cys Asp Glu Thr Asn Leu Arg Ala Val Pro Ser Val Ser Ser Asn Val
        115                 120                 125

Thr Ala Met Ser Leu Gln Trp Asn Leu Ile Arg Lys Leu Pro Pro Asp
    130                 135                 140

Cys Phe Lys Asn Tyr His Asp Leu Gln Lys Leu Tyr Leu Gln Asn Asn
145                 150                 155                 160

Lys Ile Thr Ser Ile Ser Ile Tyr Ala Phe Arg Gly Leu Asn Ser Leu
                165                 170                 175

Thr Lys Leu Tyr Leu Ser His Asn Arg Ile Thr Phe Leu Lys Pro Gly
            180                 185                 190

Val Phe Glu Asp Leu His Arg Leu Glu Trp Leu Ile Ile Glu Asp Asn
        195                 200                 205

His Leu Ser Arg Ile Ser Pro Pro Thr Phe Tyr Gly Leu Asn Ser Leu
    210                 215                 220

Ile Leu Leu Val Leu Met Asn Asn Val Leu Thr Arg Leu Pro Asp Lys
225                 230                 235                 240

Pro Leu Cys Gln His Met Pro Arg Leu His Trp Leu Asp Leu Glu Gly
                245                 250                 255

Asn His Ile His Asn Leu Arg Asn Leu Thr Phe Ile Ser Cys Ser Asn
            260                 265                 270

Leu Thr Val Leu Val Met Arg Lys Asn Lys Ile Asn His Leu Asn Glu
        275                 280                 285

Asn Thr Phe Ala Pro Leu Gln Lys Leu Asp Glu Leu Asp Leu Gly Ser
    290                 295                 300

Asn Lys Ile Glu Asn Leu Pro Pro Leu Ile Phe Lys Asp Leu Lys Glu
305                 310                 315                 320

Leu Ser Gln Leu Asn Leu Ser Tyr Asn Pro Ile Gln Lys Ile Gln Ala
                325                 330                 335

Asn Gln Phe Asp Tyr Leu Val Lys Leu Lys Ser Leu Ser Leu Glu Gly
            340                 345                 350

Ile Glu Ile Ser Asn Ile Gln Gln Arg Met Phe Arg Pro Leu Met Asn
        355                 360                 365

Leu Ser His Ile Tyr Phe Lys Lys Phe Gln Tyr Cys Gly Tyr Ala Pro
    370                 375                 380

His Val Arg Ser Cys Lys Pro Asn Thr Asp Gly Ile Ser Ser Leu Glu
385                 390                 395                 400

Asn Leu Leu Ala Ser Ile Ile Gln Arg Val Phe Val Trp Val Val Ser
                405                 410                 415

Ala Val Thr Cys Phe Gly Asn Ile Phe Val Ile Cys Met Arg Pro Tyr
```

```
                420             425             430
Ile Arg Ser Glu Asn Lys Leu Tyr Ala Met Ser Ile Ile Ser Leu Cys
            435             440             445
Cys Ala Asp Cys Leu Met Gly Ile Tyr Leu Phe Val Ile Gly Gly Phe
450             455             460
Asp Leu Lys Phe Arg Gly Glu Tyr Asn Lys His Ala Gln Leu Trp Met
465             470             475             480
Glu Ser Thr His Cys Gln Leu Val Gly Ser Leu Ala Ile Leu Ser Thr
            485             490             495
Glu Val Ser Val Leu Leu Leu Thr Phe Leu Thr Leu Glu Lys Tyr Ile
            500             505             510
Cys Ile Val Tyr Pro Phe Arg Cys Val Arg Pro Gly Lys Cys Arg Thr
            515             520             525
Ile Thr Val Leu Ile Leu Ile Trp Ile Thr Gly Phe Ile Val Ala Phe
            530             535             540
Ile Pro Leu Ser Asn Lys Glu Phe Phe Lys Asn Tyr Tyr Gly Thr Asn
545             550             555             560
Gly Val Cys Phe Pro Leu His Ser Glu Asp Thr Glu Ser Ile Gly Ala
            565             570             575
Gln Ile Tyr Ser Val Ala Ile Phe Leu Gly Ile Asn Leu Ala Ala Phe
            580             585             590
Ile Ile Ile Val Phe Ser Tyr Gly Ser Met Phe Tyr Ser Val His Gln
            595             600             605
Ser Ala Ile Thr Ala Thr Glu Ile Arg Asn Gln Val Lys Lys Glu Met
            610             615             620
Ile Leu Ala Lys Arg Phe Phe Phe Ile Val Phe Thr Asp Ala Leu Cys
625             630             635             640
Trp Ile Pro Ile Phe Val Val Lys Phe Leu Ser Leu Leu Gln Val Glu
            645             650             655
Ile Pro Gly Thr Ile Thr Ser Trp Val Val Ile Phe Ile Leu Pro Ile
            660             665             670
Asn Ser Ala Leu Asn Pro Ile Leu Tyr Thr Leu Thr Thr Arg Pro Phe
            675             680             685
Lys Glu Met Ile His Arg Phe Trp Tyr Asn Tyr Arg Gln Arg Lys Ser
            690             695             700
Met Asp Ser Lys Gly Gln Lys Thr Tyr Ala Pro Ser Phe Ile Trp Val
705             710             715             720
Glu Met Trp Pro Leu Gln Glu Met Pro Pro Glu Leu Met Lys Pro Asp
            725             730             735
Leu Phe Thr Tyr Pro Cys Glu Met Ser Leu Ile Ser Gln Ser Thr Arg
            740             745             750
Leu Asn Ser Tyr Ser
            755

<210> SEQ ID NO 41
<211> LENGTH: 754
<212> TYPE: PRT
<213> ORGANISM: Homo sapiens

<400> SEQUENCE: 41

Met Ile Val Phe Leu Val Phe Lys His Leu Phe Ser Leu Arg Leu Ile
1               5                  10                  15
Thr Met Phe Phe Leu Leu His Pro Ile Val Leu Ile Asn Val Lys Asp
            20                  25                  30
```

```
Phe Ala Leu Thr Gln Gly Ser Met Ile Thr Pro Ser Cys Gln Lys Gly
             35                  40                  45

Tyr Phe Pro Cys Gly Asn Leu Thr Lys Cys Leu Pro Arg Ala Phe His
 50                  55                  60

Cys Asp Gly Lys Asp Asp Cys Gly Asn Gly Ala Asp Glu Glu Asn Cys
 65                  70                  75                  80

Gly Asp Thr Ser Gly Trp Ala Thr Ile Phe Gly Thr Val His Gly Asn
                 85                  90                  95

Ala Asn Ser Val Ala Leu Thr Gln Glu Cys Phe Leu Lys Gln Tyr Pro
                100                 105                 110

Gln Cys Cys Asp Cys Lys Glu Thr Glu Leu Glu Cys Val Asn Gly Asp
            115                 120                 125

Leu Lys Ser Val Pro Met Ile Ser Asn Asn Val Thr Leu Leu Ser Leu
        130                 135                 140

Lys Lys Asn Lys Ile His Ser Leu Pro Asp Lys Val Phe Ile Lys Tyr
145                 150                 155                 160

Thr Lys Leu Lys Lys Ile Phe Leu Gln His Asn Cys Ile Arg His Ile
                165                 170                 175

Ser Arg Lys Ala Phe Phe Gly Leu Cys Asn Leu Gln Ile Leu Tyr Leu
            180                 185                 190

Asn His Asn Cys Ile Thr Thr Leu Arg Pro Gly Ile Phe Lys Asp Leu
        195                 200                 205

His Gln Leu Thr Trp Leu Ile Leu Asp Asp Asn Pro Ile Thr Arg Ile
    210                 215                 220

Ser Gln Arg Leu Phe Thr Gly Leu Asn Ser Leu Phe Phe Leu Ser Met
225                 230                 235                 240

Val Asn Asn Tyr Leu Glu Ala Leu Pro Lys Gln Met Cys Ala Gln Met
                245                 250                 255

Pro Gln Leu Asn Trp Val Asp Leu Glu Gly Asn Arg Ile Lys Tyr Leu
            260                 265                 270

Thr Asn Ser Thr Phe Leu Ser Cys Asp Ser Leu Thr Val Leu Phe Leu
        275                 280                 285

Pro Arg Asn Gln Ile Gly Phe Val Pro Glu Lys Thr Phe Ser Ser Leu
    290                 295                 300

Lys Asn Leu Gly Glu Leu Asp Leu Ser Ser Asn Thr Ile Thr Glu Leu
305                 310                 315                 320

Ser Pro His Leu Phe Lys Asp Leu Lys Leu Leu Gln Lys Leu Asn Leu
                325                 330                 335

Ser Ser Asn Pro Leu Met Tyr Leu His Lys Asn Gln Phe Glu Ser Leu
            340                 345                 350

Lys Gln Leu Gln Ser Leu Asp Leu Glu Arg Ile Glu Ile Pro Asn Ile
        355                 360                 365

Asn Thr Arg Met Phe Gln Pro Met Lys Asn Leu Ser His Ile Tyr Phe
    370                 375                 380

Lys Asn Phe Arg Tyr Cys Ser Tyr Ala Pro His Val Arg Ile Cys Met
385                 390                 395                 400

Pro Leu Thr Asp Gly Ile Ser Ser Phe Glu Asp Leu Leu Ala Asn Asn
                405                 410                 415

Ile Leu Arg Ile Phe Val Trp Val Ile Ala Phe Ile Thr Cys Phe Gly
            420                 425                 430

Asn Leu Phe Val Ile Gly Met Arg Ser Phe Ile Lys Ala Glu Asn Thr
        435                 440                 445

Thr His Ala Met Ser Ile Lys Ile Leu Cys Cys Ala Asp Cys Leu Met
```

```
            450                 455                 460
Gly Val Tyr Leu Phe Phe Val Gly Ile Phe Asp Ile Lys Tyr Arg Gly
465                 470                 475                 480

Gln Tyr Gln Lys Tyr Ala Leu Leu Trp Met Glu Ser Val Gln Cys Arg
                485                 490                 495

Leu Met Gly Phe Leu Ala Met Leu Ser Thr Glu Val Ser Val Leu Leu
            500                 505                 510

Leu Thr Tyr Leu Thr Leu Glu Lys Phe Leu Val Ile Val Phe Pro Phe
        515                 520                 525

Ser Asn Ile Arg Pro Gly Lys Arg Gln Thr Ser Val Ile Leu Ile Cys
    530                 535                 540

Ile Trp Met Ala Gly Phe Leu Ile Ala Val Ile Pro Phe Trp Asn Lys
545                 550                 555                 560

Asp Tyr Phe Gly Asn Phe Tyr Gly Lys Asn Gly Val Cys Phe Pro Leu
                565                 570                 575

Tyr Tyr Asp Gln Thr Glu Asp Ile Gly Ser Lys Gly Tyr Ser Leu Gly
            580                 585                 590

Ile Phe Leu Gly Val Asn Leu Leu Ala Phe Leu Ile Ile Val Phe Ser
        595                 600                 605

Tyr Ile Thr Met Phe Cys Ser Ile Gln Lys Thr Ala Leu Gln Thr Thr
    610                 615                 620

Glu Val Arg Asn Cys Phe Gly Arg Glu Val Ala Val Ala Asn Arg Phe
625                 630                 635                 640

Phe Phe Ile Val Phe Ser Asp Ala Ile Cys Trp Ile Pro Val Phe Val
                645                 650                 655

Val Lys Ile Leu Ser Leu Phe Arg Val Glu Ile Pro Asp Thr Met Thr
            660                 665                 670

Ser Trp Ile Val Ile Phe Leu Pro Val Asn Ser Ala Leu Asn Pro
        675                 680                 685

Ile Leu Tyr Thr Leu Thr Thr Asn Phe Phe Lys Asp Lys Leu Lys Gln
    690                 695                 700

Leu Leu His Lys His Gln Arg Lys Ser Ile Phe Lys Ile Lys Lys Lys
705                 710                 715                 720

Ser Leu Ser Thr Ser Ile Val Trp Ile Glu Asp Ser Ser Leu Lys
                725                 730                 735

Leu Gly Val Leu Asn Lys Ile Thr Leu Gly Asp Ser Ile Met Lys Pro
            740                 745                 750

Val Ser

<210> SEQ ID NO 42
<211> LENGTH: 469
<212> TYPE: PRT
<213> ORGANISM: Homo sapiens

<400> SEQUENCE: 42

Met Gln Met Ala Asp Ala Ala Thr Ile Ala Thr Met Asn Lys Ala Ala
1               5                   10                  15

Gly Gly Asp Lys Leu Ala Glu Leu Phe Ser Leu Val Pro Asp Leu Leu
                20                  25                  30

Glu Ala Ala Asn Thr Ser Gly Asn Ala Ser Leu Gln Leu Pro Asp Leu
            35                  40                  45

Trp Trp Glu Leu Gly Leu Glu Leu Pro Asp Ala Pro Pro Gly His
        50                  55                  60

Pro Pro Gly Ser Gly Gly Ala Glu Ser Ala Asp Thr Glu Ala Arg Val
```

```
            65                  70                  75                  80
        Arg Ile Leu Ile Ser Val Val Tyr Trp Val Cys Ala Leu Gly Leu
                        85                  90                  95
        Ala Gly Asn Leu Leu Val Leu Tyr Leu Met Lys Ser Met Gln Gly Trp
                    100                 105                 110
        Arg Lys Ser Ser Ile Asn Leu Phe Val Thr Asn Leu Ala Leu Thr Asp
                    115                 120                 125
        Phe Gln Phe Val Leu Thr Leu Pro Phe Trp Ala Val Glu Asn Ala Leu
        130                 135                 140
        Asp Phe Lys Trp Pro Phe Gly Lys Ala Met Cys Lys Ile Val Ser Met
        145                 150                 155                 160
        Val Thr Ser Met Asn Met Tyr Ala Ser Val Phe Phe Leu Thr Ala Met
                        165                 170                 175
        Ser Val Thr Arg Tyr His Ser Val Ala Ser Ala Leu Lys Ser His Arg
                    180                 185                 190
        Thr Arg Gly His Gly Arg Gly Asp Cys Cys Gly Arg Ser Leu Gly Asp
                    195                 200                 205
        Ser Cys Cys Phe Ser Ala Lys Ala Leu Cys Val Trp Ile Trp Ala Leu
        210                 215                 220
        Ala Ala Leu Ala Ser Leu Pro Ser Ala Ile Phe Ser Thr Thr Val Lys
        225                 230                 235                 240
        Val Met Gly Glu Glu Leu Cys Leu Val Arg Phe Pro Asp Lys Leu Leu
                        245                 250                 255
        Gly Arg Asp Arg Gln Phe Trp Leu Gly Leu Tyr His Ser Gln Lys Val
                    260                 265                 270
        Leu Leu Gly Phe Val Leu Pro Leu Gly Ile Ile Ile Leu Cys Tyr Leu
                    275                 280                 285
        Leu Leu Val Arg Phe Ile Ala Asp Arg Arg Ala Ala Gly Thr Lys Gly
        290                 295                 300
        Gly Ala Ala Val Ala Gly Gly Arg Pro Thr Gly Ala Ser Ala Arg Arg
        305                 310                 315                 320
        Leu Ser Lys Val Thr Lys Ser Val Thr Ile Val Val Leu Ser Phe Phe
                        325                 330                 335
        Leu Cys Trp Leu Pro Asn Gln Ala Leu Thr Thr Trp Ser Ile Leu Ile
                    340                 345                 350
        Lys Phe Asn Ala Val Pro Phe Ser Gln Glu Tyr Phe Leu Cys Gln Val
                    355                 360                 365
        Tyr Ala Phe Pro Val Ser Val Cys Leu Ala His Ser Asn Ser Cys Leu
                    370                 375                 380
        Asn Pro Val Leu Tyr Cys Leu Val Arg Arg Glu Phe Arg Lys Ala Leu
        385                 390                 395                 400
        Lys Ser Leu Leu Trp Arg Ile Ala Ser Pro Ser Ile Thr Ser Met Arg
                        405                 410                 415
        Pro Phe Thr Ala Thr Thr Lys Pro Glu His Glu Asp Gln Gly Leu Gln
                    420                 425                 430
        Ala Pro Ala Pro Pro His Ala Ala Glu Pro Asp Leu Leu Tyr Tyr
                    435                 440                 445
        Pro Pro Gly Val Val Val Tyr Ser Gly Gly Arg Tyr Asp Leu Leu Pro
        450                 455                 460
        Ser Ser Ser Ala Tyr
        465

<210> SEQ ID NO 43
```

```
<211> LENGTH: 374
<212> TYPE: PRT
<213> ORGANISM: Homo sapiens

<400> SEQUENCE: 43
```

| | | | | | | | | | | | | | | |
|---|---|---|---|---|---|---|---|---|---|---|---|---|---|---|
|Met|Pro|Thr|Leu|Asn|Thr|Ser|Ala|Ser|Pro|Thr|Phe|Phe|Trp|Ala|
|1| | | |5| | | |10| | | | |15| |
|Asn|Ala|Ser|Gly|Gly|Ser|Val|Leu|Ser|Ala|Asp|Asp|Ala|Pro|Met|Pro|
| | | |20| | | | |25| | | | |30| |
|Val|Lys|Phe|Leu|Ala|Leu|Arg|Leu|Met|Val|Ala|Leu|Ala|Tyr|Gly|Leu|
| | | |35| | | | |40| | | | |45| |
|Val|Gly|Ala|Ile|Gly|Leu|Leu|Gly|Asn|Leu|Ala|Val|Leu|Trp|Val|Leu|
| |50| | | | |55| | | | |60| | | |
|Ser|Asn|Cys|Ala|Arg|Arg|Ala|Pro|Gly|Pro|Ser|Asp|Thr|Phe|Val|
|65| | | | |70| | | | |75| | | | |80|
|Phe|Asn|Leu|Ala|Leu|Ala|Asp|Leu|Gly|Leu|Ala|Leu|Thr|Leu|Pro|Phe|
| | | | |85| | | | |90| | | | |95| |
|Trp|Ala|Ala|Glu|Ser|Ala|Leu|Asp|Phe|His|Trp|Pro|Phe|Gly|Gly|Ala|
| | | |100| | | | |105| | | | |110| |
|Leu|Cys|Lys|Met|Val|Leu|Thr|Ala|Thr|Val|Leu|Asn|Val|Tyr|Ala|Ser|
| | | |115| | | | |120| | | | |125| |
|Ile|Phe|Leu|Ile|Thr|Ala|Leu|Ser|Val|Ala|Arg|Tyr|Trp|Val|Val|Ala|
| | |130| | | | |135| | | | |140| | |
|Met|Ala|Ala|Gly|Pro|Gly|Thr|His|Leu|Ser|Leu|Phe|Trp|Ala|Arg|Ile|
|145| | | | |150| | | | |155| | | | |160|
|Ala|Thr|Leu|Ala|Val|Trp|Ala|Ala|Ala|Leu|Val|Thr|Val|Pro|Thr|
| | | | |165| | | | |170| | | | |175| |
|Ala|Val|Phe|Gly|Val|Glu|Gly|Glu|Val|Cys|Gly|Val|Arg|Leu|Cys|Leu|
| | | |180| | | | |185| | | | |190| |
|Leu|Arg|Phe|Pro|Ser|Arg|Tyr|Trp|Leu|Gly|Ala|Tyr|Gln|Leu|Gln|Arg|
| | |195| | | | |200| | | | |205| | |
|Val|Val|Leu|Ala|Phe|Met|Val|Pro|Leu|Gly|Val|Ile|Thr|Thr|Ser|Tyr|
| |210| | | | |215| | | | |220| | | |
|Leu|Leu|Leu|Leu|Ala|Phe|Leu|Gln|Arg|Arg|Gln|Arg|Arg|Gln|Asp|
|225| | | | |230| | | | |235| | | | |240|
|Ser|Arg|Val|Val|Ala|Arg|Ser|Val|Arg|Ile|Leu|Val|Ala|Ser|Phe|Phe|
| | | |245| | | | |250| | | | |255| |
|Leu|Cys|Trp|Phe|Pro|Asn|His|Val|Val|Thr|Leu|Trp|Gly|Val|Leu|Val|
| | |260| | | | |265| | | | |270| | |
|Lys|Phe|Asp|Leu|Val|Pro|Trp|Asn|Ser|Thr|Phe|Tyr|Thr|Ile|Gln|Thr|
| | |275| | | | |280| | | | |285| | |
|Tyr|Val|Phe|Pro|Val|Thr|Thr|Cys|Leu|Ala|His|Ser|Asn|Ser|Cys|Leu|
| |290| | | | |295| | | | |300| | | |
|Asn|Pro|Val|Leu|Tyr|Cys|Leu|Leu|Arg|Arg|Glu|Pro|Arg|Gln|Ala|Leu|
|305| | | | |310| | | | |315| | | | |320|
|Ala|Gly|Thr|Phe|Arg|Asp|Leu|Arg|Leu|Arg|Leu|Trp|Pro|Gln|Gly|Gly|
| | | |325| | | | |330| | | | |335| |
|Gly|Trp|Val|Gln|Gln|Val|Ala|Leu|Lys|Gln|Val|Gly|Arg|Arg|Trp|Val|
| | | |340| | | | |345| | | | |350| |
|Ala|Ser|Asn|Pro|Arg|Glu|Ser|Arg|Pro|Ser|Thr|Leu|Leu|Thr|Asn|Leu|
| | | |355| | | | |360| | | | |365| |
|Asp|Arg|Gly|Thr|Pro|Gly|
| | |370| | | |

```
<210> SEQ ID NO 44
<211> LENGTH: 20
<212> TYPE: PRT
<213> ORGANISM: Mus musculus

<400> SEQUENCE: 44

Met Glu Thr Asp Thr Leu Leu Leu Trp Val Leu Leu Leu Trp Val Pro
1               5                   10                  15

Gly Ser Thr Gly
            20

<210> SEQ ID NO 45
<211> LENGTH: 126
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Val Ser Ser Thr
            20                  25                  30

Ala Val Ala Trp Phe Arg Gln Ala Pro Gly Lys Glu Arg Glu Phe Val
        35                  40                  45

Ala Gly Ile Gly Gly Ser Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Val Arg Pro Gly Arg Pro Leu Ile Thr Ser Arg Asp Ala Asn Leu
            100                 105                 110

Tyr Asp Tyr Trp Gly Gln Gly Thr Leu Val Thr Val Ser Ser
        115                 120                 125

<210> SEQ ID NO 46
<211> LENGTH: 126
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Ser Thr
            20                  25                  30

Ala Val Ala Trp Phe Arg Gln Ala Pro Gly Lys Glu Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Arg Val Ala Asn Leu
            100                 105                 110

Tyr Pro Tyr Trp Gly Gln Gly Thr Leu Val Thr Val Ser Ser
```

<210> SEQ ID NO 47
<211> LENGTH: 126
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Tyr Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125

<210> SEQ ID NO 48
<211> LENGTH: 126
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ala Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125

<210> SEQ ID NO 49
<211> LENGTH: 126
<212> TYPE: PRT
<213> ORGANISM: Artificial Sequence
<220> FEATURE:
<223> OTHER INFORMATION: Synthetic Construct

<400> SEQUENCE: 49

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125

<210> SEQ ID NO 50
<211> LENGTH: 126
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125

<210> SEQ ID NO 51
<211> LENGTH: 126
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Ala Tyr Ala Asp Ser Val

```
                    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Pro Leu Ile Thr Ser Lys Val Ala Asp Leu
                100                 105                 110

Tyr Pro Tyr Trp Gly Gln Gly Thr Leu Val Thr Val Ser Ser
            115                 120                 125

<210> SEQ ID NO 52
<211> LENGTH: 126
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Tyr Ile Asp Glu Thr
                 20                  25                  30

Ala Val Ala Trp Phe Arg Gln Ala Pro Gly Lys Glu Arg Glu Phe Val
             35                  40                  45

Ala Gly Ile Gly Gly Gly Val Asp Ile Thr Glu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Pro Leu Ile Thr Ser Lys Val Ala Asp Leu
                100                 105                 110

Tyr Pro Tyr Trp Gly Gln Gly Thr Leu Val Thr Val Ser Ser
            115                 120                 125

<210> SEQ ID NO 53
<211> LENGTH: 126
<212> TYPE: PRT
<213> ORGANISM: Artificial Sequence
<220> FEATURE:
<223> OTHER INFORMATION: Synthetic Construct

<400> SEQUENCE: 53

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Tyr Ile Asp Glu Thr
                 20                  25                  30

Ala Val Ala Trp Phe Arg Gln Ala Pro Gly Lys Glu Arg Glu Phe Val
             35                  40                  45

Ala Gly Ile Gly Gly Gly Val Asp Ile Thr Gln Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Pro Leu Ile Thr Ser Lys Val Ala Asp Leu
                100                 105                 110
```

```
Tyr Pro Tyr Trp Gly Gln Gly Thr Leu Val Thr Val Ser Ser
        115                 120                 125
```

<210> SEQ ID NO 54
<211> LENGTH: 126
<212> TYPE: PRT
<213> ORGANISM: Artificial Sequence
<220> FEATURE:
<223> OTHER INFORMATION: Synthetic Construct

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125
```

<210> SEQ ID NO 55
<211> LENGTH: 126
<212> TYPE: PRT
<213> ORGANISM: Artificial Sequence
<220> FEATURE:
<223> OTHER INFORMATION: Synthetic Construct

<400> SEQUENCE: 55

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125
```

<210> SEQ ID NO 56
<211> LENGTH: 126
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Lys Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125

<210> SEQ ID NO 57
<211> LENGTH: 126
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Gln Pro Leu Ile Thr Ser Lys Val Ala Asp Leu
            100                 105                 110

Tyr Pro Tyr Trp Gly Gln Gly Thr Leu Val Thr Val Ser Ser
        115                 120                 125

<210> SEQ ID NO 58
<211> LENGTH: 126
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

```
Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Ser Pro Leu Ile Thr Ser Lys Val Ala Asp Leu
                100                 105                 110

Tyr Pro Tyr Trp Gly Gln Gly Thr Leu Val Thr Val Ser Ser
                115                 120                 125

<210> SEQ ID NO 59
<211> LENGTH: 126
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Tyr Ile Asp Glu Thr
                 20                  25                  30

Ala Val Ala Trp Phe Arg Gln Ala Pro Gly Lys Glu Arg Glu Phe Val
                 35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Glu Leu Ile Thr Ser Lys Val Ala Asp Leu
                100                 105                 110

Tyr Pro Tyr Trp Gly Gln Gly Thr Leu Val Thr Val Ser Ser
                115                 120                 125

<210> SEQ ID NO 60
<211> LENGTH: 126
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Arg Tyr Ile Asp Glu Thr
                 20                  25                  30

Ala Val Ala Trp Phe Arg Gln Ala Pro Gly Lys Glu Arg Glu Phe Val
                 35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Gln Leu Ile Thr Ser Lys Val Ala Asp Leu
                100                 105                 110
```

Tyr Pro Tyr Trp Gly Gln Gly Thr Leu Val Thr Val Ser Ser
            115                 120                 125

<210> SEQ ID NO 61
<211> LENGTH: 126
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Ser Leu Ile Thr Ser Lys Val Ala Asp Leu
            100                 105                 110

Tyr Pro Tyr Trp Gly Gln Gly Thr Leu Val Thr Val Ser Ser
            115                 120                 125

<210> SEQ ID NO 62
<211> LENGTH: 126
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Leu Ile Thr Ser Lys Val Ala Asp Leu
            100                 105                 110

Tyr Pro Tyr Trp Gly Gln Gly Thr Leu Val Thr Val Ser Ser
            115                 120                 125

<210> SEQ ID NO 63
<211> LENGTH: 126
<212> TYPE: PRT
<213> ORGANISM: Artificial Sequence
<220> FEATURE:
<223> OTHER INFORMATION: Synthetic Construct

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Gly Ile Thr Ser Lys Val Ala Asp Leu
            100                 105                 110

Tyr Pro Tyr Trp Gly Gln Gly Thr Leu Val Thr Val Ser Ser
            115                 120                 125
```

<210> SEQ ID NO 64
<211> LENGTH: 126
<212> TYPE: PRT
<213> ORGANISM: Artificial Sequence
<220> FEATURE:
<223> OTHER INFORMATION: Synthetic Construct

<400> SEQUENCE: 64

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45

Ala Gly Ile Gly Gly Val Asp Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Pro Gly Arg Pro Gln Ile Thr Ser Lys Val Ala Asp Leu
            100                 105                 110

Tyr Pro Tyr Trp Gly Gln Gly Thr Leu Val Thr Val Ser Ser
            115                 120                 125
```

<210> SEQ ID NO 65
<211> LENGTH: 126
<212> TYPE: PRT
<213> ORGANISM: Artificial Sequence
<220> FEATURE:
<223> OTHER INFORMATION: Synthetic Construct

<400> SEQUENCE: 65

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Tyr Ile Asp Glu Thr
            20                  25                  30

Ala Val Ala Trp Phe Arg Gln Ala Pro Gly Lys Glu Arg Glu Phe Val
        35                  40                  45
```

```
Ala Gly Ile Gly Gly Gly Val Asp Ile Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Pro Thr Ile Thr Ser Lys Val Ala Asp Leu
                100                 105                 110

Tyr Pro Tyr Trp Gly Gln Gly Thr Leu Val Thr Val Ser Ser
            115                 120                 125

<210> SEQ ID NO 66
<211> LENGTH: 126
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Arg Tyr Ile Asp Glu Thr
                20                  25                  30

Ala Val Ala Trp Phe Arg Gln Ala Pro Gly Lys Glu Arg Glu Phe Val
            35                  40                  45

Ala Gly Ile Gly Gly Gly Val Asp Ile Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Arg Pro Gly Arg Pro Leu Ile Thr Glu Lys Val Ala Asp Leu
                100                 105                 110

Tyr Pro Tyr Trp Gly Gln Gly Thr Leu Val Thr Val Ser Ser
            115                 120                 125

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Ser Gly Gly Gly Gly Ser Gly Gly Gly Gly
 1               5                  10
```